US012774473B2

(12) United States Patent
Fitoussi et al.

(10) Patent No.: US 12,774,473 B2
(45) Date of Patent: Oct. 27, 2026

(54) RECOMBINANT AAV VECTORS AND METHODS OF USING THE SAME

(71) Applicants: GENSIGHT BIOLOGICS SA, Paris (FR); Serge Fitoussi, Saint Maur des Fosses (FR); Barrett Katz, New York, NY (US)

(72) Inventors: Serge Fitoussi, Saint Maur des Fosses (FR); Barrett Katz, New York, NY (US)

(73) Assignee: GENSIGHT BIOLOGICS SA, Paris (FR)

( * ) Notice: Subject to any disclaimer, the term of this patent is extended or adjusted under 35 U.S.C. 154(b) by 1642 days.

(21) Appl. No.: 16/973,900

(22) PCT Filed: Jun. 11, 2019

(86) PCT No.: PCT/US2019/036487
§ 371 (c)(1),
(2) Date: Dec. 10, 2020

(87) PCT Pub. No.: WO2019/241206
PCT Pub. Date: Dec. 19, 2019

(65) Prior Publication Data

US 2021/0189424 A1 Jun. 24, 2021

Related U.S. Application Data

(60) Provisional application No. 62/683,501, filed on Jun. 11, 2018.

(51) Int. Cl.
*C12N 15/86* (2006.01)
*A61K 48/00* (2006.01)

(52) U.S. Cl.
CPC ............ *C12N 15/86* (2013.01); *A61K 48/005* (2013.01); *C12N 2750/14141* (2013.01)

(58) Field of Classification Search
CPC .......... C12N 15/86; C12N 2750/14141; C12N 9/0028; C12N 9/1085; C12N 2750/14143; C12N 9/0036; C12N 9/0053; A61K 48/005; A61K 48/00; A61P 27/02; C12Y 106/05003; C12Y 109/03001
See application file for complete search history.

(56) References Cited

U.S. PATENT DOCUMENTS 6,218,117 B1 * 4/2001 Herrnstadt ........... C12Q 1/6827 536/24.31
9,097,889 B2 * 8/2015 Kalkbrenner ...... G02B 21/0056
2009/0306188 A1 * 12/2009 Corral-Debrinski ......................... C12N 9/0089 435/325
2013/0323302 A1 * 12/2013 Constable ............. A61K 38/45 435/239
2016/0040185 A1 * 2/2016 Hwang .................. C12N 15/85 435/325

FOREIGN PATENT DOCUMENTS

CN 104 450 747 A 3/2015
WO WO-2006117250 A2 * 11/2006 ........... A61K 48/005
WO WO 2008/101233 A2 8/2008

OTHER PUBLICATIONS

Yang et al. ("Long-term outcomes of gene therapy for the treatment of Leber's hereditary optic neuropathy" Received Mar. 11, 2016, Department of Ophthalmology, Tongji Hospital, Tongji Medical College, Huazhong University of Science and Technology, Wuhan, People's Republic of China). (Year: 2016).*
Jia Zhansheng, "Cell Therapy for Liver Disease: Fundamentals and Clinical Applications," Apr. 30, 2005, p. 409, *People's Medical Publishing House* (*1st Edition*).
Hélène Cwerman-Thibault, et al., "Nuclear Expression of Mitochondrial ND4 Leads to the Protein Assembling in Complex I and Prevents Optic Atrophy and Visual Loss," *Molecular Therapy-Methods & Clinical Development*, 2015, pp. 1-15, vol. 2, No. 15003.
Enqi Liu, et al., "Eukaryotic Cell Gene Expression Systems," *Animal Models of Human Diseases*, Sep. 9, 2015, pp. 1-2.
Xing Wan, et al., "Efficacy and Safety of rAAV2-ND4 Treatment for Leber's Hereditary Optic Neuropathy," *Scientific Reports*, Feb. 19, 2016, pp. 1-10, vol. 6, No. 21587.
Shuo Yang, et al., "Long-term outcomes of gene therapy for the treatment of Leber's hereditary optic neuropathy," *EBioMedicine*, vol. 10, pp. 258-267 (2016).
International Search Report, issued by the European Patent Office, in corresponding International Application No. PCT/US2019/036487 (3 pages).
Newman, N. J. et al., "Efficacy and Safety of Intravitreal Gene Therapy for Leber Hereditary Optic Neuropathy Treated within 6 Months of Disease Onset," Ophthalmology: Journal of The American Academy of Ophthalmology, vol. 128, No. 5, (2021), pp. 649-660.

* cited by examiner

*Primary Examiner* — Brian Whiteman
(74) *Attorney, Agent, or Firm* — Finnegan, Henderson, Farabow, Garrett & Dunner, LLP

(57) ABSTRACT

The present disclosure relates to recombinant vectors expressing the human ND4 gene, methods of preparing recombinant vectors expressing the human ND4 gene, and uses thereof. Recombinant AAV2 vectors as disclosed herein are useful in treating Leber Hereditary Optic Neuroretinopathy (LHON), including ND4-related LHON.

12 Claims, 7 Drawing Sheets

Specification includes a Sequence Listing.

SEQUENCE LISTING

<160> NUMBER OF SEQ ID NOS: 27

<210> SEQ ID NO 1
<211> LENGTH: 595
<212> TYPE: DNA
<213> ORGANISM: Homo sapiens

<400> SEQUENCE: 1
aacatgtgga atccccagtc ccagtgcaca gcagccgggt cctagctatt ggtattgtta 60
gaaggactat ggttgagaat gtgtggggtg gggaaaacca aaaatgcagg ccctggctca 120
gtcaccagga agggggtgct ccgaggcctt tgagggacct gagctcacag aactacagac 180
agcagatcat gaggctcaca ctttctggcc accaagtgcc actctgctgg gcatgtggag 240
tgtgcgtgtg gtgtggtggt aaggatggaa ccaaaagagg aagctgtgta tgtgtacccc 300
catgtgagga ggaagaaaca gaatagaggg tggggttgga ggagagatgt ataaagaccc 360
tcaaagggaa aaataattcc ttttttgtat tcactgactg agctgatgca tttcttattt 420
ggggagcatt ttgggtaata tttaaaaaaa aaaaaaaactg tcaagtgatc actgggcacc 480
gaattcgttt ataatcttgt tctaaaccca gcaatttctc ttcttgtgtt ccagaattac 540
cacaacatgc tcgcctggca gcggagggaa aggggcggtg ggcgtcccag tgctc 595

<210> SEQ ID NO 2
<211> LENGTH: 1374
<212> TYPE: DNA
<213> ORGANISM: Homo sapiens

<400> SEQUENCE: 2
atgagaaacc agtgataatg tctgggttca gggacagcag caggatggga gacagatgca 60
taaacatcag ggtgttctct ctggtgaatg agggcttcat gttattaatg tggtgagtca 120
gtgagcccca ctgggtagtg gtaaacatgt acaggctgta gagggctgtg accagcatgt 180
tcagtcctgt caggagcagg gtgatgttgc tccaggagaa tgttgtcacc agcactgaca 240
gctctcccag caggttaatt gtagggggca gagccaggtt ggccagacta gccaggagcc 300
accagaaagc catcagtggg agcagggtct ggagcccctg actcaggatc ataattcttg 360
agtgagttct ttcatagttg ctatttgcca ggcagaacag gaggctgctg gtcagcccat 420
gagcaatcat gaggatcact gccccagtaa aggaccaggg tgtctgaatc agaatggcag 480
tcaccaccag tgccatgtgg ctgatggagc tgtaagcaat caggctcttg aggtcagtct 540
gcctgagaca gatggagctg gtcatgatca taccccagag gctcagaacc aggaaagggt 600
aagccatgtg ctttgtcaga gggttcagga tcagggtgag cctcatcata ccataaccac 660
ccagcttcag gaggacagca gccaggacca tggagccagc tattggagct tccacatgag 720
ccttggggag ccagaggtgc aggccataga ggggcatctt caccataaag gccattgtat 780
aagccagcca catcaggttg tttgcccagg agttactcag ctcctgggca gtcagagtca 840
gcaggaggat gttcaggcta cccagtgtgt tgtgggtata gatcagtgca atcagcaggg 900
gcagtgagcc caccagtgta taaaagagaa agtaggtgcc tgcattcagc ctctcaggct 960
gatttcccca cctagtgatg atggccaggg ttgggatgag agtggtctca aagaagatat 1020
agaacatgat cagctcagtg gctgtgaagg tcataatcag gctgatttgc aggctaatga 1080
gcatggacag gtacagcttt ttccttgaca gaggctctga gctgaggtgc ctctgactgg 1140
ccatgatagt cagaggcagc agccatgtgg tcagcatgag caggggggtt gtcaggggat 1200
cagaggaaaa ggtaggggag catgaaaaga ggttattatt aatctggttg aaaaacagca 1260
gtgggatgat gctgataatc aggctgtggg ttgtggtgtt aatccaaatc atgtgctttt 1320
tgctcagcca tgtgagaggc agcagcatga tggttggcac aatcagcttc agca 1374

<210> SEQ ID NO 3
<211> LENGTH: 84
<212> TYPE: DNA
<213> ORGANISM: Homo sapiens

<400> SEQUENCE: 3
agtcctcctt tccaggtacc acacactccc ccccacacag ccagtcagga gcctggatga 60
cagtgtatgg gggctggcag ccat 84

<210> SEQ ID NO 4
<211> LENGTH: 398
<212> TYPE: DNA
<213> ORGANISM: Homo sapiens

<400> SEQUENCE: 4
aattctttgc caaagtgatg ggccagcaca cagaccagca cgttgcccag gagctgtggg 60
aggaagataa gaggtatgaa catgattagc aaaagggcct agcttggact cagaataatc 120
cagccttatc ccaaccataa aataaaagca gaatggtagc tggattgtag ctgctattag 180
caatatgaaa cctcttacat cagttacaat ttatatgcag aaatatttat atgcagaaat 240
attgctattg ccttaaccca gaaattatca ctgttattct ttagaatggt gcaaagaggc 300
atgatacatt gtatcattat tgccctgaaa gaaagagatt agggaaagta ttagaaataa 360
gataaacaaa aaagtatatt aaaagaagaa agcatttt 398

<210> SEQ ID NO 5
<211> LENGTH: 654
<212> TYPE: DNA
<213> ORGANISM: Homo sapiens

<400> SEQUENCE: 5
ggaggctgga tcggtcccgg tgtcttctat ggaggtcaaa acagcgtgga tggcgtctcc 60
aggcgatctg acggttcact aaacgagctc tgcttatata gacctcccac cgtacacgcc 120
taccgcccat ttgcgtcaat ggggcggagt tgttacgaca ttttggaaag tcccgttgat 180
tttggtgcca aaacaaactc ccattgacgt caatggggtg gagacttgga aatccccgtg 240
agtcaaaccg ctatccacgc ccattgatgt actgccaaaa ccgcatcacc atggtaatag 300
cgatgactaa tacgtagatg tactgccaag taggaaagtc ccataaggtc atgtactggg 360
cataatgcca ggcgggccat ttaccgtcat tgacgtcaat agggggcgta cttggcatat 420
gatacacttg atgtactgcc aagtgggcag tttaccgtaa atactccacc cattgacgtc 480
aatggaaagt ccctattggc gttactatgg gaacatacgt cattattgac gtcaatgggc 540
gggggtcgtt gggcggtcag ccaggcgggc catttaccgt aagttatgta acgcggaact 600
ccatatatgg gctatgaact aatgaccccg taattgatta ctattaataa ctag 654

<210> SEQ ID NO 6
<211> LENGTH: 128
<212> TYPE: DNA
<213> ORGANISM: Homo sapiens

<400> SEQUENCE: 6
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgc 128

<210> SEQ ID NO 7
<211> LENGTH: 130
<212> TYPE: DNA
<213> ORGANISM: Homo sapiens

<400> SEQUENCE: 7
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct 130

<210> SEQ ID NO 8
<211> LENGTH: 456
<212> TYPE: DNA
<213> ORGANISM: Homo sapiens

<400> SEQUENCE: 8
acgcgccctg tagcggcgca ttaagcgcgg cgggtgtggt ggttacgcgc agcgtgaccg 60
ctacacttgc cagcgcccta gcgcccgctc ctttcgcttt cttcccttcc tttctcgcca 120
cgttcgccgg ctttccccgt caagctctaa atcgggggct ccctttaggg ttccgattta 180

```
gtgctttacg gcacctcgac cccaaaaaac ttgattaggg tgatggttca cgtagtgggc    240

catcgccctg atagacggtt tttcgccctt tgacgttgga gtccacgttc tttaatagtg    300

gactcttgtt ccaaactgga acaacactca accctatctc ggtctattct tttgatttat    360

aagggatttt gccgatttcg gcctattggt taaaaaatga gctgatttaa caaaaattta    420

acgcgaattt taacaaaata ttaacgctta caattt                              456


<210> SEQ ID NO 9
<211> LENGTH: 792
<212> TYPE: DNA
<213> ORGANISM: Homo sapiens

<400> SEQUENCE: 9

attgaacaag atggattgca cgcaggttct ccggccgctt gggtggagag gctattcggc     60

tatgactggg cacaacagac aatcggctgc tctgatgccg ccgtgttccg gctgtcagcg    120

caggggcgcc cggttctttt tgtcaagacc gacctgtccg gtgccctgaa tgaactgcaa    180

gacgaggcag cgcggctatc gtggctggcc acgacgggcg ttccttgcgc agctgtgctc    240

gacgttgtca ctgaagcggg aagggactgg ctgctattgg gcgaagtgcc ggggcaggat    300

ctcctgtcat ctcaccttgc tcctgccgag aaagtatcca tcatggctga tgcaatgcgg    360

cggctgcata cgcttgatcc ggctacctgc ccattcgacc accaagcgaa acatcgcatc    420

gagcgagcac gtactcggat ggaagccggt cttgtcgatc aggatgatct ggacgaagag    480

catcaggggc tcgcgccagc cgaactgttc gccaggctca aggcgagcat gcccgacggc    540

gaggatctcg tcgtgaccca tggcgatgcc tgcttgccga atatcatggt ggaaaatggc    600

cgcttttctg gattcatcga ctgtggccgg ctgggtgtgg cggaccgcta tcaggacata    660

gcgttggcta cccgtgatat tgctgaagag cttggcggcg aatgggctga ccgcttcctc    720

gtgctttacg gtatcgccgc tcccgattcg cagcgcatcg ccttctatcg ccttcttgac    780

gagttcttct ga                                                        792


<210> SEQ ID NO 10
<211> LENGTH: 615
<212> TYPE: DNA
<213> ORGANISM: Homo sapiens

<400> SEQUENCE: 10

aaaggatctt cttgagatcc tttttttctg cgcgtaatct gctgcttgca aacaaaaaaa     60

ccaccgctac cagcggtggt ttgtttgccg gatcaagagc taccaactct ttttccgaag    120

gtaactggct tcagcagagc gcagatacca aatactgtcc ttctagtgta gccgtagtta    180

ggccaccact tcaagaactc tgtagcaccg cctacatacc tcgctctgct aatcctgtta    240

ccagtggctg ctgccagtgg cgataagtcg tgtcttaccg ggttggactc aagacgatag    300

ttaccggata aggcgcagcg gtcgggctga acggggggtt cgtgcacaca gcccagcttg    360

gagcgaacga cctacaccga actgagatac ctacagcgtg agctatgaga aagcgccacg    420

cttcccgaag ggagaaaggc ggacaggtat ccggtaagcg gcagggtcgg aacaggagag    480

cgcacgaggg agcttccagg gggaaacgcc tggtatcttt atagtcctgt cgggtttcgc    540

cacctctgac ttgagcgtcg atttttgtga tgctcgtcag gggggcggag cctatggaaa    600

aacgccagca acgcg                                                     615


<210> SEQ ID NO 11
```

<211> LENGTH: 20
<212> TYPE: PRT
<213> ORGANISM: Homo sapiens

<400> SEQUENCE: 11

Met Ala Ala Ser Pro His Thr Leu Ser Ser Arg Leu Leu Thr Gly Cys
1               5                   10                  15

Val Gly Gly Ser
            20

<210> SEQ ID NO 12
<211> LENGTH: 28
<212> TYPE: PRT
<213> ORGANISM: Homo sapiens

<400> SEQUENCE: 12

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr
            20                  25

<210> SEQ ID NO 13
<211> LENGTH: 459
<212> TYPE: PRT
<213> ORGANISM: Homo sapiens

<400> SEQUENCE: 13

Met Leu Lys Leu Ile Val Pro Thr Ile Met Leu Leu Pro Leu Thr Trp
1               5                   10                  15

Leu Ser Lys Lys His Met Ile Trp Ile Asn Thr Thr Thr His Ser Leu
            20                  25                  30

Ile Ile Ser Ile Ile Pro Leu Leu Phe Phe Asn Gln Ile Asn Asn Asn
        35                  40                  45

Leu Phe Ser Cys Ser Pro Thr Phe Ser Ser Asp Pro Leu Thr Thr Pro
    50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
                85                  90                  95

Ser Met Leu Ile Ser Leu Gln Ile Ser Leu Ile Met Thr Phe Thr Ala
            100                 105                 110

Thr Glu Leu Ile Met Phe Tyr Ile Phe Phe Glu Thr Thr Leu Ile Pro
        115                 120                 125

Thr Leu Ala Ile Ile Thr Arg Trp Gly Asn Gln Pro Glu Arg Leu Asn
    130                 135                 140

Ala Gly Thr Tyr Phe Leu Phe Tyr Thr Leu Val Gly Ser Leu Pro Leu
145                 150                 155                 160

Leu Ile Ala Leu Ile Tyr Thr His Asn Thr Leu Gly Ser Leu Asn Ile
                165                 170                 175

Leu Leu Leu Thr Leu Thr Ala Gln Glu Leu Ser Asn Ser Trp Ala Asn
            180                 185                 190

Asn Leu Met Trp Leu Ala Tyr Thr Met Ala Phe Met Val Lys Met Pro
        195                 200                 205

Leu Tyr Gly Leu His Leu Trp Leu Pro Lys Ala His Val Glu Ala Pro
    210                 215                 220

Ile Ala Gly Ser Met Val Leu Ala Ala Val Leu Leu Lys Leu Gly Gly
225                 230                 235                 240

```
Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
            260                 265                 270

Ser Ser Ile Cys Leu Arg Gln Thr Asp Leu Lys Ser Leu Ile Ala Tyr
        275                 280                 285

Ser Ser Ile Ser His Met Ala Leu Val Val Thr Ala Ile Leu Ile Gln
    290                 295                 300

Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
                325                 330                 335

Thr His Ser Arg Ile Met Ile Leu Ser Gln Gly Leu Gln Thr Leu Leu
            340                 345                 350

Pro Leu Met Ala Phe Trp Trp Leu Leu Ala Ser Leu Ala Asn Leu Ala
        355                 360                 365

Leu Pro Pro Thr Ile Asn Leu Leu Gly Glu Leu Ser Val Leu Val Thr
    370                 375                 380

Thr Phe Ser Trp Ser Asn Ile Thr Leu Leu Leu Thr Gly Leu Asn Met
385                 390                 395                 400

Leu Val Thr Ala Leu Tyr Ser Leu Tyr Met Phe Thr Thr Thr Gln Trp
                405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
        435                 440                 445

Leu Asn Pro Asp Ile Ile Thr Gly Phe Ser Ser
    450                 455
```

<210> SEQ ID NO 14
<211> LENGTH: 595
<212> TYPE: DNA
<213> ORGANISM: Homo sapiens

<400> SEQUENCE: 14

```
gagcactggg acgcccaccg cccctttccc tccgctgcca ggcgagcatg ttgtggtaat      60

tctggaacac aagaagagaa attgctgggt ttagaacaag attataaacg aattcggtgc     120

ccagtgatca cttgacagtt tttttttttt ttaaatatta cccaaaatgc tccccaaata     180

agaaatgcat cagctcagtc agtgaataca aaaaaggaat tatttttccc tttgagggtc     240

tttatacatc tctcctccaa ccccaccctc tattctgttt cttcctcctc acatgggggt     300

acacatacac agcttcctct tttggttcca tccttaccac cacaccacac gcacactcca     360

catgcccagc agagtggcac ttggtggcca gaaagtgtga gcctcatgat ctgctgtctg     420

tagttctgtg agctcaggtc cctcaaaggc ctcggagcac ccccttcctg gtgactgagc     480

cagggcctgc atttttggtt ttccccaccc cacacattct caaccatagt ccttctaaca     540

ataccaatag ctaggacccg gctgctgtgc actgggactg gggattccac atgtt          595
```

<210> SEQ ID NO 15
<211> LENGTH: 1374
<212> TYPE: DNA
<213> ORGANISM: Homo sapiens

<400> SEQUENCE: 15

```
tgctgaagct gattgtgcca accatcatgc tgctgcctct cacatggctg agcaaaaagc      60
```

acatgatttg gattaacacc acaacccaca gcctgattat cagcatcatc ccactgctgt 120
ttttcaacca gattaataat aacctctttt catgctcccc taccttttcc tctgatcccc 180
tgacaacccc cctgctcatg ctgaccacat ggctgctgcc tctgactatc atggccagtc 240
agaggcacct cagctcagag cctctgtcaa ggaaaaagct gtacctgtcc atgctcatta 300
gcctgcaaat cagcctgatt atgaccttca cagccactga gctgatcatg ttctatatct 360
tctttgagac cactctcatc ccaaccctgg ccatcatcac taggtgggga aatcagcctg 420
agaggctgaa tgcaggcacc tactttctct tttatacact ggtgggctca ctgcccctgc 480
tgattgcact gatctatacc cacaacacac tgggtagcct gaacatcctc ctgctgactc 540
tgactgccca ggagctgagt aactcctggg caaacaacct gatgtggctg gcttatacaa 600
tggcctttat ggtgaagatg cccctctatg gcctgcacct ctggctcccc aaggctcatg 660
tggaagctcc aatagctggc tccatggtcc tggctgctgt cctcctgaag ctgggtggtt 720
atggtatgat gaggctcacc ctgatcctga accctctgac aaagcacatg gcttaccctt 780
tcctggttct gagcctctgg ggtatgatca tgaccagctc catctgtctc aggcagactg 840
acctcaagag cctgattgct tacagctcca tcagccacat ggcactggtg gtgactgcca 900
ttctgattca gacaccctgg tcctttactg gggcagtgat cctcatgatt gctcatgggc 960
tgaccagcag cctcctgttc tgcctggcaa atagcaacta tgaaagaact cactcaagaa 1020
ttatgatcct gagtcagggg ctccagaccc tgctcccact gatggctttc tggtggctcc 1080
tggctagtct ggccaacctg gctctgcccc ctacaattaa cctgctggga gagctgtcag 1140
tgctggtgac aacattctcc tggagcaaca tcaccctgct cctgacagga ctgaacatgc 1200
tggtcacagc cctctacagc ctgtacatgt ttaccactac ccagtggggc tcactgactc 1260
accacattaa taacatgaag ccctcattca ccagagagaa caccctgatg tttatgcatc 1320
tgtctcccat cctgctgctg tccctgaacc cagacattat cactggtttc tcat 1374

<210> SEQ ID NO 16
<211> LENGTH: 84
<212> TYPE: DNA
<213> ORGANISM: Homo sapiens

<400> SEQUENCE: 16
atggctgcca gcccccatac actgtcatcc aggctcctga ctggctgtgt ggggggggagt 60 gtgtggtacc tggaaaggag gact 84

<210> SEQ ID NO 17
<211> LENGTH: 1380
<212> TYPE: DNA
<213> ORGANISM: Homo sapiens

<400> SEQUENCE: 17
tcaggatgag aaaccagtga taatgtctgg gttcagggac agcagcagga tgggagacag 60
atgcataaac atcagggtgt tctctctggt gaatgagggc ttcatgttat taatgtggtg 120
agtcagtgag ccccactggg tagtggtaaa catgtacagg ctgtagaggg ctgtgaccag 180
catgttcagt cctgtcagga gcagggtgat gttgctccag gagaatgttg tcaccagcac 240
tgacagctct cccagcaggt taattgtagg gggcagagcc aggttggcca gactagccag 300
gagccaccag aaagccatca gtgggagcag ggtctggagc ccctgactca ggatcataat 360
tcttgagtga gttctttcat agttgctatt tgccaggcag aacaggaggc tgctggtcag 420

```
cccatgagca atcatgagga tcactgcccc agtaaaggac cagggtgtct gaatcagaat    480

ggcagtcacc accagtgcca tgtggctgat ggagctgtaa gcaatcaggc tcttgaggtc    540

agtctgcctg agacagatgg agctggtcat gatcataccc cagaggctca gaaccaggaa    600

agggtaagcc atgtgctttg tcagagggtt caggatcagg gtgagcctca tcataccata    660

accacccagc ttcaggagga cagcagccag gaccatggag ccagctattg gagcttccac    720

atgagccttg ggagccagga ggtgcaggcc atagaggggc atcttcacca taaaggccat    780

tgtataagcc agccacatca ggttgtttgc ccaggagtta ctcagctcct gggcagtcag    840

agtcagcagg aggatgttca ggctacccag tgtgttgtgg gtatagatca gtgcaatcag    900

caggggcagt gagcccacca gtgtataaaa gagaaagtag gtgcctgcat tcagcctctc    960

aggctgattt ccccacctag tgatgatggc cagggttggg atgagagtgg tctcaaagaa   1020

gatatagaac atgatcagct cagtggctgt gaaggtcata atcaggctga tttgcaggct   1080

aatgagcatg gacaggtaca gcttttttcct tgacagaggc tctgagctga ggtgcctctg   1140

actggccatg atagtcagag gcagcagcca tgtggtcagc atgagcaggg gggttgtcag   1200

gggatcagag gaaaaggtag gggagcatga aaagaggtta ttattaatct ggttgaaaaa   1260

cagcagtggg atgatgctga taatcaggct gtgggttgtg gtgttaatcc aaatcatgtg   1320

ctttttgctc agccatgtga gaggcagcag catgatggtt ggcacaatca gcttcagcat   1380
```

```
<210> SEQ ID NO 18
<211> LENGTH: 1380
<212> TYPE: DNA
<213> ORGANISM: Homo sapiens

<400> SEQUENCE: 18

atgctgaagc tgattgtgcc aaccatcatg ctgctgcctc tcacatggct gagcaaaaag     60

cacatgattt ggattaacac cacaacccac agcctgatta tcagcatcat cccactgctg    120

tttttcaacc agattaataa taacctcttt tcatgctccc ctaccttttc ctctgatccc    180

ctgacaaccc ccctgctcat gctgaccaca tggctgctgc ctctgactat catggccagt    240

cagaggcacc tcagctcaga gcctctgtca aggaaaaagc tgtacctgtc catgctcatt    300

agcctgcaaa tcagcctgat tatgaccttc acagccactg agctgatcat gttctatatc    360

ttctttgaga ccactctcat cccaaccctg gccatcatca ctaggtgggg aaatcagcct    420

gagaggctga atgcaggcac ctacttttctc ttttatacac tggtgggctc actgcccctg    480

ctgattgcac tgatctatac ccacaacaca ctgggtagcc tgaacatcct cctgctgact    540

ctgactgccc aggagctgag taactcctgg gcaaacaacc tgatgtggct ggcttataca    600

atggccttta tggtgaagat gcccctctat ggcctgcacc tctggctccc caaggctcat    660

gtggaagctc caatagctgg ctccatggtc ctggctgctg tcctcctgaa gctgggtggt    720

tatggtatga tgaggctcac cctgatcctg aaccctctga caaagcacat ggcttaccct    780

ttcctggttc tgagcctctg ggtatgatc atgaccagct ccatctgtct caggcagact    840

gacctcaaga gcctgattgc ttacagctcc atcagccaca tggcactggt ggtgactgcc    900

attctgattc agacaccctg gtcctttact ggggcagtga tcctcatgat tgctcatggg    960

ctgaccagca gcctcctgtt ctgcctggca aatagcaact atgaaagaac tcactcaaga   1020

attatgatcc tgagtcaggg gctccagacc ctgctcccac tgatggcttt ctggtggctc   1080

ctggctagtc tggccaacct ggctctgccc cctacaatta acctgctggg agagctgtca   1140

gtgctggtga caacattctc ctggagcaac atcaccctgc tcctgacagg actgaacatg   1200
```

ctggtcacag ccctctacag cctgtacatg tttaccacta cccagtgggg ctcactgact 1260
caccacatta ataacatgaa gccctcattc accagagaga acaccctgat gtttatgcat 1320
ctgtctccca tcctgctgct gtccctgaac ccagacatta tcactggttt ctcatcctga 1380

<210> SEQ ID NO 19
<211> LENGTH: 22
<212> TYPE: DNA
<213> ORGANISM: Homo sapiens

<400> SEQUENCE: 19
ctccatcact aggggttcct tg 22

<210> SEQ ID NO 20
<211> LENGTH: 18
<212> TYPE: DNA
<213> ORGANISM: Homo sapiens

<400> SEQUENCE: 20
gtagataagt agcatggc 18

<210> SEQ ID NO 21
<211> LENGTH: 17
<212> TYPE: DNA
<213> ORGANISM: Homo sapiens

<400> SEQUENCE: 21
tagttaatga ttaaccc 17

<210> SEQ ID NO 22
<211> LENGTH: 6489
<212> TYPE: DNA
<213> ORGANISM: Homo sapiens

<400> SEQUENCE: 22
gctcggtccg aacatgtgga atccccagtc ccagtgcaca gcagccgggt cctagctatt 60
ggtattgtta gaaggactat ggttgagaat gtgtggggtg gggaaaacca aaaatgcagg 120
ccctggctca gtcaccagga agggggtgct ccgaggcctt tgagggacct gagctcacag 180
aactacagac agcagatcat gaggctcaca ctttctggcc accaagtgcc actctgctgg 240
gcatgtggag tgtgcgtgtg gtgtggtggt aaggatggaa ccaaaagagg aagctgtgta 300
tgtgtacccc catgtgagga ggaagaaaca gaatagaggg tggggttgga ggagagatgt 360
ataaagaccc tcaaagggaa aaataattcc ttttttgtat tcactgactg agctgatgca 420
tttcttattt ggggagcatt ttgggtaata tttaaaaaaa aaaaaaactg tcaagtgatc 480
actgggcacc gaattcgttt ataatcttgt tctaaaccca gcaatttctc ttcttgtgtt 540
ccagaattac cacaacatgc tcgcctggca gcggagggaa aggggcggtg ggcgtcccag 600
tgctcagatc tctcgagtca ggatgagaaa ccagtgataa tgtctgggtt cagggacagc 660
agcaggatgg gagacagatg cataaacatc agggtgttct ctctggtgaa tgagggcttc 720
atgttattaa tgtggtgagt cagtgagccc cactgggtag tggtaaacat gtacaggctg 780
tagagggctg tgaccagcat gttcagtcct gtcaggagca gggtgatgtt gctccaggag 840
aatgttgtca ccagcactga cagctctccc agcaggttaa ttgtaggggg cagagccagg 900
ttggccagac tagccaggag ccaccagaaa gccatcagtg ggagcagggt ctggagcccc 960
tgactcagga tcataattct tgagtgagtt ctttcatagt tgctatttgc caggcagaac 1020

```
aggaggctgc tggtcagccc atgagcaatc atgaggatca ctgccccagt aaaggaccag   1080
ggtgtctgaa tcagaatggc agtcaccacc agtgccatgt ggctgatgga gctgtaagca   1140
atcaggctct tgaggtcagt ctgcctgaga cagatggagc tggtcatgat catacccccag  1200
aggctcagaa ccaggaaagg gtaagccatg tgctttgtca gagggttcag gatcagggtg   1260
agcctcatca taccataacc acccagcttc aggaggacag cagccaggac catggagcca   1320
gctattggag cttccacatg agccttgggg agccagaggt gcaggccata gaggggcatc   1380
ttcaccataa aggccattgt ataagccagc cacatcaggt tgtttgccca ggagttactc   1440
agctcctggg cagtcagagt cagcaggagg atgttcaggc tacccagtgt gttgtgggta   1500
tagatcagtg caatcagcag gggcagtgag cccaccagtg tataaaagag aaagtaggtg   1560
cctgcattca gcctctcagg ctgatttccc cacctagtga tgatggccag ggttgggatg   1620
agagtggtct caaagaagat atagaacatg atcagctcag tggctgtgaa ggtcataatc   1680
aggctgattt gcaggctaat gagcatggac aggtacagct tttccttgga cagaggctct   1740
gagctgaggt gcctctgact ggccatgata gtcagaggca gcagccatgt ggtcagcatg   1800
agcagggggg ttgtcagggg atcagaggaa aaggtagggg agcatgaaaa gaggttatta   1860
ttaatctggt tgaaaaacag cagtgggatg atgctgataa tcaggctgtg ggttgtggtg   1920
ttaatccaaa tcatgtgctt tttgctcagc catgtgagag gcagcagcat gatggttggc   1980
acaatcagct tcagcatagt cctcctttcc aggtaccaca cactcccccc cacacagcca   2040
gtcaggagcc tggatgacag tgtatggggg ctggcagcca tgtcgactct agaggatccc   2100
cggggaattc aatcgatgtt cgaatcccaa ttctttgcca aagtgatggg ccagcacaca   2160
gaccagcacg ttgcccagga gctgtgggag gaagataaga ggtatgaaca tgattagcaa   2220
aagggcctag cttggactca gaataatcca gccttatccc aaccataaaa taaaagcaga   2280
atggtagctg gattgtagct gctattagca atatgaaacc tcttacatca gttacaattt   2340
atatgcagaa atatttatat gcagaaatat tgctattgcc ttaacccaga aattatcact   2400
gttattcttt agaatggtgc aaagaggcat gatacattgt atcattattg ccctgaaaga   2460
aagagattag ggaaagtatt agaaataaga taaacaaaaa agtatattaa aagaagaaag   2520
catttttgt gggcctatag actctatagg cggtacttac gtcactcttg gcacggggaa    2580
tccgcgttcc aatgcaccgt tcccggccgg gattcgaatc cgcggaggct ggatcggtcc   2640
cggtgtcttc tatggaggtc aaaacagcgt ggatggcgtc tccaggcgat ctgacggttc   2700
actaaacgag ctctgcttat atagacctcc caccgtacac gcctaccgcc catttgcgtc   2760
aatggggcgg agttgttacg acattttgga aagtcccgtt gattttggtg ccaaaacaaa   2820
ctcccattga cgtcaatggg gtggagactt ggaaatcccc gtgagtcaaa ccgctatcca   2880
cgcccattga tgtactgcca aaaccgcatc accatggtaa tagcgatgac taatacgtag   2940
atgtactgcc aagtaggaaa gtcccataag gtcatgtact gggcataatg ccaggcgggc   3000
catttaccgt cattgacgtc aatagggggc gtacttggca tatgatacac ttgatgtact   3060
gccaagtggg cagtttaccg taaatactcc acccattgac gtcaatggaa agtccctatt   3120
ggcgttacta tgggaacata cgtcattatt gacgtcaatg ggcgggggtc gttgggcggt   3180
cagccaggcg ggccatttac cgtaagttat gtaacgcgga actccatata tgggctatga   3240
actaatgacc ccgtaattga ttactattaa taactagacg cgtgcggccg tagataagta   3300
gcatggcggg ttaatcatta actacaagga acccctagtg atggagttgg ccactccctc   3360
tctgcgcgct cgctcgctca ctgaggccgg gcgaccaaag gtcgcccgac gcccgggctt   3420
```

```
tgcccgggcg gcctcagtga gcgagcgagc gcgccagctg gcgtaatagc gaagaggccc   3480
gcaccgatcg cccttcccaa cagttgcgca gcctgaatgg cgaatggatt ccagacgatt   3540
gagcgtcaaa atgtaggtat ttccatgagc gtttttccgt tgcaatggct ggcggtaata   3600
ttgttctgga tattaccagc aaggccgata gtttgagttc ttctactcag gcaagtgatg   3660
ttattactaa tcaaagaagt attgcgacaa cggttaattt gcgtgatgga cagactcttt   3720
tactcggtgg cctcactgat tataaaaaca cttctcagga ttctggcgta ccgttcctgt   3780
ctaaaatccc tttaatcggc ctcctgttta gctcccgctc tgattctaac gaggaaagca   3840
cgttatacgt gctcgtcaaa gcaaccatag tacgcgccct gtagcggcgc attaagcgcg   3900
gcgggtgtgg tggttacgcg cagcgtgacc gctacacttg ccagcgccct agcgcccgct   3960
cctttcgctt tcttcccttc ctttctcgcc acgttcgccg gctttccccg tcaagctcta   4020
aatcgggggc tccctttagg gttccgattt agtgctttac ggcacctcga ccccaaaaaa   4080
cttgattagg gtgatggttc acgtagtggg ccatcgccct gatagacggt ttttcgccct   4140
ttgacgttgg agtccacgtt ctttaatagt ggactcttgt tccaaactgg aacaacactc   4200
aaccctatct cggtctattc ttttgattta taagggattt tgccgatttc ggcctattgg   4260
ttaaaaaatg agctgattta acaaaaattt aacgcgaatt ttaacaaaat attaacgctt   4320
acaatttagg tggcactttt cggggaaatg tgcgcggaac ccctatttgt ttatttttct   4380
aaatacattc aaatatgtat ccgctcatga gacaataacc ctgataaatg cttcaataat   4440
agcacctaga tcaagagaca ggatgaggat cgtttcgcat gattgaacaa gatggattgc   4500
acgcaggttc tccggccgct tgggtggaga ggctattcgg ctatgactgg gcacaacaga   4560
caatcggctg ctctgatgcc gccgtgttcc ggctgtcagc gcaggggcgc ccggttcttt   4620
ttgtcaagac cgacctgtcc ggtgccctga atgaactgca agacgaggca gcgcggctat   4680
cgtggctggc cacgacgggc gttccttgcg cagctgtgct cgacgttgtc actgaagcgg   4740
gaagggactg gctgctattg ggcgaagtgc cggggcagga tctcctgtca tctcaccttg   4800
ctcctgccga gaaagtatcc atcatggctg atgcaatgcg gcggctgcat acgcttgatc   4860
cggctacctg cccattcgac caccaagcga aacatcgcat cgagcgagca cgtactcgga   4920
tggaagccgg tcttgtcgat caggatgatc tggacgaaga gcatcagggg ctcgcgccag   4980
ccgaactgtt cgccaggctc aaggcgagca tgcccgacgg cgaggatctc gtcgtgaccc   5040
atggcgatgc ctgcttgccg aatatcatgg tggaaaatgg ccgcttttct ggattcatcg   5100
actgtggccg gctgggtgtg gcggaccgct atcaggacat agcgttggct acccgtgata   5160
ttgctgaaga gcttggcggc gaatgggctg accgcttcct cgtgctttac ggtatcgccg   5220
ctcccgattc gcagcgcatc gccttctatc gccttcttga cgagttcttc tgaattatta   5280
acgcttacaa tttcctgatg cggtattttc tccttacgca tctgtgcggt atttcacacc   5340
gcatcaggtg gcacttttcg gggaaatgtg cgcggaaccc ctatttgttt atttttctaa   5400
atacattcaa atatgtatcc gctcatgacc aaaatccctt aacgtgagtt ttcgttccac   5460
tgagcgtcag accccgtaga aaagatcaaa ggatcttctt gagatccttt ttttctgcgc   5520
gtaatctgct gcttgcaaac aaaaaaacca ccgctaccag cggtggtttg tttgccggat   5580
caagagctac caactctttt tccgaaggta actggcttca gcagagcgca gataccaaat   5640
actgtccttc tagtgtagcc gtagttaggc caccacttca agaactctgt agcaccgcct   5700
acatacctcg ctctgctaat cctgttacca gtggctgctg ccagtggcga taagtcgtgt   5760
```

cttaccgggt tggactcaag acgatagtta ccggataagg cgcagcggtc gggctgaacg 5820
gggggttcgt gcacacagcc cagcttggag cgaacgacct acaccgaact gagataccta 5880
cagcgtgagc tatgagaaag cgccacgctt cccgaaggga gaaaggcgga caggtatccg 5940
gtaagcggca gggtcggaac aggagagcgc acgagggagc ttccaggggg aaacgcctgg 6000
tatctttata gtcctgtcgg gtttcgccac ctctgacttg agcgtcgatt tttgtgatgc 6060
tcgtcagggg ggcggagcct atggaaaaac gccagcaacg cggccttttt acggttcctg 6120
gccttttgct ggccttttgc tcacatgttc tttcctgcgt tatcccctga ttctgtggat 6180
aaccgtatta ccgcctttga gtgagctgat accgctcgcc gcagccgaac gaccgagcgc 6240
agcgagtcag tgagcgagga agcggaagag cgcccaatac gcaaaccgcc tctccccgcg 6300
cgttggccga ttcattaatg cagctgcgcg ctcgctcgct cactgaggcc gcccgggcaa 6360
agcccgggcg tcgggcgacc tttggtcgcc cggcctcagt gagcgagcga gcgcgcagag 6420
agggagtggc caactccatc actaggggtt ccttgtagtt aatgattaac ccgccatgct 6480
acttatcta 6489

<210> SEQ ID NO 23
<211> LENGTH: 6445
<212> TYPE: DNA
<213> ORGANISM: Homo sapiens

<400> SEQUENCE: 23
gctcggtccg aacatgtgga atccccagtc ccagtgcaca gcagccgggt cctagctatt 60
ggtattgtta gaaggactat ggttgagaat gtgtggggtg gggaaaacca aaaatgcagg 120
ccctggctca gtcaccagga agggggtgct ccgaggcctt tgagggacct gagctcacag 180
aactacagac agcagatcat gaggctcaca ctttctggcc accaagtgcc actctgctgg 240
gcatgtggag tgtgcgtgtg gtgtggtggt aaggatggaa ccaaaagagg aagctgtgta 300
tgtgtacccc catgtgagga ggaagaaaca gaatagaggg tggggttgga ggagagatgt 360
ataaagaccc tcaaagggaa aaataattcc ttttttgtat tcactgactg agctgatgca 420
tttcttattt ggggagcatt ttgggtaata tttaaaaaaa aaaaaaactg tcaagtgatc 480
actgggcacc gaattcgttt ataatcttgt tctaaaccca gcaatttctc ttcttgtgtt 540
ccagaattac cacaacatgc tcgcctggca gcggagggaa aggggcggtg ggcgtcccag 600
tgctcagatc tctcgagtca ggatgagaaa ccagtgataa tgtctgggtt cagggacagc 660
agcaggatgg gagacagatg cataaacatc agggtgttct ctctggtgaa tgagggcttc 720
atgttattaa tgtggtgagt cagtgagccc cactgggtag tggtaaacat gtacaggctg 780
tagagggctg tgaccagcat gttcagtcct gtcaggagca gggtgatgtt gctccaggag 840
aatgttgtca ccagcactga cagctctccc agcaggttaa ttgtaggggg cagagccagg 900
ttggccagac tagccaggag ccaccagaaa gccatcagtg ggagcagggt ctggagcccc 960
tgactcagga tcataattct tgagtgagtt ctttcatagt tgctatttgc caggcagaac 1020
aggaggctgc tggtcagccc atgagcaatc atgaggatca ctgccccagt aaaggaccag 1080
ggtgtctgaa tcagaatggc agtcaccacc agtgccatgt ggctgatgga gctgtaagca 1140
atcaggctct tgaggtcagt ctgcctgaga cagatggagc tggtcatgat catacccccag 1200 aggctcagaa ccaggaaagg gtaagccatg tgctttgtca gagggttcag gatcagggtg 1260
agcctcatca taccataacc acccagcttc aggaggacag cagccaggac catggagcca 1320
gctattggag cttccacatg agccttgggg agccagaggt gcaggccata gaggggcatc 1380
ttcaccataa aggccattgt ataagccagc cacatcaggt tgtttgccca ggagttactc 1440
agctcctggg cagtcagagt cagcaggagg atgttcaggc tacccagtgt gttgtgggta 1500
tagatcagtg caatcagcag gggcagtgag cccaccagtg tataaaagag aaagtaggtg 1560
cctgcattca gcctctcagg ctgatttccc cacctagtga tgatggccag ggttgggatg 1620
agagtggtct caaagaagat atagaacatg atcagctcag tggctgtgaa ggtcataatc 1680
aggctgattt gcaggctaat gagcatggac aggtacagct tttccttgga cagaggctct 1740
gagctgaggt gcctctgact ggccatgata gtcagaggca gcagccatgt ggtcagcatg 1800
agcagggggg ttgtcagggg atcagaggaa aaggtagggg agcatgaaaa gaggttatta 1860
ttaatctggt tgaaaaacag cagtgggatg atgctgataa tcaggctgtg ggttgtggtg 1920
ttaatccaaa tcatgtgctt tttgctcagc catgtgagag gcagcagcat gatggttggc 1980
acaatcagct tcagcatagt cctcctttcc aggtaccaca cactcccccc cacacagcca 2040
gtcaggagcc tggatgacag tgtatggggg ctggcagcca tgtcgactct agaggatccc 2100
cggggaattc aatcgatgtt cgaatcccaa ttctttgcca aagtgatggg ccagcacaca 2160
gaccagcacg ttgcccagga gctgtgggag gaagataaga ggtatgaaca tgattagcaa 2220
aagggcctag cttggactca gaataatcca gccttatccc aaccataaaa taaaagcaga 2280
atggtagctg gattgtagct gctattagca atatgaaacc tcttacatca gttacaattt 2340
atatgcagaa atatttatat gcagaaatat tgctattgcc ttaacccaga aattatcact 2400
gttattcttt agaatggtgc aaagaggcat gatacattgt atcattattg ccctgaaaga 2460
aagagattag ggaaagtatt agaaataaga taaacaaaaa agtatattaa aagaagaaag 2520
catttttttgt gggcctatag actctatagg cggtacttac gtcactcttg gcacggggaa 2580
tccgcgttcc aatgcaccgt tcccggccgg gattcgaatc cgcggaggct ggatcggtcc 2640
cggtgtcttc tatggaggtc aaaacagcgt ggatggcgtc tccaggcgat ctgacggttc 2700
actaaacgag ctctgcttat atagacctcc caccgtacac gcctaccgcc catttgcgtc 2760
aatggggcgg agttgttacg acattttgga aagtcccgtt gattttggtg ccaaaacaaa 2820
ctcccattga cgtcaatggg gtggagactt ggaaatcccc gtgagtcaaa ccgctatcca 2880
cgcccattga tgtactgcca aaaccgcatc accatggtaa tagcgatgac taatacgtag 2940
atgtactgcc aagtaggaaa gtcccataag gtcatgtact gggcataatg ccaggcgggc 3000
catttaccgt cattgacgtc aatagggggc gtacttggca tatgatacac ttgatgtact 3060
gccaagtggg cagtttaccg taaatactcc acccattgac gtcaatggaa agtccctatt 3120
ggcgttacta tgggaacata cgtcattatt gacgtcaatg ggcgggggtc gttgggcggt 3180
cagccaggcg ggccatttac cgtaagttat gtaacgcgga actccatata tgggctatga 3240
actaatgacc ccgtaattga ttactattaa taactagacg cgtgcggccg tagataagta 3300
gcatggcggg ttaatcatta actacaagga acccctagtg atggagttgg ccactccctc 3360
tctgcgcgct cgctcgctca ctgaggccgg gcgaccaaag gtcgcccgac gcccgggctt 3420
tgcccgggcg gcctcagtga gcgagcgagc gcgcagctgg cgtaatagcg aagaggcccg 3480
caccgatcgc ccttcccaac agttgcgcag cctgaatggc gaatggcgat tccgttgcaa 3540
tggctggcgg taatattgtt ctggatatta ccagcaaggc cgatagtttg agttcttcta 3600
ctcaggcaag tgatgttatt actaatcaaa gaagtattgc gacaacggtt aatttgcgtg 3660
atggacagac tcttttactc ggtggcctca ctgattataa aaacacttct caggattctg 3720

```
gcgtaccgtt cctgtctaaa atccctttaa tcggcctcct gtttagctcc cgctctgatt   3780
ctaacgagga aagcacgtta tacgtgctcg tcaaagcaac catagtacgc gccctgtagc   3840
ggcgcattaa gcgcggcggg tgtggtggtt acgcgcagcg tgaccgctac acttgccagc   3900
gccctagcgc ccgctccttt cgctttcttc ccttcctttc tcgccacgtt cgccggcttt   3960
ccccgtcaag ctctaaatcg ggggctccct ttagggttcc gatttagtgc tttacggcac   4020
ctcgacccca aaaaacttga ttagggtgat ggttcacgta gtgggccatc gccctgatag   4080
acggtttttc gccctttgac gttggagtcc acgttcttta atagtggact cttgttccaa   4140
actggaacaa cactcaaccc tatctcggtc tattcttttg atttataagg gattttgccg   4200
atttcggcct attggttaaa aaatgagctg atttaacaaa aatttaacgc gaattttaac   4260
aaaatattaa cgcttacaat ttaggtggca cttttcgggg aaatgtgcgc ggaaccccta   4320
tttgtttatt tttctaaata cattcaaata tgtatccgct catgagacaa taaccctgat   4380
aaatgcttca ataatagcac ctagatcaag agacaggatg aggatcgttt cgcatgattg   4440
aacaagatgg attgcacgca ggttctccgg ccgcttgggt ggagaggcta ttcggctatg   4500
actgggcaca acagacaatc ggctgctctg atgccgccgt gttccggctg tcagcgcagg   4560
ggcgcccggt tctttttgtc aagaccgacc tgtccggtgc cctgaatgaa ctgcaagacg   4620
aggcagcgcg gctatcgtgg ctggccacga cgggcgttcc ttgcgcagct gtgctcgacg   4680
ttgtcactga agcgggaagg gactggctgc tattgggcga agtgccgggg caggatctcc   4740
tgtcatctca ccttgctcct gccgagaaag tatccatcat ggctgatgca atgcggcggc   4800
tgcatacgct tgatccggct acctgcccat tcgaccacca agcgaaacat cgcatcgagc   4860
gagcacgtac tcggatggaa gccggtcttg tcgatcagga tgatctggac gaagagcatc   4920
aggggctcgc gccagccgaa ctgttcgcca ggctcaaggc gagcatgccc gacggcgagg   4980
atctcgtcgt gacccatggc gatgcctgct tgccgaatat catggtggaa aatggccgct   5040
tttctggatt catcgactgt ggccggctgg gtgtggcgga ccgctatcag gacatagcgt   5100
tggctacccg tgatattgct gaagagcttg gcggcgaatg ggctgaccgc ttcctcgtgc   5160
tttacggtat cgccgctccc gattcgcagc gcatcgcctt ctatcgcctt cttgacgagt   5220
tcttctgaat tattaacgct tacaatttcc tgatgcggta ttttctcctt acgcatctgt   5280
gcggtatttc acaccgcatc aggtggcact tttcggggaa atgtgcgcgg aacccctatt   5340
tgtttatttt tctaaataca ttcaaatatg tatccgctca tgaccaaaat cccttaacgt   5400
gagttttcgt tccactgagc gtcagacccc gtagaaaaga tcaaaggatc ttcttgagat   5460
cctttttttc tgcgcgtaat ctgctgcttg caaacaaaaa aaccaccgct accagcggtg   5520
gtttgtttgc cggatcaaga gctaccaact ctttttccga aggtaactgg cttcagcaga   5580
gcgcagatac caaatactgt tcttctagtg tagccgtagt taggccacca cttcaagaac   5640
tctgtagcac cgcctacata cctcgctctg ctaatcctgt taccagtggc tgctgccagt   5700
ggcgataagt cgtgtcttac cgggttggac tcaagacgat agttaccgga taaggcgcag   5760
cggtcgggct gaacgggggg ttcgtgcaca cagcccagct tggagcgaac gacctacacc   5820
gaactgagat acctacagcg tgagctatga gaaagcgcca cgcttcccga agggagaaag   5880
gcggacaggt atccggtaag cggcagggtc ggaacaggag agcgcacgag ggagcttcca   5940
gggggaaacg cctggtatct ttatagtcct gtcgggtttc gccacctctg acttgagcgt   6000
cgatttttgt gatgctcgtc aggggggcgg agcctatgga aaaacgccag caacgcggcc   6060
tttttacggt tcctggcctt ttgctggcct tttgctcaca tgttctttcc tgcgttatcc   6120
```

cctgattctg tggataaccg tattaccgcc tttgagtgag ctgataccgc tcgccgcagc 6180
cgaacgaccg agcgcagcga gtcagtgagc gaggaagcgg aagagcgccc aatacgcaaa 6240
ccgcctctcc ccgcgcgttg gccgattcat taatgcagct gcgcgctcgc tcgctcactg 6300
aggccgcccg ggcaaagccc gggcgtcggg cgacctttgg tcgcccggcc tcagtgagcg 6360
agcgagcgcg cagagaggga gtggccaact ccatcactag gggttccttg tagttaatga 6420
ttaacccgcc atgctactta tctac 6445

<210> SEQ ID NO 24
<211> LENGTH: 398
<212> TYPE: DNA
<213> ORGANISM: Homo sapiens

<400> SEQUENCE: 24
aaaatgcttt cttcttttaa tatacttttt tgtttatctt atttctaata ctttccctaa 60
tctctttctt tcagggcaat aatgatacaa tgtatcatgc ctctttgcac cattctaaag 120
aataacagtg ataatttctg ggttaaggca atagcaatat ttctgcatat aaatatttct 180
gcatataaat tgtaactgat gtaagaggtt tcatattgct aatagcagct acaatccagc 240
taccattctg cttttatttt atggttggga taaggctgga ttattctgag tccaagctag 300
gcccttttgc taatcatgtt catacctctt atcttcctcc cacagctcct gggcaacgtg 360
ctggtctgtg tgctggccca tcactttggc aaagaatt 398

<210> SEQ ID NO 25
<211> LENGTH: 654
<212> TYPE: DNA
<213> ORGANISM: Homo sapiens

<400> SEQUENCE: 25
ctagttatta atagtaatca attacggggt cattagttca tagcccatat atggagttcc 60
gcgttacata acttacggta aatggcccgc ctggctgacc gcccaacgac ccccgcccat 120
tgacgtcaat aatgacgtat gttcccatag taacgccaat agggactttc cattgacgtc 180
aatgggtgga gtatttacgg taaactgccc acttggcagt acatcaagtg tatcatatgc 240
caagtacgcc ccctattgac gtcaatgacg gtaaatggcc cgcctggcat tatgcccagt 300
acatgacctt atgggacttt cctacttggc agtacatcta cgtattagtc atcgctatta 360
ccatggtgat gcggttttgg cagtacatca atgggcgtgg atagcggttt gactcacggg 420
gatttccaag tctccacccc attgacgtca atgggagttt gttttggcac caaaatcaac 480
gggactttcc aaaatgtcgt aacaactccg ccccattgac gcaaatgggc ggtaggcgtg 540
tacggtggga ggtctatata agcagagctc gtttagtgaa ccgtcagatc gcctggagac 600
gccatccacg ctgttttgac ctccatagaa gacaccggga ccgatccagc ctcc 654

<210> SEQ ID NO 26
<211> LENGTH: 128
<212> TYPE: DNA
<213> ORGANISM: Homo sapiens

<400> SEQUENCE: 26
gcgcgctcgc tcgctcactg aggccgcccg ggcaaagccc gggcgtcggg cgacctttgg 60
tcgcccggcc tcagtgagcg agcgagcgcg cagagaggga gtggccaact ccatcactag 120
gggttcct 128

-continued

```
<210> SEQ ID NO 27
<211> LENGTH: 130
<212> TYPE: DNA
<213> ORGANISM: Homo sapiens

<400> SEQUENCE: 27

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag                                                           130
```

RECOMBINANT AAV VECTORS AND METHODS OF USING THE SAME

CLAIM FOR PRIORITY

This is a National Stage Application under 35 U.S.C. § 371 of International Patent Application No. PCT/US2019/036487, filed Jun. 11, 2019, which claims the benefit of U.S. Provisional Application No. 62/683,501, filed Jun. 11, 2018.

This application claims priority to U.S. Application No. 62/683,501 filed Jun. 11, 2018, which is incorporated herein by reference in its entirety.

The present disclosure relates to recombinant adeno-associated virus (AAV) vectors expressing the human ND4 gene, methods of preparing recombinant AAV vectors expressing the human ND4 gene, and uses thereof. Recombinant AAV vectors as disclosed herein are useful in treating Leber Hereditary Optic Neuroretinopathy (LHON), including ND4-related LHON.

BACKGROUND OF THE DISCLOSURE

Leber Hereditary Optic Neuroretinopathy (LHON), also known as "Leber Hereditary Optic Neuropathy," or "Leber Hereditary Optic Atrophy," is an optic nerve dysfunction that manifests as bilateral, acute or subacute loss of central vision due to degeneration of retinal ganglion cells. LHON is linked to point mutations in the mitochondrial DNA (mtDNA), which is inherited maternally (Orssaud, C., *Orphanet Encyclopedia*, http://www.orpha.net/data/patho/GB/uk-LHON.pdf, 2003). The most common mtDNA point mutations that are associated with LHON are G3460A/ND1, G11778A/ND4 and T14484C/ND6. These mutations are linked with defects of subunits of the complex I (NADH-dehydrogenase-ubiquinone reductase) in mitochondria.

The G11778A mitochondrial DNA point mutation in the NADH. dehydrogenase 4 gene (ND4 gene) leads to the production of a misfolded protein that alters mitochondrial complex I activity and reduces oxidative phosphorylation (Baracca, et al., *Arch. Neurol.*, 62, pp. 730-736 (2005)). This results in a reduced production of ATP and an increased generation of reactive oxygen species, and leads to the death of retinal ganglion cells (RGCs) (Perier et al., *Proc Natl Acad Sci USA,* 102, pp. 19126-19131 (2005); Qi et al., *Arch. Ophthalmol.,* 125, pp. 268-272 (2007)). The G11778A mitochondrial DNA point mutation is manifested by a severe visual impairment.

LHON lends itself to gene therapies, including the use of viral vectors, e.g., recombinant adeno-associated viral vectors (AAV), such as serotype 2 (recombinant AAV2 vectors). In some instances, the use of recombinant AAV vectors permits the transfer of recombinant DNA into retinal ganglion cells of the fovea and perifovea in humans. The transfer of cDNA coding for mitochondrial ND4 provides an ND4 protein that localizes to complex I of the mitochondria.

In some instances, while not wishing to be bound by theory, recombinant AAV2 vectors expressing the ND4 gene can exert biological activity by virtue of their ability, e.g., to (1) reach the nucleus of a target cell through internalization into the cytoplasm (via endocytosis) and nuclear import via binding of the AAV2 particle with nucleolin (nuclear shuttle protein), (2) form intranuclear episomes transcribing ND4 mRNA coding a functional NADH dehydrogenase 4 protein, and (3) target ND4 mRNA toward mitochondria by virtue of a mitochondrial targeting sequence (MTS) to allow ND4 protein expression into mitochondria (U.S. Pat. No. 9,017,999).

SUMMARY OF THE DISCLOSURE

In some aspects, the present disclosure relates to the following embodiments:

1. A recombinant AAV2 vector comprising:
a 3'UTR Cox10 sequence comprising SEQ ID No: 1,
a nucleic acid sequence encoding an NADH dehydrogenase 4 (ND4) polypeptide comprising SEQ ID No: 13, and
a nucleic acid sequence encoding an MTS Cox10 polypeptide comprising SEQ ID No: 11.

2. A recombinant AAV2 vector comprising:
a 3'UTR Cox10 sequence comprising SEQ ID No: 1,
a nucleic acid sequence encoding an NADH dehydrogenase 4 (ND4) polypeptide comprising SEQ ID No: 13, and
a nucleic acid sequence encoding an MTS Cox10 polypeptide comprising SEQ ID No: 12.

3. A recombinant AAV2 vector comprising:
a 3'UTR Cox10 sequence comprising SEQ ID No: 14,
a nucleic acid sequence encoding an NADH dehydrogenase 4 (ND4) polypeptide comprising SEQ ID No: 13, and
a nucleic acid sequence encoding an MTS Cox10 polypeptide comprising SEQ ID No: 11.

4. A recombinant AAV2 vector comprising:
a 3'UTR Cox10 sequence comprising SEQ ID No: 14,
a nucleic acid sequence encoding an NADH dehydrogenase 4 (ND4) polypeptide comprising SEQ ID No: 13, and
a nucleic acid sequence encoding an MTS Cox10 polypeptide comprising SEQ ID No: 12.

5. A recombinant AAV2 vector comprising:
a 3'UTR Cox10 sequence comprising SEQ ID No: 1,
a sequence encoding ND4 comprising SEQ ID No: 2, and
an MTS Cox10 sequence comprising SEQ ID No: 3.

6. A recombinant AAV2 vector comprising:
a 3'UTR Cox10 sequence consisting of SEQ ID No: 1,
a sequence encoding ND4 consisting of SEQ ID No: 2, and
an MTS Cox10 sequence consisting of SEQ ID No: 3.

7. A recombinant AAV2 vector comprising:
a 3'UTR Cox10 sequence comprising SEQ ID No: 1,
a sequence encoding ND4 comprising SEQ ID No: 17, and
an MTS Cox10 sequence comprising SEQ ID No: 3.

8. A recombinant AAV2 vector comprising:
a 3'UTR Cox10 sequence consisting of SEQ ID No: 1,
a sequence encoding ND4 consisting of SEQ ID No: 17, and
an MTS Cox10 sequence consisting of SEQ ID No: 3.

9. A recombinant AAV2 vector comprising:
a 3'UTR Cox10 sequence comprising SEQ ID No: 14,
a sequence encoding ND4 comprising SEQ ID No: 15, and
an MTS Cox10 sequence comprising SEQ ID No: 16.

10. A recombinant AAV2 vector comprising:
a 3'UTR Cox10 sequence consisting of SEQ ID No: 14,
a sequence encoding ND4 consisting of SEQ ID No: 15, and
an MTS Cox10 sequence consisting of SEQ ID No: 16.

11.A recombinant AAV2 vector comprising:
a 3'UTR Cox10 sequence comprising SEQ ID No: 14,
a sequence encoding ND4 comprising SEQ ID No: 18, and
an MTS Cox10 sequence comprising SEQ ID No: 16.

12.A recombinant AAV2 vector comprising:
a 3'UTR Cox10 sequence consisting of SEQ ID No: 14,
a sequence encoding ND4 consisting of SEQ ID No: 18, and
an MTS Cox10 sequence consisting of SEQ ID No: 16.

13. The recombinant AAV2 vector of any one of embodiments 1-2 or 5-8, further comprising:
an HBB2 intron sequence comprising SEQ ID No: 4,
a CMV promoter sequence comprising SEQ ID No: 5,
a first ITR sequence comprising SEQ ID No: 6, and
a second ITR sequence comprising SEQ ID No: 7.

14. The recombinant AAV2 vector of any one of embodiments 1-2 or 5-8, further comprising:
an HBB2 intron sequence consisting of SEQ ID No: 4,
a CMV promoter sequence consisting of SEQ ID No: 5,
a first ITR sequence consisting of SEQ ID No: 6, and
a second ITR sequence consisting of SEQ ID No: 7.

15. The recombinant AAV2 vector of any one of embodiments 3-4 or 9-12, further comprising:
an HBB2 intron sequence comprising SEQ ID No: 24,
a CMV promoter sequence comprising SEQ ID No: 25,
a first ITR sequence comprising SEQ ID No: 26, and
a second ITR sequence comprising SEQ ID No: 27.

16. The recombinant AAV2 vector of any one of embodiments 3-4 or 9-12, further comprising:
an HBB2 intron sequence consisting of SEQ ID No: 24,
a CMV promoter sequence consisting of SEQ ID No: 25,
a first ITR sequence consisting of SEQ ID No: 26, and
a second ITR sequence consisting of SEQ ID No: 27.

17.A recombinant AAV2 vector comprising:
a 3'UTR Cox10 sequence comprising SEQ ID No: 1,
a sequence encoding ND4 comprising SEQ ID No: 17, and
an MTS Cox10 sequence comprising SEQ ID No: 3,
an HBB2 intron sequence consisting of SEQ ID No: 4,
a CMV promoter sequence consisting of SEQ ID No: 5,
a first ITR sequence consisting of SEQ ID No: 6, and
a second ITR sequence consisting of SEQ ID No: 7.

18.A recombinant AAV2 vector comprising:
a 3'UTR Cox10 sequence comprising SEQ ID No: 14,
a sequence encoding ND4 comprising SEQ ID No: 18, and
an MTS Cox10 sequence comprising SEQ ID No: 16,
an HBB2 intron sequence consisting of SEQ ID No: 24,
a CMV promoter sequence consisting of SEQ ID No: 25,
a first ITR sequence consisting of SEQ ID No: 26, and
a second ITR sequence consisting of SEQ ID No: 27.

19.A method of treating Leber Hereditary Optic Neuroretinopathy in a patient in need thereof, comprising administering to the patient an effective amount of the recombinant AAV2 vector according to any one of embodiments 1-18.

20.A method of treating Leber Hereditary Optic Neuroretinopathy in a patient in need thereof, comprising administering to the patient an effective amount of the recombinant vector according to any one of embodiments 1-18, wherein the patient has experienced a disease duration of less than nine months.

21.A method of treating Leber Hereditary Optic Neuroretinopathy in a patient in need thereof, comprising administering to the patient an effective amount of the recombinant AAV2 vector according to any one of embodiments 1-18, wherein the patient has experienced a disease duration of six to nine months.

22.A method of treating Leber Hereditary Optic Neuroretinopathy in a patient in need thereof, comprising administering to the patient an effective amount of the recombinant AAV2 vector according to any one of embodiments 1-18, wherein the patient has a baseline visual acuity of <about 1.6 LogMAR.

23. A method of treating Leber Hereditary Optic Neuroretinopathy in a patient in need thereof, comprising administering to the patient an effective amount of the recombinant AAV2 vector according to any one of embodiments 1-18, wherein the patient has experienced a disease duration of less than nine months and the patient has a baseline visual acuity of <about 1.6 LogMAR.

24.A method of treating Leber Hereditary Optic Neuroretinopathy in a patient in need thereof, comprising administering to the patient an effective amount of the recombinant AAV2 vector according to any one of embodiments 1-18, wherein the patient has experienced a disease duration of six to nine months and the patient has a baseline visual acuity of <about 1.6 LogMAR.

25. The method according to any one of embodiments 19-24, wherein the Leber Hereditary Optic Neuroretinopathy is ND4-related Leber Hereditary Optic Neuroretinopathy.

26. The method according to any one of embodiments 19-25, wherein the recombinant AAV2 vector is administered intravitreally.

27. The method according to any one of embodiments 19-26, wherein the recombinant AAV2 vector is administered intravitreally in an amount of about $10^9$ to $10^{11}$ viral genomes per eye.

28. The method according to any one of embodiments 19-27, wherein the recombinant AAV2 vector is administered intravitreally in an amount of about $10^{10}$ to $10^{11}$ viral genomes per eye.

29. The method according to any one of embodiments 19-28, wherein the recombinant AAV2 vector is administered intravitreally in an amount of about $5.0\times10^{10}$ to $1.0\times10^{11}$ viral genomes per eye.

30. The method according to any one of embodiments 19-29, wherein the recombinant AAV2 vector is administered intravitreally in an amount of about $9.0\times10^{10}$ viral genomes per eye.

31.A pAAV-ND4 transfer plasmid comprising:
a 3'UTR Cox10 sequence comprising SEQ ID NO: 1,
a coding sequence ND4 comprising SEQ ID NO: 2,
an MTS Cox10 sequence comprising SEQ ID NO: 3,
an HBB2 intron sequence comprising SEQ ID NO: 4,
a CMV promoter sequence comprising SEQ ID NO: 5,
an ITR sequence comprising SEQ ID NO: 6, and
an ITR sequence comprising SEQ ID NO: 7.

32.A pAAV-ND4 transfer plasmid comprising:
a 3'UTR Cox10 sequence comprising SEQ ID NO: 1,
a coding sequence ND4 comprising SEQ ID NO: 17,
an MTS Cox10 sequence comprising SEQ ID NO: 3,
an HBB2 intron sequence comprising SEQ ID NO: 4,
a CMV promoter sequence comprising SEQ ID NO: 5,
an ITR sequence comprising SEQ ID NO: 6, and
an ITR sequence comprising SEQ ID NO: 7.

33. The pAAV-ND4 transfer plasmid of embodiment 31 or 32, further comprising:
an f1 origin of replication sequence comprising SEQ ID NO: 8,
a Kanamycin resistance gene sequence comprising SEQ ID NO: 9, and a ColE1 origin of replication sequence comprising SEQ ID NO: 10.

34.A pAAV-ND4 transfer plasmid comprising:
a 3'UTR Cox10 sequence consisting of SEQ ID NO: 1,
a coding sequence ND4 consisting of SEQ ID NO: 2,
an MTS Cox10 sequence consisting of SEQ ID NO: 3,
an HBB2 intron sequence consisting of SEQ ID NO: 4,
a CMV promoter sequence consisting of SEQ ID NO: 5,
an ITR sequence consisting of SEQ ID NO: 6, and
an ITR sequence consisting of SEQ ID NO: 7.

35.A pAAV-ND4 transfer plasmid comprising:
a 3'UTR Cox10 sequence consisting of SEQ ID NO: 1,
a coding sequence ND4 consisting of SEQ ID NO: 17,
an MTS Cox10 sequence consisting of SEQ ID NO: 3,
an HBB2 intron sequence consisting of SEQ ID NO: 4,
a CMV promoter sequence consisting of SEQ ID NO: 5,
an ITR sequence consisting of SEQ ID NO: 6, and
an ITR sequence consisting of SEQ ID NO: 7.

36. The pAAV-ND4 transfer plasmid of embodiment 34 or 35, further comprising:
an f1 origin of replication sequence consisting of SEQ ID NO: 8,
a Kanamycin resistance gene sequence consisting of SEQ ID NO: 9, and
a ColE1 origin of replication sequence consisting of SEQ ID NO: 10.

37. A pAAV-ND4 transfer plasmid comprising SEQ ID NO: 22.

38.A pAAV-ND4 transfer plasmid comprising SEQ ID NO: 23.

39. A method of preparing the recombinant AAV2 vector according to any one of embodiments 1-18, comprising tri-transfecting in a packaging cell line:
(i) a pAAV-ND4 transfer plasmid according to any one of embodiments 31-38;
(ii) a rep/cap plasmid, and
(iii) an adenovirus helper plasmid.

40. The method according to embodiment 39, wherein the packaging cell line comprises the human embryonic kidney 293 (HEK 293) cell line.

41. The method according to embodiment 38 or 40, wherein the rep/cap plasmid is pRep2Cap2 plasmid.

42. The method according to any one of embodiments 38-41, wherein the adenovirus helper plasmid is pXX6 plasmid.

BRIEF DESCRIPTION OF THE DRAWINGS

The accompanying drawings, which are incorporated in and constitute a part of this specification, illustrate several non-limiting embodiments of the present disclosure and together with the description, serve to explain the principles of the disclosure.

DETAILED DESCRIPTION OF THE DISCLOSURE

Figure 1:
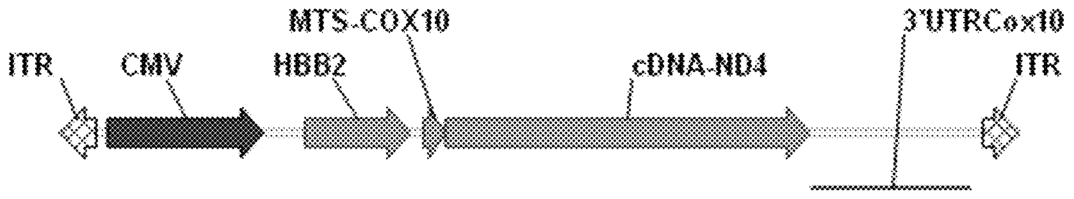
FIG. 1 depicts an embodiment of a recombinant AAV2 vector of the disclosure comprising inverted terminal repeats (ITRs), a cytomegalovirus immediate early promoter (CMV) in an intron-containing expression cassette (beta globin intron, HBB2), an MTS Cox10 sequence, a coding sequence ND4, and a 3'UTR Cox10 sequence.

Disclosed herein in some embodiments are recombinant vectors expressing a gene encoding the human NADH dehydrogenase type 4 (ND4) protein ND4 (SEQ ID NO: 13). Also disclosed herein are methods of treating LHON by administration of recombinant AAV2 vectors expressing the human ND4 protein.

The term "a," "an," or "the" refers to one or to more than one of the grammatical object of the article. The term may mean "one," "one or more," "at least one," or "one or more than one." By way of example, "an element" means one element or more than one element. The term "or" means "and/or" unless otherwise stated. The term "including" or "containing" is not limiting.

The term "codon" is meant to refer to a sequence of three nucleotides, e.g., deoxyribonucleotides or ribonucleotides, which together form a unit of a genetic code that encodes an amino acid. The term "genetic code" is meant to refer to the full set of relationships between codons and amino acids used by living cells. The genetic code is highly similar among all organisms, and a person of ordinary skill in the art would understand that the terms "universal genetic code" or "standard genetic code" is meant to refer to the most common genetic code, used by most organisms including humans. In some embodiments, the universal genetic code is the genetic code used in eukaryotic cells. In some embodiments, the universal genetic code is the genetic code for nuclear genes. The term "mitochondria genetic code" is meant to refer to the code used in mitochondria, that sets out the codes for mitochondria nucleic acids and proteins. In some embodiments, the mitochondria genetic code is the vertebrate mitochondria code. In some embodiments, the mitochondria genetic code is the human mitochondria code. Codon usage in the mitochondria vs. the universal genetic code is described in Lewin, Genes V, Oxford University Press; New York 1994, the content of which is incorporated by reference.

The human NADH dehydrogenase type 4 (ND4) protein is a subunit of NADH dehydrogenase (ubiquinone), which is targeted to the mitochondrial inner membrane, and is the largest of the five complexes of the electron transport chain. The ND4 gene, also known as mitochondrially encoded NADH dehydrogenase 4 (MT-ND4), is located in the human mitochondria DNA. Exemplary nucleic acid sequences encoding the ND4 protein include but are not limited to NCBI NC_012920.1. In some embodiments, the nucleic acid sequence encoding an ND4 polypeptide may be a mitochondrial nucleic acid, or a nuclear nucleic acid encoding for the human ND4 polypeptide. In some embodiments, the nucleic acid sequence encoding an ND4 polypeptide may be any nucleic acid sequence encoding a human ND4 polypeptide.

In some embodiments, the nucleic acid sequence encoding a human ND4 protein comprises SEQ ID NO: 2, 15, 17 or 18. Exemplary amino acid sequences for the human ND4 polypeptide include but are not limited to Genbank ACF70814.1. In some embodiments, the amino acid sequence of the human ND4 polypeptide comprises SEQ ID NO: 13.

TABLE 1

| Sequences of various embodiments of the disclosure | | | |
|---|---|---|---|
| SEQ ID NO: 2 | ND4<br>(3' to 5') | 1374<br>nt | ATGAGAAACCAGTGATAATGTCTGGGTTCAGGGACAGCAGCA<br>GGATGGGAGACAGATGCATAAACATCAGGGTGTTCTCTCTGGT<br>GAATGAGGGCTTCATGTTATTAATGTGGTGAGTCAGTGAGCCC<br>CACTGGGTAGTGGTAAACATGTACAGGCTGTAGAGGGCTGTG<br>ACCAGCATGTTCAGTCCTGTCAGGAGCAGGGTGATGTTGCTC<br>CAGGAGAATGTTGTCACCAGCACTGACAGCTCTCCCAGCAGG<br>TTAATTGTAGGGGGCAGAGCCAGGTTGGCCAGACTAGCCAGG<br>AGCCACCAGAAAGCCATCAGTGGGAGCAGGGTCTGGAGCCCC<br>TGACTCAGGATCATAATTCTTGAGTGAGTTCTTTCATAGTTGCT<br>ATTTGCCAGGCAGAACAGGAGGCTGCTGGTCAGCCCATGAGC<br>AATCATGAGGATCACTGCCCCAGTAAAGGACCAGGGTGTCTG<br>AATCAGAATGGCAGTCACCACCAGTGCCATGTGGCTGATGGA<br>GCTGTAAGCAATCAGGCTCTTGAGGTCAGTCTGCCTGAGACA<br>GATGGAGCTGGTCATGATCATACCCCAGAGGCTCAGAACCAG<br>GAAAGGGTAAGCCATGTGCTTTGTCAGAGGGTTCAGGATCAG<br>GGTGAGCCTCATCATACCATAACCACCCAGCTTCAGGAGGACA<br>GCAGCCAGGACCATGGAGCCAGCTATTGGAGCTTCCACATGA<br>GCCTTGGGGAGCCAGAGGTGCAGGCCATAGAGGGGCATCTTC<br>ACCATAAAGGCCATTGTATAAGCCAGCCACATCAGGTTGTTTG<br>CCCAGGAGTTACTCAGCTCCTGGGCAGTCAGAGTCAGCAGGA<br>GGATGTTCAGGCTACCCAGTGTGTTGTGGGTATAGATCAGTGC<br>AATCAGCAGGGGCAGTGAGCCCACCAGTGTATAAAAGAGAAA<br>GTAGGTGCCTGCATTCAGCCTCTCAGGCTGATTTCCCCACCTA<br>GTGATGATGGCCAGGGTTGGGATGAGAGTGGTCTCAAAGAAG<br>ATATAGAACATGATCAGCTCAGTGGCTGTGAAGGTCATAATCA<br>GGCTGATTTGCAGGCTAATGAGCATGGACAGGTACAGCTTTTT<br>CCTTGACAGAGGCTCTGAGCTGAGGTGCCTCTGACTGGCCAT<br>GATAGTCAGAGGCAGCAGCCATGTGGTCAGCATGAGCAGGGG<br>GGTTGTCAGGGGATCAGAGGAAAAGGTAGGGGAGCATGAAAA<br>GAGGTTATTATTAATCTGGTTGAAAAACAGCAGTGGGATGATG<br>CTGATAATCAGGCTGTGGGTTGTGGTGTTAATCCAAATCATGT<br>GCTTTTTGCTCAGCCATGTGAGAGGCAGCAGCATGATGGTTG<br>GCACAATCAGCTTCAGCA |
| SEQ ID NO: 17 | ND4<br>(3' to 5') | 1380<br>nt | TCAGGATGAGAAACCAGTGATAATGTCTGGGTTCAGGGACAG<br>CAGCAGGATGGGAGACAGATGCATAAACATCAGGGTGTTCTCT<br>CTGGTGAATGAGGGCTTCATGTTATTAATGTGGTGAGTCAGTG<br>AGCCCCACTGGGTAGTGGTAAACATGTACAGGCTGTAGAGGG<br>CTGTGACCAGCATGTTCAGTCCTGTCAGGAGCAGGGTGATGTT<br>GCTCCAGGAGAATGTTGTCACCAGCACTGACAGCTCTCCCAG<br>CAGGTTAATTGTAGGGGGCAGAGCCAGGTTGGCCAGACTAGC<br>CAGGAGCCACCAGAAAGCCATCAGTGGGAGCAGGGTCTGGA<br>GCCCCTGACTCAGGATCATAATTCTTGAGTGAGTTCTTTCATAG<br>TTGCTATTTGCCAGGCAGAACAGGAGGCTGCTGGTCAGCCCA<br>TGAGCAATCATGAGGATCACTGCCCCAGTAAAGGACCAGGGT<br>GTCTGAATCAGAATGGCAGTCACCACCAGTGCCATGTGGCTG<br>ATGGAGCTGTAAGCAATCAGGCTCTTGAGGTCAGTCTGCCTGA<br>GACAGATGGAGCTGGTCATGATCATACCCCAGAGGCTCAGAA<br>CCAGGAAAGGGTAAGCCATGTGCTTTGTCAGAGGGTTCAGGA<br>TCAGGGTGAGCCTCATCATACCATAACCACCCAGCTTCAGGAG<br>GACAGCAGCCAGGACCATGGAGCCAGCTATTGGAGCTTCCAC<br>ATGAGCCTTGGGGAGCCAGAGGTGCAGGCCATAGAGGGGCA<br>TCTTCACCATAAAGGCCATTGTATAAGCCAGCCACATCAGGTT<br>GTTTGCCCAGGAGTTACTCAGCTCCTGGGCAGTCAGAGTCAG<br>CAGGAGGATGTTCAGGCTACCCAGTGTGTTGTGGGTATAGATC<br>AGTGCAATCAGCAGGGGCAGTGAGCCCACCAGTGTATAAAAG<br>AGAAAGTAGGTGCCTGCATTCAGCCTCTCAGGCTGATTTCCCC<br>ACCTAGTGATGATGGCCAGGGTTGGGATGAGAGTGGTCTCAA<br>AGAAGATATAGAACATGATCAGCTCAGTGGCTGTGAAGGTCAT<br>AATCAGGCTGATTTGCAGGCTAATGAGCATGGACAGGTACAGC<br>TTTTTCCTTGACAGAGGCTCTGAGCTGAGGTGCCTCTGACTGG<br>CCATGATAGTCAGAGGCAGCAGCCATGTGGTCAGCATGAGCA<br>GGGGGGTTGTCAGGGGATCAGAGGAAAAGGTAGGGGAGCAT<br>GAAAAGAGGTTATTATTAATCTGGTTGAAAAACAGCAGTGGGA<br>TGATGCTGATAATCAGGCTGTGGGTTGTGGTGTTAATCCAAAT<br>CATGTGCTTTTTGCTCAGCCATGTGAGAGGCAGCAGCATGATG<br>GTTGGCACAATCAGCTTCAGCAT |
| SEQ ID NO: 15 | ND4<br>(5' to 3') | 1374<br>nt | TGCTGAAGCTGATTGTGCCAACCATCATGCTGCTGCCTCTCAC<br>ATGGCTGAGCAAAAAGCACATGATTTGGATTAACACCACAACC<br>CACAGCCTGATTATCAGCATCATCCCACTGCTGTTTTTCAACCA<br>GATTAATAATAACCTCTTTTCATGCTCCCCTACCTTTTCCTCTG<br>ATCCCCTGACAACCCCCCTGCTCATGCTGACCACATGGCTGCT<br>GCCTCTGACTATCATGGCCAGTCAGAGGCACCTCAGCTCAGA<br>GCCTCTGTCAAGGAAAAAGCTGTACCTGTCCATGCTCATTAGC<br>CTGCAAATCAGCCTGATTATGACCTTCACAGCCACTGAGCTGA<br>TCATGTTCTATATCTTCTTTGAGACCACTCTCATCCCAACCCTG<br>GCCATCATCACTAGGTGGGGAAATCAGCCTGAGAGGCTGAAT |

TABLE 1-continued

| Sequences of various embodiments of the disclosure | | | |
|---|---|---|---|
| | | | GCAGGCACCTACTTTCTCTTTTATACACTGGTGGGCTCACTGC<br>CCCTGCTGATTGCACTGATCTATACCCACAACACACTGGGTAG<br>CCTGAACATCCTCCTGCTGACTCTGACTGCCCAGGAGCTGAGT<br>AACTCCTGGGCAAACAACCTGATGTGGCTGGCTTATACAATGG<br>CCTTTATGGTGAAGATGCCCCTCTATGGCCTGCACCTCTGGCT<br>CCCCAAGGCTCATGTGGAAGCTCCAATAGCTGGCTCCATGGT<br>CCTGGCTGCTGTCCTCCTGAAGCTGGGTGGTTATGGTATGATG<br>AGGCTCACCCTGATCCTGAACCCTCTGACAAAGCACATGGCTT<br>ACCCTTTCCTGGTTCTGAGCCTCTGGGGTATGATCATGACCAG<br>CTCCATCTGTCTCAGGCAGACTGACCTCAAGAGCCTGATTGCT<br>TACAGCTCCATCAGCCACATGGCACTGGTGGTGACTGCCATTC<br>TGATTCAGACACCCTGGTCCTTTACTGGGGCAGTGATCCTCAT<br>GATTGCTCATGGGCTGACCAGCAGCCTCCTGTTCTGCCTGGC<br>AAATAGCAACTATGAAAGAACTCACTCAAGAATTATGATCCTGA<br>GTCAGGGGCTCCAGACCCTGCTCCCACTGATGGCTTTCTGGT<br>GGCTCCTGGCTAGTCTGGCCAACCTGGCTCTGCCCCCTACAA<br>TTAACCTGCTGGGAGAGCTGTCAGTGCTGGTGACAACATTCTC<br>CTGGAGCAACATCACCCTGCTCCTGACAGGACTGAACATGCT<br>GGTCACAGCCCTCTACAGCCTGTACATGTTTACCACTACCCAG<br>TGGGGCTCACTGACTCACCACATTAATAACATGAAGCCCTCAT<br>TCACCAGAGAGAACACCCTGATGTTTATGCATCTGTCTCCCAT<br>CCTGCTGCTGTCCCTGAACCCAGACATTATCACTGGTTTCTCA<br>T |
| SEQ ID NO: 18 | ND4<br>(5' to 3') | 1380<br>nt | ATGCTGAAGCTGATTGTGCCAACCATCATGCTGCTGCCTCTCA<br>CATGGCTGAGCAAAAAGCACATGATTTGGATTAACACCACAAC<br>CCACAGCCTGATTATCAGCATCATCCCACTGCTGTTTTTCAACC<br>AGATTAATAATAACCTCTTTTCATGCTCCCCTACCTTTTCCTCT<br>GATCCCCTGACAACCCCCCTGCTCATGCTGACCACATGGCTG<br>CTGCCTCTGACTATCATGGCCAGTCAGAGGCACCTCAGCTCA<br>GAGCCTCTGTCAAGGAAAAAGCTGTACCTGTCCATGCTCATTA<br>GCCTGCAAATCAGCCTGATTATGACCTTCACAGCCACTGAGCT<br>GATCATGTTCTATATCTTCTTTGAGACCACTCTCATCCCAACCC<br>TGGCCATCATCACTAGGTGGGGAAATCAGCCTGAGAGGCTGA<br>ATGCAGGCACCTACTTTCTCTTTTATACACTGGTGGGCTCACT<br>GCCCCTGCTGATTGCACTGATCTATACCCACAACACACTGGGT<br>AGCCTGAACATCCTCCTGCTGACTCTGACTGCCCAGGAGCTG<br>AGTAACTCCTGGGCAAACAACCTGATGTGGCTGGCTTATACAA<br>TGGCCTTTATGGTGAAGATGCCCCTCTATGGCCTGCACCTCTG<br>GCTCCCCAAGGCTCATGTGGAAGCTCCAATAGCTGGCTCCAT<br>GGTCCTGGCTGCTGTCCTCCTGAAGCTGGGTGGTTATGGTAT<br>GATGAGGCTCACCCTGATCCTGAACCCTCTGACAAAGCACATG<br>GCTTACCCTTTCCTGGTTCTGAGCCTCTGGGGTATGATCATGA<br>CCAGCTCCATCTGTCTCAGGCAGACTGACCTCAAGAGCCTGAT<br>TGCTTACAGCTCCATCAGCCACATGGCACTGGTGGTGACTGC<br>CATTCTGATTCAGACACCCTGGTCCTTTACTGGGGCAGTGATC<br>CTCATGATTGCTCATGGGCTGACCAGCAGCCTCCTGTTCTGCC<br>TGGCAAATAGCAACTATGAAAGAACTCACTCAAGAATTATGATC<br>CTGAGTCAGGGGCTCCAGACCCTGCTCCCACTGATGGCTTTC<br>TGGTGGCTCCTGGCTAGTCTGGCCAACCTGGCTCTGCCCCCT<br>ACAATTAACCTGCTGGGAGAGCTGTCAGTGCTGGTGACAACAT<br>TCTCCTGGAGCAACATCACCCTGCTCCTGACAGGACTGAACAT<br>GCTGGTCACAGCCCTCTACAGCCTGTACATGTTTACCACTACC<br>CAGTGGGGCTCACTGACTCACCACATTAATAACATGAAGCCCT<br>CATTCACCAGAGAGAACACCCTGATGTTTATGCATCTGTCTCC<br>CATCCTGCTGCTGTCCCTGAACCCAGACATTATCACTGGTTTC<br>TCATCCTGA |
| SEQ ID NO: 13 | ND4 | 459<br>AA | MLKLIVPTIMLLPLTWLSKKHMIWINTTTHSLIISIIPLLFFNQINNNLF<br>SCSPTFSSDPLTTPLLMLTTWLLPLTIMASQRHLSSEPLSRKKLYL<br>SMLISLQISLIMTFTATELIMFYIFFETTLIPTLAIITRWGNQPERLNA<br>GTYFLFYTLVGSLPLLIALIYTHNTLGSLNILLLTLTAQELSNSWANN<br>LMWLAYTMAFMVKMPLYGLHLWLPKAHVEAPIAGSMVLAAVLLKL<br>GGYGMMRLTLILNPLTKHMAYPFLVLSLWGMIMTSSICLRQTDLK<br>SLIAYSSISHMALVVTAILIQTPWSFTGAVILMIAHGLTSSLLFCLAN<br>SNYERTHSRIMILSQGLQTLLPLMAFWWLLASLANLALPPTINLLG<br>ELSVLVTTFSWSNITLLLTGLNMLVTALYSLYMFTTTQWGSLTHHI<br>NNMKPSFTRENTLMFMHLSPILLLSLNPDIITGFSS |

Without being bound by theory, mitochondrial genes may use a mitochondrial genetic code which is different from the universal genetic code used by nuclear genes. When a mitochondrial gene is inserted in a recombinant vector to be expressed in the nucleus, the mitochondrial nucleic acid sequence may be recoded in accordance with the universal genetic code, in order to be correctly expressed and/or translated outside the mitochondria. In some embodiments, a mitochondria-encoded gene may be recoded to form a nuclear-encoded version of the same gene. In some embodiments, the nuclear-encoded version is produced by codon substitution of the mitochondrial nucleic acid. In some embodiments, the nuclear-encoded version is produced by codon substitution to replace the codons of the mitochondrial genetic code with codons of the universal genetic code. Codon usage in the mitochondria vs. the universal genetic code is described in Lewin, Genes V, Oxford University Press; New York 1994, the content of which is incorporated by reference. Exemplary codon substitutions include but are not limited to UGA to UGG, AGA to UAA, UAG or UGA, AGG to UAA, UAG or UGA, AUA to AUG, CUG or GUG, AUU to AUG, CUG or GUG. In some embodiments, the nucleic acid encoding a human ND4 polypeptide is the sequence of a naturally occurring mitochondrial nucleic acid, recoded in accordance with the universal genetic code.

Due to the degeneracy of the genetic code, most amino acids can be encoded by multiple synonymous codons (Grantham et al., Nucleic Acids Res., 8 (1): 49-r62 (1980). Without being bound by theory, synonymous codons naturally occur with different frequencies in different organisms. The choice of codons may affect protein expression, structure, and function. When expressing a recombinant protein, one may select specific codons to optimize for expression in a chosen host system, thus recoding by taking into account the preferred codon usage. In some embodiments, recoding is done taking into account the preferred usage codon of mammalian cells. In some embodiments, recoding is done taking into account the preferred codon usage in humans.

In some embodiments, the nucleic acid sequence encoding a human ND4 protein, recoded in accordance with the universal genetic code, and taking into account the human preferred usage codon comprises the nucleic acid sequence SEQ ID NO: 2 (3' to 5' sequence) or its reverse complement SEQ ID NO: 15 (5' to 3' sequence).

ID NO: 17 (3' to 5' sequence) or its reverse complement SEQ ID NO: 18 (5' to 3' sequence).

The term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors. In some embodiments, the vector is a DNA vector. In some embodiments, the vector is a circular vector. In some embodiments, the vector is a plasmid. In some embodiments, the vector is double-stranded. In some embodiments, the vector is single-stranded.

In some embodiment, the recombinant vector disclosed herein is a recombinant viral vector. In some embodiments, the viral vector is an adeno-associated viral (AAV) vector, chimeric AAV vector, adenoviral vector, retroviral vector, lentiviral vector, DNA viral vector, herpes simplex viral vector, baculoviral vector, or any mutant or derivative thereof. In some embodiments, the recombinant viral vector is a recombinant adeno-associated virus (AAV) vector. In some embodiments, by an "AAV vector" is meant a vector derived from an adeno-associated virus serotype, including without limitation, AAV-1, AAV-2, AAV-3, AAV-4, AAV-5, AAV-6, AAV-7, AAV-8 and AAV-9. AAV vectors can have one or more of the AAV wild-type genes deleted in whole or part, e.g., the rep and/or cap genes, while retaining functional flanking inverted terminal repeat (ITR) sequences. Functional ITR sequences are necessary for the rescue, replication and packaging of the AAV virion. Thus, an AAV vector is defined herein to include at least those sequences that in cis provide for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. An "AAV vector" may also refer to the protein shell or capsid, which provides an efficient vehicle for delivery of vector nucleic acid to the nucleus of target cells. In some embodiments, the recombinant viral vector is a recombinant AAV2 vector. In some embodiments, a recombinant vector of the disclosure is a recombinant AAV vector, of serotype 2 (rAAV2/2).

In some embodiments, a recombinant AAV vector disclosed herein comprises a nucleic acid sequence encoding the ND4 protein, and operatively linked gene regulatory control sequences, including but not limited to promoters, enhancers, termination signals. Without being bound by theory, a cytomegalovirus (CMV) immediate early promoter may provide high and sustained expression levels of an operatively linked nucleic acid sequence in a cell. In some embodiments, the recombinant AAV vector of the disclosure comprises a cytomegalovirus (CMV) immediate early promoter. Without being bound by theory, intronic sequences incorporated into recombinant nucleic acid sequences or transgenes may stabilize mRNA levels and increase expression of an operatively linked nucleic acid sequence. In some embodiments, the recombinant AAV2 vector of the disclosure comprises a beta-globin (HBB2) derived intronic sequence.

In some embodiments, a recombinant AAV2 vector of the disclosure is a recombinant adeno-associated virus (AAV), serotype 2, (rAAV2/2) encoding the human NADH dehydrogenase 4 (ND4) under the control of the cytomegalovirus immediate early promoter (CMV) in an intron-containing expression cassette (beta globin intron, HBB2), further comprising viral inverted terminal repeats (ITRs) from AAV2/2 (FIG. 1). In some embodiments, a CMV promoter comprises SEQ ID NO: 5 or SEQ ID NO: 25. In some embodiments, a HBB2 intron comprises SEQ ID NO: 4 or SEQ ID NO: 24. In some embodiments, an ITR sequence comprises SEQ ID NO: 6, 7, 26 or 27.

TABLE 2

| Sequences of various embodiments of the disclosure | | | |
|---|---|---|---|
| SEQ ID NO: 1 | 3'UTR Cox10 (3' to 5') | 595 nt | aacatgtggaatccccagtcccagtgcacagcagccgggtcctagctattggtattgt<br>tagaaggactatggttgagaatgtgtggggtggggaaaaccaaaaatgcaggccctgg<br>ctcagtcaccaggaaggggggtgctccgaggcctttgagggacctgagctcacagaact<br>acagacagcagatcatgaggctcacactttctggccaccaagtgccactctgctgggc<br>atgtggagtgtgcgtgtggtgtggtggtaaggatggaaccaaaagaggaagctgtgta<br>tgtgtacccccatgtgaggaggaagaaacagaatagagggtggggttggaggagagat<br>gtataaagaccctcaaagggaaaaataattcctttttttgtattcactgactgagctga<br>tgcatttcttatttggggagcattttgggtaatatttaaaaaaaaaaaaaactgtcaa<br>gtgatcactgggcaccgaattcgtttataatcttgttctaaacccagcaatttctctt<br>cttgtgttccagaattaccacaacatgctcgcctggcagcggagggaaaggggcggtg<br>ggcgtcccagtgctc |

TABLE 2-continued

| Sequences of various embodiments of the disclosure | | | |
|---|---|---|---|
| SEQ ID NO: 14 | 3'UTR Cox10 (5' to 3') | 595 nt | gagcactgggacgcccaccgcccctttccctccgctgccaggcgagcatgttgtggta<br>attctggaacacaagaagagaaattgctgggtttagaacaagattataaacgaattcg<br>gtgcccagtgatcacttgacagttttttttttttttaaatattacccaaaatgctccc<br>caaataagaaatgcatcagctcagtcagtgaatacaaaaaaggaattatttttccctt<br>tgagggtctttatacatctctcctccaaccccaccctctattctgtttcttcctcctc<br>acatgggggtacacatacacagcttcctcttttggttccatccttaccaccacaccac<br>acgcacactccacatgcccagcagagtggcacttggtggccagaaagtgtgagcctca<br>tgatctgctgtctgtagttctgtgagctcaggtccctcaaaggcctcggagcaccccc<br>ttcctggtgactgagccagggcctgcattttttggttttccccaccccacacattctca<br>accatagtccttctaacaataccaatagctaggacccggctgctgtgcactgggactg<br>gggattccacatgtt |
| SEQ ID NO: 3 | MTS Cox10 (3' to 5') | 84 nt | agtcctcctttccaggtaccacacactccccccacacagccagtcaggagcctggat<br>gacagtgtatgggggctggcagccat |
| SEQ ID NO: 16 | MTS Cox10 (5' to 3') | 84 nt | atggctgccagcccccatacactgtcatccaggctcctgactggctgtgtggggggga<br>gtgtgtggtacctggaaaggaggact |
| SEQ ID NO: 4 | HBB2 intron (3' to 5') | 398 nt | aattctttgccaaagtgatgggccagcacacagaccagcacgttgcccaggagctgtg<br>ggaggaagataagaggtatgaacatgattagcaaaagggcctagcttggactcagaat<br>aatccagccttatcccaaccataaaataaaagcagaatggtagctggattgtagctgc<br>tattagcaatatgaaacctcttacatcagttacaatttatatgcagaaatatttatat<br>gcagaaatattgctattgccttaacccagaaattatcactgttattctttagaatggt<br>gcaaagaggcatgatacattgtatcattattgccctgaaagaaagagattagggaaag<br>tattagaaataagataaacaaaaaagtatattaaaagaagaaagcatttt |
| SEQ ID NO: 24 | HBB2 intron (5' to 3') | 398 nt | aaaatgctttcttcttttaatatactttttttgtttatcttatttctaatactttccct<br>aatctctttctttcagggcaataatgatacaatgtatcatgcctctttgcaccattct<br>aaagaataacagtgataatttctgggttaaggcaatagcaatatttctgcatataaat<br>atttctgcatataaattgtaactgatgtaagaggtttcatattgctaatagcagctac<br>aatccagctaccattctgcttttattttatggttgggataaggctggattattctgag<br>tccaagctaggcccttttgctaatcatgttcatacctcttatcttcctcccacagctc<br>ctgggcaacgtgctggtctgtgtgctggcccatcactttggcaaagaatt |
| SEQ ID NO: 5 | CMV promoter (3' to 5') | 654 nt | ggaggctggatcggtcccggtgtcttctatggaggtcaaaacagcgtggatggcgtct<br>ccaggcgatctgacggttcactaaacgagctctgcttatatagacctcccaccgtaca<br>cgcctaccgcccatttgcgtcaatggggcggagttgttacgacattttggaaagtccc<br>gttgattttggtgccaaaacaaactcccattgacgtcaatggggtggagacttggaaa<br>tccccgtgagtcaaaccgctatccacgcccattgatgtactgccaaaaccgcatcacc<br>atggtaatagcgatgactaatacgtagatgtactgccaagtaggaaagtcccataagg<br>tcatgtactgggcataatgccaggcgggccatttaccgtcattgacgtcaataggggg<br>cgtacttggcatatgatacacttgatgtactgccaagtgggcagtttaccgtaaatac<br>tccacccattgacgtcaatggaaagtccctattggcgttactatgggaacatacgtca<br>ttattgacgtcaatgggcgggggtcgttgggcggtcagccaggcgggccatttaccgt<br>aagttatgtaacgcggaactccatatatgggctatgaactaatgaccccgtaattgat<br>tactattaataactag |
| SEQ ID NO: 25 | CMV promoter (5' to 3') | 654 nt | ctagttattaatagtaatcaattacggggtcattagttcatagcccatatatggagtt<br>ccgcgttacataacttacggtaaatggcccgcctggctgaccgcccaacgacccccgc<br>ccattgacgtcaataatgacgtatgttcccatagtaacgccaatagggactttccatt<br>gacgtcaatgggtggagtatttacggtaaactgcccacttggcagtacatcaagtgta<br>tcatatgccaagtacgccccctattgacgtcaatgacggtaaatggcccgcctggcat<br>tatgcccagtacatgaccttatgggactttcctacttggcagtacatctacgtattag<br>tcatcgctattaccatggtgatgcggttttggcagtacatcaatgggcgtggatagcg<br>gtttgactcacggggatttccaagtctccaccccattgacgtcaatgggagtttgttt<br>tggcaccaaaatcaacgggactttccaaaatgtcgtaacaactccgccccattgacgc<br>aaatgggcggtaggcgtgtacggtgggaggtctatataagcagagctcgtttagtgaa<br>ccgtcagatcgcctggagacgccatccacgctgttttgacctccatagaagacaccgg<br>gaccgatccagcctcc |
| SEQ ID NO: 6 | ITR (3' to 5') | 128 nt | aggaacccctagtgatggagttggccactccctctctgcgcgctcgctcgctcactga<br>ggccgggcgaccaaaggtcgcccgacgcccgggctttgcccgggcggcctcagtgagc<br>gagcgagcgcgc |
| SEQ ID NO: 26 | ITR (5' to 3') | 128 nt | gcgcgctcgctcgctcactgaggccgcccgggcaaagcccgggcgtcgggcgaccttt<br>ggtcgcccggcctcagtgagcgagcgagcgcgcagagagggagtggccaactccatca<br>ctaggggttcct |

TABLE 2-continued

| Sequences of various embodiments of the disclosure | | | |
|---|---|---|---|
| SEQ ID NO: 7 | ITR (3' to 5') | 130 nt | ctgcgcgctcgctcgctcactgaggccgcccgggcaaagcccgggcgtcgggcgacct ttggtcgcccggcctcagtgagcgagcgagcgcgcagagagggagtggccaactccat cactaggggttcct |
| SEQ ID NO: 27 | ITR (5' to 3') | 130 nt | aggaacccctagtgatggagttggccactccctctctgcgcgctcgctcgctcactga ggccgggcgaccaaaggtcgcccgacgcccgggctttgcccgggcggcctcagtgagc gagcgagcgcgcag |

In some embodiments, the recombinant AAV2 vector of the disclosure comprises a coding sequence of human ND4 that is codon-optimized for improved expression in human cells.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence comprising SEQ ID NO: 1;

(ii) a coding sequence ND4 comprising SEQ ID NO: 2; and (iii) an MTS Cox10 sequence comprising SEQ ID NO: 3.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence consisting of SEQ ID NO: 1;

(ii) a coding sequence ND4 consisting of SEQ ID NO: 2; and (iii) an MTS Cox10 sequence consisting of SEQ ID NO: 3.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence comprising SEQ ID NO: 1;

(ii) a coding sequence ND4 comprising SEQ ID NO: 17; and (iii) an MTS Cox10 sequence comprising SEQ ID NO: 3.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence consisting of SEQ ID NO: 1;

(ii) a coding sequence ND4 consisting of SEQ ID NO: 17; and, (iii) an MTS Cox10 sequence consisting of SEQ ID NO: 3.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence comprising SEQ ID NO: 14;

(ii) a coding sequence ND4 comprising SEQ ID NO: 15; and (iii) an MTS Cox10 sequence comprising SEQ ID NO: 16

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence consisting of SEQ ID NO: 14;

(ii) a coding sequence ND4 consisting of SEQ ID NO: 15; and (iii an MTS Cox10 sequence consisting of SEQ ID NO: 16.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence comprising SEQ ID NO: 14;

(ii) a coding sequence ND4 comprising SEQ ID NO: 18; and (iii) an MTS Cox10 sequence comprising SEQ ID NO: 16.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence consisting of SEQ ID NO: 14;

(ii) a coding sequence ND4 consisting of SEQ ID NO: 18; and (iii) an MTS Cox10 sequence consisting of SEQ ID NO: 16.

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(SEQ ID NO: 1)
aacatgtggaatccccagtcccagtgcacagcagccgggtcctagctatt
ggtattgttagaaggactatggttgagaatgtgtggggtggggaaaacca
aaaatgcaggccctggctcagtcaccaggaagggggtgctccgaggcctt
tgagggacctgagctcacagaactacagacagcagatcatgaggctcaca
ctttctggccaccaagtgccactctgctgggcatgtggagtgtgcgtgtg
gtgtggtggtaaggatggaaccaaaagaggaagctgtgtatgtgtacccc
catgtgaggaggaagaaacagaatagagggtggggttggaggagagatgt
ataaagaccctcaaagggaaaaataattcctttttttgtattcactgactg
agctgatgcatttcttatttggggagcattttgggtaatatttaaaaaaa
aaaaaaactgtcaagtgatcactgggcaccgaattcgtttataatcttgt
tctaaacccagcaatttctcttcttgtgttccagaattaccacaacatgc
tcgcctggcagcggagggaaaggggcggtgggcgtcccagtgctc (ii) a coding sequence ND4 of:

(SEQ ID NO: 2)
atgagaaaccagtgataatgtctgggttcagggacagcagcaggatggga
gacagatgcataaacatcagggtgttctctctggtgaatgagggcttcat -continued

```
gttattaatgtggtgagtcagtgagccccactgggtagtggtaaacatgt
acaggctgtagagggctgtgaccagcatgttcagtcctgtcaggagcagg
gtgatgttgctccaggagaatgttgtcaccagcactgacagctctcccag
caggttaattgtagggggcagagccaggttggccagactagccaggagcc
accagaaagccatcagtgggagcagggtctggagcccctgactcaggatc
ataattcttgagtgagttctttcatagttgctatttgccaggcagaacag
gaggctgctggtcagcccatgagcaatcatgaggatcactgccccagtaa
aggaccagggtgtctgaatcagaatggcagtcaccaccagtgccatgtgg
ctgatggagctgtaagcaatcaggctcttgaggtcagtctgcctgagaca
gatggagctggtcatgatcataccccagaggctcagaaccaggaaagggt
aagccatgtgctttgtcagagggttcaggatcagggtgagcctcatcata
ccataaccacccagcttcaggaggacagcagccaggaccatggagccagc
tattggagcttccacatgagccttggggagccagaggtgcaggccataga
ggggcatcttcaccataaaggccattgtataagccagccacatcaggttg
tttgcccaggagttactcagctcctgggcagtcagagtcagcaggaggat
gttcaggctacccagtgtgttgtgggtatagatcagtgcaatcagcaggg
gcagtgagcccaccagtgtataaaagagaaagtaggtgcctgcattcagc
ctctcaggctgatttccccacctagtgatgatggccagggttgggatgag
agtggtctcaaagaagatatagaacatgatcagctcagtggctgtgaagg
tcataatcaggctgatttgcaggctaatgagcatggacaggtacagcttt
ttccttgacagaggctctgagctgaggtgcctctgactggccatgatagt
cagaggcagcagccatgtggtcagcatgagcagggggggttgtcaggggat
cagaggaaaaggtaggggagcatgaaaagaggttattattaatctggttg
aaaaacagcagtgggatgatgctgataatcaggctgtgggttgtggtgtt
aatccaaatcatgtgcttttttgctcagccatgtgagaggcagcagcatga
tggttggcacaatcagcttcagca
```

(iii) an MTS Cox10 sequence of:

```
                                      (SEQ ID NO: 3)
agtcctcctttccaggtaccacacactcccccccacacagccagtcagga
gcctggatgacagtgtatgggggctggcagccat
```

(iv) an HBB2 intron sequence of:

```
                                      (SEQ ID NO: 4)
aattctttgccaaagtgatgggccagcacacagaccagcacgttgcccag
gagctgtgggaggaagataagaggtatgaacatgattagcaaaagggcct
agcttggactcagaataatccagccttatcccaaccataaaataaaagca
gaatggtagctggattgtagctgctattagcaatatgaaacctcttacat
cagttacaatttatatgcagaaatatttatatgcagaaatattgctattg
ccttaacccagaaattatcactgttattctttagaatggtgcaaagaggc
atgatacattgtatcattattgccctgaaagaaagagattagggaaagta
ttagaaataagataaacaaaaaagtatattaaaagaagaaagcatttt
```

(v) a CMV promoter sequence of:

```
                                      (SEQ ID NO: 5)
ggaggctggatcggtcccggtgtcttctatggaggtcaaaacagcgtgga
tggcgtctccaggcgatctgacggttcactaaacgagctctgcttatata
gacctcccaccgtacacgcctaccgcccatttgcgtcaatggggcggagt
tgttacgacattttggaaagtcccgttgattttggtgccaaaacaaactc
ccattgacgtcaatggggtggagacttggaaatccccgtgagtcaaaccg
ctatccacgcccattgatgtactgccaaaaccgcatcaccatggtaatag
cgatgactaatacgtagatgtactgccaagtaggaaagtcccataaggtc
atgtactgggcataatgccaggcgggccatttaccgtcattgacgtcaat
agggggcgtacttggcatatgatacacttgatgtactgccaagtgggcag
tttaccgtaaatactccacccattgacgtcaatggaaagtccctattggc
gttactatgggaacatacgtcattattgacgtcaatgggcgggggtcgtt
gggcggtcagccaggcgggccatttaccgtaagttatgtaacgcggaact
ccatatatgggctatgaactaatgaccccgtaattgattactattaataa
ctag
```

(vi) an ITR sequence of:

```
                                      (SEQ ID NO: 6)
aggaacccctagtgatggagttggccactccctctctgcgcgctcgctcg
ctcactgaggccgggcgaccaaaggtcgcccgacgcccgggctttgcccg
ggcggcctcagtgagcgagcgagcgcgc,
```

and (vii) an ITR sequence of:

```
                                      (SEQ ID NO: 7)
ctgcgcgctcgctcgctcactgaggccgcccgggcaaagcccgggcgtcg
ggcgacctttggtcgcccggcctcagtgagcgagcgagcgcgcagagagg
gagtggccaactccatcactaggggttcct.
```

In some embodiments, a recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence comprising SEQ ID NO: 1,
(ii) a coding sequence ND4 comprising SEQ ID NO: 17,
(iii) an MTS Cox10 sequence comprising SEQ ID NO: 3,
(iv) an HBB2 intron sequence comprising SEQ ID NO: 4,
(v) a CMV promoter sequence comprising SEQ ID NO: 5,
(vi) an ITR sequence comprising SEQ ID NO: 6, and
(vii) an ITR sequence comprising SEQ ID NO: 7.

In some embodiments, the recombinant AAV vector of the disclosure is a recombinant adeno-associated virus (AAV), serotype 2, (rAAV2/2) encoding the gene of the human NADH dehydrogenase 4 (ND4), and comprises:

(i) a 3'UTR Cox10 sequence comprising SEQ ID NO: 14,
(ii) a coding sequence ND4 comprising SEQ ID NO: 15,
(iii) an MTS Cox10 sequence comprising SEQ ID NO: 16,
(iv) an HBB2 intron sequence comprising SEQ ID NO: 24, (v) a CMV promoter sequence comprising SEQ ID NO: 25,
(vi) an ITR sequence comprising SEQ ID NO: 26, and
(vii) an ITR sequence comprising SEQ ID NO: 27.

In some embodiments, the recombinant AAV vector of the disclosure is a recombinant adeno-associated virus (AAV), serotype 2, (rAAV2/2) encoding the gene of the human NADH dehydrogenase 4 (ND4), and comprises:
(i) a 3'UTR Cox10 sequence comprising SEQ ID NO: 14,
(ii) a coding sequence ND4 comprising SEQ ID NO: 18,
(iii) an MTS Cox10 sequence comprising SEQ ID NO: 16,
(iv) an HBB2 intron sequence comprising SEQ ID NO: 24,
(v) a CMV promoter sequence comprising SEQ ID NO: 25,
(vi) an ITR sequence comprising SEQ ID NO: 26, and
(vii) an ITR sequence comprising SEQ ID NO: 27.

In some embodiment, the recombinant vector of the disclosure further comprises:
(i) an HBB2 intron sequence comprising SEQ ID NO: 4,
(ii) a CMV promoter sequence comprising SEQ ID NO: 5,
(iii) an ITR sequence comprising SEQ ID NO: 6, and
(iv) an ITR sequence comprising SEQ ID No: 7.

In some embodiment, the recombinant vector of the disclosure further comprises:
(i) an HBB2 intron sequence consisting of SEQ ID NO: 4,
(ii) a CMV promoter sequence consisting of SEQ ID NO: 5,
(iii) an ITR sequence consisting of SEQ ID NO: 6, and
(iv) an ITR sequence consisting of SEQ ID No: 7.

In some embodiment, the recombinant vector of the disclosure further comprises:
(i) an HBB2 intron sequence comprising SEQ ID NO: 24,
(ii) a CMV promoter sequence comprising SEQ ID NO: 25,
(iii) an ITR sequence comprising SEQ ID NO: 26, and
(iv) an ITR sequence comprising SEQ ID No: 27.

In some embodiment, the recombinant vector of the disclosure further comprises:
(i) an HBB2 intron sequence consisting of SEQ ID NO: 24,
(ii) a CMV promoter sequence consisting of SEQ ID NO: 25,
(iii) an ITR sequence consisting of SEQ ID NO: 26, and
(iv) an ITR sequence consisting of SEQ ID No: 27.

In some embodiments, a recombinant vector of the disclosure is a recombinant adeno-associated virus (AAV), serotype 2, (rAAV2/2) encoding a ND4 protein, and comprises:
a 3'UTR Cox10 sequence comprising SEQ ID NO: 14,
a nucleic acid sequence encoding an ND4 polypeptide comprising SEQ ID NO: 13, and
a nucleic acid sequence encoding an MTS Cox10 polypeptide sequence comprising SEQ ID NO: 11.

In some embodiments, a recombinant vector of the disclosure is a recombinant adeno-associated virus (AAV), serotype 2, (rAAV2/2) encoding a ND4 protein, and comprises:
a 3'UTR Cox10 sequence comprising SEQ ID NO: 14,
a nucleic acid sequence encoding an ND4 polypeptide SEQ ID NO: 13, and
a nucleic acid sequence encoding MTS Cox10 polypeptide sequence comprising SEQ ID NO: 12.

In some embodiments, a recombinant vector of the disclosure is a recombinant adeno-associated virus (AAV), serotype 2, (rAAV2/2) encoding a ND4 protein, and comprises:
a 3'UTR Cox10 sequence comprising SEQ ID NO: 1,
a nucleic acid sequence encoding an ND4 polypeptide comprising SEQ ID NO: 13, and
a nucleic acid sequence encoding an MTS Cox10 polypeptide sequence comprising SEQ ID NO: 11.

In some embodiments, a recombinant vector of the disclosure is a recombinant adeno-associated virus (AAV), serotype 2, (rAAV2/2) encoding a ND4 protein, and comprises:
a 3'UTR Cox10 sequence comprising SEQ ID NO: 1,
a nucleic acid sequence encoding an ND4 polypeptide SEQ ID NO: 13, and
a nucleic acid sequence encoding MTS Cox10 polypeptide sequence comprising SEQ ID NO: 12.

TABLE 3

Sequences of various embodiments of the disclosure

| | | | |
|---|---|---|---|
| SEQ ID NO: 11 | Cox10 MTS (cleaved) | 20 AA | MAASPHTLSSRLLTGCVGGS |
| SEQ ID NO: 12 | Cox10 MTS (uncleaved) | 28 AA | MAASPHTLSSRLLTGCVGGSVWYLERRT |

Sequences such as promoters, introns or ITR are well known to person of ordinary skill in the art who can easily interchange each of them with other elements known in the art.

Recombinant vectors of the disclosure are useful in treating Leber Hereditary Optic Neuroretinopathy (LHON), including ND4-related LHON.

In some embodiments, a recombinant vector of the disclosure is administered to a patient in need thereof via intravitreal injection.

In some embodiments, a recombinant vector of the disclosure is administered to a patient in need thereof via a single intravitreal injection.

In some embodiments, a recombinant viral vector of the disclosure is administered to patients in need thereof in one or more doses of about $10^9$ to $10^{11}$ vg (viral genomes) per eye. In some embodiments, a recombinant AAV2 vector of the disclosure is administered to patients in need thereof in one or more doses of about $10^{10}$ vg per eye, for example $9\times10^{10}$ vg per eye.

One aspect of the disclosure pertains to a pAAV-ND4 transfer plasmid that, in some embodiments, may be used in the preparation of a recombinant AAV2 vector of the disclosure.

In some embodiments, a pAAV-ND4 transfer plasmid of the disclosure comprises the following functional elements and sequences:
3'UTR Cox10: nt 11-605=595 bp
Coding sequence ND4: nt 618-1997=1380 bp
MTS Cox10: nt 1998-2081=84 bp
HBB2 intron: nt 2124-2616=493 bp
CMV promoter: nt 2624-3283=660 bp
ITR: nt 3327-3454=128 bp
F1 origin: nt 3872-4327=456 bp
Kana R gene: nt 4482-5273=792 bp
COLE1 origin: nt 5488-6102=615 bp
ITR: nt 6324-6453=130 bp.

TABLE 4

Annotated regions within one embodiment of the pAAV-ND4 plasmid

| Name | Start | Stop | Sequence |
|---|---|---|---|
| 3'UTR COX10 (polyA sequence underlined) | 11 | 605 | aacatgtggaatccccagtcccagtgcacagcagccgggtcctagctattggtattgttagaa<br>ggactatggttgagaatgtgtggggtggggaaaaccaaaaatgcaggccctggctcagtca<br>ccaggaaggggggtgctccgaggcctttgagggacctgagctcacagaactacagacagca<br>gatcatgaggctcacactttctggccaccaagtgccactctgctgggcatgtggagtgtgcgtg<br>tggtgtggtggtaaggatggaaccaaaagaggaagctgtgtatgtgtaccccatgtgagga<br>ggaagaaacagaatagagggtggggttggaggagagatgtataaagaccctcaaaggga<br>aaaataattcctttttttgtattcactgactgagctgatgcatttcttatttggggagcattttgggtaat<br>atttaaaaaaaaaaaaaactgtcaagtgatcactgggcaccgaattcgtttataatcttgttcta<br>aacccagcaatttctcttcttgtgttccagaattaccacaacatgctcgcctggcagcggaggg<br>aaaggggcggtgggcgtcccagtgctc |
| ND4 | 618 | 1997 | tcaggatgagaaaccagtgataatgtctgggttcagggacagcagcaggatgggagacag<br>atgcataaacatcagggtgttctctctggtgaatgagggcttcatgttattaatgtggtgagtcagt<br>gagccccactgggtagtggtaaacatgtacaggctgtagagggctgtgaccagcatgttcag<br>tcctgtcaggagcagggtgatgttgctccaggagaatgttgtcaccagcactgacagctctcc<br>cagcaggttaattgtaggggggcagagccaggttggccagactagccaggagccaccagaa<br>agccatcagtgggagcagggtctggagcccctgactcaggatcataattcttgagtgagttcttt<br>catagttgctatttgccaggcagaacaggaggctgctggtcagcccatgagcaatcatgagg<br>atcactgccccagtaaaggaccagggtgtctgaatcagaatggcagtcaccaccagtgcca<br>tgtggctgatggagctgtaagcaatcaggctcttgaggtcagtctgcctgagacagatggagc<br>tggtcatgatcataccccagaggctcagaaccaggaaagggtaagccatgtgctttgtcaga<br>gggttcaggatcagggtgagcctcatcataccataaccacccagcttcaggaggacagcag<br>ccaggaccatggagccagctattggagcttccacatgagccttggggagccagaggtgcag<br>gccatagaggggcatcttcaccataaaggccattgtataagccagccacatcaggttgtttgc<br>ccaggagttactcagctcctgggcagtcagagtcagcaggaggatgttcaggctacccagtg<br>tgttgtgggtatagatcagtgcaatcagcaggggcagtgagcccaccagtgtataaaagaga<br>aagtaggtgcctgcattcagcctctcaggctgatttccccacctagtgatgatggccagggttg<br>ggatgagagtggtctcaaagaagatatagaacatgatcagctcagtggctgtgaaggtcata<br>atcaggctgatttgcaggctaatgagcatggacaggtacagctttttccttgacagaggctctg<br>agctgaggtgcctctgactggccatgatagtcagaggcagcagccatgtggtcagcatgagc<br>aggggggttgtcaggggatcagaggaaaaggtaggggagcatgaaaagaggttattatta<br>atctggttgaaaaacagcagtgggatgatgctgataatcaggctgtgggttgtggtgttaatcc<br>aaatcatgtgctttttgctcagccatgtgagaggcagcagcatgatggttggcacaatcagcttc<br>agcat |
| MTS Cox10 | 1998 | 2081 | agtcctcctttccaggtaccacacactcccccccacacagccagtcaggagcctggatgaca<br>gtgtatgggggctggcagccat |
| betaglobin intron | 2124 | 2616 | atcccaattctttgccaaagtgatgggccagcacacagaccagcacgttgcccaggagctgt<br>gggaggaagataagaggtatgaacatgattagcaaaagggcctagcttggactcagaata<br>atccagccttatcccaaccataaaataaaagcagaatggtagctggattgtagctgctattagc<br>aatatgaaacctcttacatcagttacaatttatatgcagaaatatttatatgcagaaatattgctatt<br>gccttaacccagaaattatcactgttattctttagaatggtgcaaagaggcatgatacattgtatc<br>attattgccctgaaagaaagagattagggaaagtattagaaataagataaacaaaaaagtat<br>attaaaagaagaaagcatttttttgtgggcctatagactctataggcggtacttacgtcactcttgg<br>cacggggaatccgcgttccaatgcaccgttcccggccgggattcg |
| CMV promoter | 2624 | 3283 | ggaggctggatcggtcccggtgtcttctatggaggtcaaaacagcgtggatggcgtctccagg<br>cgatctgacggttcactaaacgagctctgcttatatagacctcccaccgtacacgcctaccgcc<br>catttgcgtcaatggggcggagttgttacgacattttggaaagtcccgttgattttggtgccaaaa<br>caaactcccattgacgtcaatggggtggagacttggaaatccccgtgagtcaaaccgctatc<br>cacgcccattgatgtactgccaaaaccgcatcaccatggtaatagcgatgactaatacgtag<br>atgtactgccaagtaggaaagtcccataaggtcatgtactgggcataatgccaggcgggcca<br>tttaccgtcattgacgtcaatagggggcgtacttggcatatgatacacttgatgtactgccaagt<br>gggcagtttaccgtaaatactccacccattgacgtcaatggaaagtccctattggcgttactatg<br>ggaacatacgtcattattgacgtcaatgggcgggggtcgttgggcggtcagccaggcgggcc<br>atttaccgtaagttatgtaacgcggaactccatatatgggctatgaactaatgaccccgtaattg<br>attactattaataactagacgcgt |
| 5' ITR | 3327 | 3454 | aggaacccctagtgatggagttggccactccctctctgcgcgctcgctcgctcactgaggccg<br>ggcgaccaaaggtcgcccgacgcccgggctttgcccgggcggcctcagtgagcgagcga<br>gcgcgc |
| F1 origin | 3872 | 4327 | acgcgccctgtagcggcgcattaagcgcggcgggtgtggtggttacgcgcagcgtgaccgc<br>tacacttgccagcgccctagcgcccgctcctttcgctttcttcccttcctttctcgccacgttcgccg<br>gctttccccgtcaagctctaaatcgggggctccctttagggttccgatttagtgctttacggcacct<br>cgaccccaaaaaacttgattagggtgatggttcacgtagtgggccatcgccctgatagacggt<br>ttttcgccctttgacgttggagtccacgttctttaatagtggactcttgttccaaactggaacaaca<br>ctcaaccctatctcggtctattcttttgatttataagggattttgccgatttcggcctattggttaaaaa<br>atgagctgatttaacaaaaatttaacgcgaattttaacaaaatattaacgcttacaattt |
| Kana R gene | 4482 | 5273 | attgaacaagatggattgcacgcaggttctccggccgcttgggtggagaggctattcggctat<br>gactgggcacaacagacaatcggctgctctgatgccgccgtgttccggctgtcagcgcaggg<br>gcgcccggttctttttgtcaagaccgacctgtccggtgccctgaatgaactgcaagacgaggc<br>agcgcggctatcgtggctggccacgacgggcgttccttgcgcagctgtgctcgacgttgtcact<br>gaagcgggaagggactggctgctattgggcgaagtgccggggcaggatctcctgtcatctca |

TABLE 4-continued

| Annotated regions within one embodiment of the pAAV-ND4 plasmid | | | |
|---|---|---|---|
| Name | Start | Stop | Sequence |
| | | | ccttgctcctgccgagaaagtatccatcatggctgatgcaatgcggcggctgcatacgcttgat<br>ccggctacctgcccattcgaccaccaagcgaaacatcgcatcgagcgagcacgtactcgg<br>atggaagccggtcttgtcgatcaggatgatctggacgaagagcatcaggggctcgcgccag<br>ccgaactgttcgccaggctcaaggcgagcatgcccgacggcgaggatctcgtcgtgaccca<br>tggcgatgcctgcttgccgaatatcatggtggaaaatggccgcttttctggattcatcgactgtgg<br>ccggctgggtgtggcggaccgctatcaggacatagcgttggctacccgtgatattgctgaaga<br>gcttggcggcgaatgggctgaccgcttcctcgtgctttacggtatcgccgctcccgattcgcag<br>cgcatcgccttctatcgccttcttgacgagttcttctga |
| ColE1 origin | 5488 | 6102 | aaaggatcttcttgagatcctttttttctgcgcgtaatctgctgcttgcaaacaaaaaaaccaccg<br>ctaccagcggtggtttgtttgccggatcaagagctaccaactctttttccgaaggtaactggcttc<br>agcagagcgcagataccaaatactgtccttctagtgtagccgtagttaggccaccacttcaag<br>aactctgtagcaccgcctacatacctcgctctgctaatcctgttaccagtggctgctgccagtgg<br>cgataagtcgtgtcttaccgggttggactcaagacgatagttaccggataaggcgcagcggtc<br>gggctgaacggggggttcgtgcacacagcccagcttggagcgaacgacctacaccgaact<br>gagatacctacagcgtgagctatgagaaagcgccacgcttcccgaagggagaaaggcgg<br>acaggtatccggtaagcggcagggtcggaacaggagagcgcacgagggagcttccagg<br>gggaaacgcctggtatctttatagtcctgtcgggtttcgccacctctgacttgagcgtcgatttttgt<br>gatgctcgtcaggggggcggagcctatggaaaaacgccagcaacgcg |
| 3' ITR | 6324 | 6453 | ctgcgcgctcgctcgctcactgaggccgcccgggcaaagcccgggcgtcgggcgacctttg<br>gtcgcccggcctcagtgagcgagcgagcgcgcagagagggagtggccaactccatcacta<br>ggggttcct |

In some embodiments, a pAAV-ND4 transfer plasmid of the disclosure comprises:

(i) a 3'UTR Cox10 sequence of SEQ ID NO: 1,
(ii) a coding sequence ND4 of SEQ ID NO: 2,
(iii) an MTS Cox10 sequence of SEQ ID NO: 3,
(iv) an HBB2 intron sequence of SEQ ID NO: 4,
(v) a CMV promoter sequence of SEQ ID NO: 5,
(vi) an ITR sequence of SEQ ID NO: 6, and
(vii) an ITR sequence of SEQ ID NO: 7.

in some embodiments, a pAAV-ND4 transfer plasmid of the disclosure comprises:

(i) a 3'UTR Cox10 sequence of SEQ ID NO: 1,
(ii) a coding sequence ND4 of SEQ ID NO: 17,
(iii) an MTS Cox10 sequence of SEQ ID NO: 3,
(iv) an HBB2 intron sequence of SEQ ID NO: 4,
(v) a CMV promoter sequence of SEQ ID NO: 5,
(vi) an ITR sequence of SEQ ID NO: 6, and
(vii) an ITR sequence of SEQ ID NO: 7.

In some embodiments, a pAAV-ND4 transfer plasmid of the disclosure comprises:

(i) a 3'UTR Cox10 sequence of SEQ ID NO: 14,
(ii) a coding sequence ND4 of SEQ ID NO: 15,
(iii) an MTS Cox10 sequence of SEQ ID NO: 16,
(iv) an HBB2 intron sequence of SEQ ID NO: 24,
(v) a CMV promoter sequence of SEQ ID NO: 25,
(vi) an ITR sequence of SEQ ID NO: 26, and
(vii) an ITR sequence of SEQ ID NO: 27.

In some embodiments, a pAAV-ND4 transfer plasmid of the disclosure comprises:

(i) a 3'UTR Cox10 sequence of SEQ ID NO: 14,
(ii) a coding sequence ND4 of SEQ ID NO: 18,
(iii) an MTS Cox10 sequence of SEQ ID NO: 16,
(iv) an HBB2 intron sequence of SEQ ID NO: 24,
(v) a CMV promoter sequence of SEQ ID NO: 25,
(vi) an ITR sequence of SEQ ID NO: 26, and
(vii) an ITR sequence of SEQ ID NO: 27.

In some embodiments, a pAAV-ND4 transfer plasmid of the disclosure comprises:

```
                                                          (SEQ ID NO: 22)
gctcggtccgaacatgtggaatccccagtcccagtgcacagcagccgggtcctagctattggtattgttaga

aggactatggttgagaatgtgtggggtggggaaaaccaaaaatgcaggccctggctcagtcaccaggaa

gggggtgctccgaggcctttgagggacctgagctcacagaactacagacagcagatcatgaggctcaca

ctttctggccaccaagtgccactctgctgggcatgtggagtgtgcgtgtggtgtggtggtaaggatggaacca

aaagaggaagctgtgtatgtgtacccccatgtgaggaggaagaaacagaatagagggtggggttggag

gagagatgtataaagaccctcaaagggaaaaataattcctttttttgtattcactgactgagctgatgcatttctt

atttggggagcattttgggtaatatttaaaaaaaaaaaaaaactgtcaagtgatcactgggcaccgaattcgttt

ataatcttgttctaaacccagcaatttctcttcttgtgttccagaattaccacaacatgctcgcctggcagcgga

gggaaaggggcggtgggcgtcccagtgctcagatctctcgagtcaggatgagaaaccagtgataatgtct

gggttcagggacagcagcaggatgggagacagatgcataaacatcagggtgttctctctggtgaatgagg

gcttcatgttattaatgtggtgagtcagtgagccccactgggtagtggtaaacatgtacaggctgtagagggc

tgtgaccagcatgttcagtcctgtcaggagcagggtgatgttgctccaggagaatgttgtcaccagcactga
```

-continued cagctctcccagcaggttaattgtagggggcagagccaggttggccagactagccaggagccaccagaa agccatcagtgggagcagggtctggagcccctgactcaggatcataattcttgagtgagttctttcatagttgc tatttgccaggcagaacaggaggctgctggtcagcccatgagcaatcatgaggatcactgccccagtaaa ggaccagggtgtctgaatcagaatggcagtcaccaccagtgccatgtggctgatggagctgtaagcaatc aggctcttgaggtcagtctgcctgagacagatggagctggtcatgatcataccccagaggctcagaaccag gaaagggtaagccatgtgctttgtcagagggttcaggatcagggtgagcctcatcataccataaccaccca gcttcaggaggacagcagccaggaccatggagccagctattggagcttccacatgagccttggggagcc agaggtgcaggccatagaggggcatcttcaccataaaggccattgtataagccagccacatcaggttgttt gcccaggagttactcagctcctgggcagtcagagtcagcaggaggatgttcaggctacccagtgtgttgtg ggtatagatcagtgcaatcagcaggggcagtgagcccaccagtgtataaaagagaaagtaggtgcctgc attcagcctctcaggctgatttccccacctagtgatgatggccagggttgggatgagagtggtctcaaagaa gatatagaacatgatcagctcagtggctgtgaaggtcataatcaggctgatttgcaggctaatgagcatgga caggtacagcttttttccttgacagaggctctgagctgaggtgcctctgactggccatgatagtcagaggcagc agccatgtggtcagcatgagcaggggggttgtcaggggatcagaggaaaaggtaggggagcatgaaaa gaggttattattaatctggttgaaaaacagcagtgggatgatgctgataatcaggctgtgggttgtggtgttaat ccaaatcatgtgctttttgctcagccatgtgagaggcagcagcatgatggttggcacaatcagcttcagcata gtcctcctttccaggtaccacacactcccccccacacagccagtcaggagcctggatgacagtgtatgggg gctggcagccatgtcgactctagaggatccccggggaattcaatcgatgttcgaatcccaattctttgccaaa gtgatgggccagcacacagaccagcacgttgcccaggagctgtgggaggaagataagaggtatgaaca tgattagcaaaagggcctagcttggactcagaataatccagccttatcccaaccataaaataaaagcaga atggtagctggattgtagctgctattagcaatatgaaacctcttacatcagttacaatttatatgcagaaatattt atatgcagaaatattgctattgccttaacccagaaattatcactgttattctttagaatggtgcaaagaggcatg atacattgtatcattattgccctgaaagaaagagattagggaaagtattagaaataagataaacaaaaaag tatattaaaagaagaaagcatttttttgtgggcctatagactctataggcggtacttacgtcactcttggcacggg gaatccgcgttccaatgcaccgttcccggccgggattcgaatccgcggaggctggatcggtcccggtgtctt ctatggaggtcaaaacagcgtggatggcgtctccaggcgatctgacggttcactaaacgagctctgcttata tagacctcccaccgtacacgcctaccgcccatttgcgtcaatggggcggagttgttacgacattttggaaagt cccgttgattttggtgccaaaacaaactcccattgacgtcaatggggtggagacttggaaatccccgtgagtc aaaccgctatccacgcccattgatgtactgccaaaaccgcatcaccatggtaatagcgatgactaatacgt agatgtactgccaagtaggaaagtcccataaggtcatgtactgggcataatgccaggcgggccatttaccg tcattgacgtcaatagggggcgtacttggcatatgatacacttgatgtactgccaagtgggcagtttaccgtaa atactccacccattgacgtcaatggaaagtccctattggcgttactatgggaacatacgtcattattgacgtca atgggcgggggtcgttgggcggtcagccaggcgggccatttaccgtaagttatgtaacgcggaactccata tatgggctatgaactaatgaccccgtaattgattactattaataactagacgcgtgcggccgtagataagtag catggcgggttaatcattaactacaaggaacccctagtgatggagttggccactccctctctgcgcgctcgct cgctcactgaggccgggcgaccaaaggtcgcccgacgcccgggctttgcccgggcggcctcagtgagc gagcgagcgcgccagctggcgtaatagcgaagaggcccgcaccgatcgcccttcccaacagttgcgca gcctgaatggcgaatggattccagacgattgagcgtcaaaatgtaggtatttccatgagcgtttttccgttgca -continued atggctggcggtaatattgttctggatattaccagcaaggccgatagtttgagttcttctactcaggcaagtgat gttattactaatcaaagaagtattgcgacaacggttaatttgcgtgatggacagactcttttactcggtggcctc actgattataaaaacacttctcaggattctggcgtaccgttcctgtctaaaatccctttaatcggcctcctgtttag ctcccgctctgattctaacgaggaaagcacgttatacgtgctcgtcaaagcaaccatagtacgcgccctgta gcggcgcattaagcgcggcgggtgtggtggttacgcgcagcgtgaccgctacacttgccagcgccctagc gcccgctcctttcgctttcttcccttcctttctcgccacgttcgccggctttccccgtcaagctctaaatcgggggc tccctttagggttccgatttagtgctttacggcacctcgaccccaaaaaacttgattagggtgatggttcacgta gtgggccatcgccctgatagacggtttttcgccctttgacgttggagtccacgttctttaatagtggactcttgttc caaactggaacaacactcaaccctatctcggtctattcttttgatttataagggattttgccgatttcggcctattg gttaaaaaatgagctgatttaacaaaaatttaacgcgaattttaacaaaatattaacgcttacaatttaggtgg cacttttcggggaaatgtgcgcggaacccctatttgtttatttttctaaatacattcaaatatgtatccgctcatga gacaataaccctgataaatgcttcaataatagcacctagatcaagagacaggatgaggatcgtttcgcatg attgaacaagatggattgcacgcaggttctccggccgcttgggtggagaggctattcggctatgactgggca caacagacaatcggctgctctgatgccgccgtgttccggctgtcagcgcaggggcgcccggttctttttgtca agaccgacctgtccggtgccctgaatgaactgcaagacgaggcagcgcggctatcgtggctggccacga cgggcgttccttgcgcagctgtgctcgacgttgtcactgaagcgggaagggactggctgctattgggcgaa gtgccggggcaggatctcctgtcatctcaccttgctcctgccgagaaagtatccatcatggctgatgcaatgc ggcggctgcatacgcttgatccggctacctgcccattcgaccaccaagcgaaacatcgcatcgagcgagc acgtactcggatggaagccggtcttgtcgatcaggatgatctggacgaagagcatcaggggctcgcgcca gccgaactgttcgccaggctcaaggcgagcatgcccgacggcgaggatctcgtcgtgacccatggcgat gcctgcttgccgaatatcatggtggaaaatggccgcttttctggattcatcgactgtggccggctgggtgtggc ggaccgctatcaggacatagcgttggctacccgtgatattgctgaagagcttggcggcgaatgggctgacc gcttcctcgtgctttacggtatcgccgctcccgattcgcagcgcatcgccttctatcgccttcttgacgagttcttct gaattattaacgcttacaatttcctgatgcggtattttctccttacgcatctgtgcggtatttcacaccgcatcaggt ggcacttttcggggaaatgtgcgcggaacccctatttgtttatttttctaaatacattcaaatatgtatccgctcat gaccaaaatcccttaacgtgagttttcgttccactgagcgtcagaccccgtagaaaagatcaaaggatcttct tgagatcctttttttctgcgcgtaatctgctgcttgcaaacaaaaaaaccaccgctaccagcggtggtttgtttgc cggatcaagagctaccaactctttttccgaaggtaactggcttcagcagagcgcagataccaaatactgtcc ttctagtgtagccgtagttaggccaccacttcaagaactctgtagcaccgcctacatacctcgctctgctaatc ctgttaccagtggctgctgccagtggcgataagtcgtgtcttaccgggttggactcaagacgatagttaccgg ataaggcgcagcggtcgggctgaacggggggttcgtgcacacagcccagcttggagcgaacgacctac accgaactgagatacctacagcgtgagctatgagaaagcgccacgcttcccgaagggagaaaggcgg acaggtatccggtaagcggcagggtcggaacaggagagcgcacgagggagcttccagggggaaacg cctggtatctttatagtcctgtcgggtttcgccacctctgacttgagcgtcgatttttgtgatgctcgtcaggggg cggagcctatggaaaaacgccagcaacgcggcctttttacggttcctggccttttgctggccttttgctcacat gttctttcctgcgttatcccctgattctgtggataaccgtattaccgcctttgagtgagctgataccgctcgccgca gccgaacgaccgagcgcagcgagtcagtgagcgaggaagcggaagagcgcccaatacgcaaaccg cctctccccgcgcgttggccgattcattaatgcagctgcgcgctcgctcgctcactgaggccgcccgggcaa agcccgggcgtcgggcgacctttggtcgcccggcctcagtgagcgagcgagcgcgcagagagggagtg gccaactccatcactaggggttccttgtagttaatgattaacccgccatgctacttatcta In some other embodiments, a pAAV-ND4 transfer plasmid of the disclosure comprises the following functional elements and sequences:

3'UTR Cox10: nt 11-605=595 bp
Coding sequence ND4: nt 618-1997=1380 bp
MTS Cox10: nt 1998-2081=84 bp
HBB2 intron: nt 2124-2616=493 bp
CMV promoter: nt 2624-3283=660 bp
ITR: nt 3327-3454=128 bp
F1 origin: nt 3827-4282=456 bp
Kana R gene: nt 4437-5228=792 bp
COLE1 origin: nt 5443-6057=615 bp
ITR: nt 6279-6408=130 bp.

TABLE 5

Annotated regions within one embodiment of the pAAV-ND4 plasmid

| Name | Start | Stop | Sequence |
|---|---|---|---|
| 3'UTR<br>COX10<br>(polyA<br>sequence<br>underlined) | 11 | 605 | aacatgtggaatccccagtcccagtgcacagcagccgggtcctagctattggtattgttagaa<br>ggactatggttgagaatgtgtggggtggggaaaaccaaaaatgcaggccctggctcagtca<br>ccaggaaggggggtgctccgaggcctttgagggacctgagctcacagaactacagacagca<br>gatcatgaggctcacactttctggccaccaagtgccactctgctgggcatgtggagtgtgcgtg<br>tggtgtggtggtaaggatggaaccaaaagaggaagctgtgtatgtgtaccccatgtgagga<br>ggaagaaacagaatagagggtggggttggaggagagatgtataaagaccctcaaaggga<br>aaaataattcctttttttgtattcactgactgagctgatgcatttcttatttggggagcattttgggtaat<br>atttaaaaaaaaaaaaaactgtcaagtgatcactgggcaccgaattcgtttataatcttgttcta<br>aacccagcaatttctcttcttgtgttccagaattaccacaacatgctcgcctggcagcggaggg<br>aaaggggcggtgggcgtcccagtgctc |
| ND4 | 618 | 1997 | tcaggatgagaaaccagtgataatgtctgggttcagggacagcagcaggatgggagacag<br>atgcataaacatcagggtgttctctctggtgaatgagggcttcatgttattaatgtggtgagtcagt<br>gagccccactgggtagtggtaaacatgtacaggctgtagagggctgtgaccagcatgttcag<br>tcctgtcaggagcagggtgatgttgctccaggagaatgttgtcaccagcactgacagctctcc<br>cagcaggttaattgtagggggcagagccaggttggccagactagccaggagccaccagaa<br>agccatcagtgggagcagggtctggagcccctgactcaggatcataattcttgagtgagttcttt<br>catagttgctatttgccaggcagaacaggaggctgctggtcagcccatgagcaatcatgagg<br>atcactgccccagtaaaggaccagggtgtctgaatcagaatggcagtcaccaccagtgcca<br>tgtggctgatggagctgtaagcaatcaggctcttgaggtcagtctgcctgagacagatggagc<br>tggtcatgatcataccccagaggctcagaaccaggaaagggtaagccatgtgctttgtcaga<br>gggttcaggatcagggtgagcctcatcataccataaccacccagcttcaggaggacagcag<br>ccaggaccatggagccagctattggagcttccacatgagccttggggagccagaggtgcag<br>gccatagaggggcatcttcaccataaaggccattgtataagccagccacatcaggttgtttgc<br>ccaggagttactcagctcctgggcagtcagagtcagcaggaggatgttcaggctacccagtg<br>tgttgtgggtatagatcagtgcaatcagcaggggcagtgagcccaccagtgtataaaagaga<br>aagtaggtgcctgcattcagcctctcaggctgatttccccacctagtgatgatggccagggttg<br>ggatgagagtggtctcaaagaagatatagaacatgatcagctcagtggctgtgaaggtcata<br>atcaggctgatttgcaggctaatgagcatggacaggtacagctttttccttgacagaggctctg<br>agctgaggtgcctctgactggccatgatagtcagaggcagcagccatgtggtcagcatgagc<br>agggggggttgtcaggggatcagaggaaaaggtaggggagcatgaaaagaggttattatta<br>atctggttgaaaaacagcagtgggatgatgctgataatcaggctgtgggttgtggtgttaatcc<br>aaatcatgtgctttttgctcagccatgtgagaggcagcagcatgatggttggcacaatcagcttc<br>agcat |
| MTS Cox10 | 1998 | 2081 | agtcctcctttccaggtaccacacactcccccccacacagccagtcaggagcctggatgaca<br>gtgtatgggggctggcagccat |
| betaglobin<br>intron | 2124 | 2616 | atcccaattctttgccaaagtgatgggccagcacacagaccagcacgttgcccaggagctgt<br>gggaggaagataagaggtatgaacatgattagcaaaagggcctagcttggactcagaata<br>atccagccttatcccaaccataaaataaaagcagaatggtagctggattgtagctgctattagc<br>aatatgaaacctcttacatcagttacaatttatatgcagaaatatttatatgcagaaatattgctatt<br>gccttaacccagaaattatcactgttattctttagaatggtgcaaagaggcatgatacattgtatc<br>attattgccctgaaagaaagagattagggaaagtattagaaataagataaacaaaaaagtat<br>attaaaagaagaaagcatttttttgtgggcctatagactctataggcggtacttacgtcactcttgg<br>cacggggaatccgcgttccaatgcaccgttcccggccgggattcg |
| CMV<br>promoter | 2624 | 3283 | ggaggctggatcggtcccggtgtcttctatggaggtcaaaacagcgtggatggcgtctccagg<br>cgatctgacggttcactaaacgagctctgcttatatagacctcccaccgtacacgcctaccgcc<br>catttgcgtcaatggggcggagttgttacgacattttggaaagtcccgttgattttggtgccaaaa<br>caaactcccattgacgtcaatggggtggagacttggaaatccccgtgagtcaaaccgctatc<br>cacgcccattgatgtactgccaaaaccgcatcaccatggtaatagcgatgactaatacgtag<br>atgtactgccaagtaggaaagtcccataaggtcatgtactgggcataatgccaggcgggcca<br>tttaccgtcattgacgtcaatagggggcgtacttggcatatgatacacttgatgtactgccaagt<br>gggcagtttaccgtaaatactccacccattgacgtcaatggaaagtccctattggcgttactatg<br>ggaacatacgtcattattgacgtcaatgggcgggggtcgttgggcggtcagccaggcgggcc<br>atttaccgtaagttatgtaacgcggaactccatatatgggctatgaactaatgaccccgtaattg<br>attactattaataactagacgcgt |
| 5' ITR | 3327 | 3454 | aggaacccctagtgatggagttggccactccctctctgcgcgctcgctcgctcactgaggccg<br>ggcgaccaaaggtcgcccgacgcccgggctttgcccgggcggcctcagtgagcgagcga<br>gcgcgc |
| F1 origin | 3827 | 4282 | acgcgccctgtagcggcgcattaagcgcggcgggtgtggtggttacgcgcagcgtgaccgc<br>tacacttgccagcgccctagcgcccgctcctttcgctttcttcccttcctttctcgccacgttcgccg<br>gctttccccgtcaagctctaaatcgggggctccctttagggttccgatttagtgctttacggcacct<br>cgaccccaaaaaacttgattagggtgatggttcacgtagtgggccatcgccctgatagacggt |

TABLE 5-continued

| Annotated regions within one embodiment of the pAAV-ND4 plasmid | | | |
|---|---|---|---|
| Name | Start | Stop | Sequence |
| | | | ttttcgccctttgacgttggagtccacgttctttaatagtggactcttgttccaaactggaacaaca ctcaaccctatctcggtctattcttttgatttataagggattttgccgatttcggcctattggttaaaaa atgagctgatttaacaaaaatttaacgcgaattttaacaaaatattaacgcttacaattt |
| Kana R gene | 4437 | 5228 | attgaacaagatggattgcacgcaggttctccggccgcttgggtggagaggctattcggctat gactgggcacaacagacaatcggctgctctgatgccgccgtgttccggctgtcagcgcaggg gcgcccggttctttttgtcaagaccgacctgtccggtgccctgaatgaactgcaagacgaggc agcgcggctatcgtggctggccacgacgggcgttccttgcgcagctgtgctcgacgttgtcact gaagcgggaagggactggctgctattgggcgaagtgccggggcaggatctcctgtcatctca ccttgctcctgccgagaaagtatccatcatggctgatgcaatgcggcggctgcatacgcttgat ccggctacctgcccattcgaccaccaagcgaaacatcgcatcgagcgagcacgtactcgg atggaagccggtcttgtcgatcaggatgatctggacgaagagcatcaggggctcgcgccag ccgaactgttcgccaggctcaaggcgagcatgcccgacggcgaggatctcgtcgtgaccca tggcgatgcctgcttgccgaatatcatggtggaaaatggccgcttttctggattcatcgactgtgg ccggctgggtgtggcggaccgctatcaggacatagcgttggctacccgtgatattgctgaaga gcttggcggcgaatgggctgaccgcttcctcgtgctttacggtatcgccgctcccgattcgcag cgcatcgccttctatcgccttcttgacgagttcttctga |
| ColE1 origin | 5443 | 6057 | aaaggatcttcttgagatcctttttttctgcgcgtaatctgctgcttgcaaacaaaaaaaccaccg ctaccagcggtggtttgtttgccggatcaagagctaccaactctttttccgaaggtaactggcttc agcagagcgcagataccaaatactgtccttctagtgtagccgtagttaggccaccacttcaag aactctgtagcaccgcctacatacctcgctctgctaatcctgttaccagtggctgctgccagtgg cgataagtcgtgtcttaccgggttggactcaagacgatagttaccggataaggcgcagcggtc gggctgaacggggggttcgtgcacacagcccagcttggagcgaacgacctacaccgaact gagatacctacagcgtgagctatgagaaagcgccacgcttcccgaagggagaaaggcgg acaggtatccggtaagcggcagggtcggaacaggagagcgcacgagggagcttccagg gggaaacgcctggtatctttatagtcctgtcgggtttcgccacctctgacttgagcgtcgatttttgt gatgctcgtcaggggggcggagcctatggaaaaacgccagcaacgcg |
| 3' ITR | 6279 | 6408 | ctgcgcgctcgctcgctcactgaggccgcccgggcaaagcccgggcgtcgggcgacctttg gtcgcccggcctcagtgagcgagcgagcgcgcagagagggagtggccaactccatcacta ggggttcct |

In some embodiments, a pAAV-ND4 transfer plasmid of the disclosure comprises:

(SEQ ID NO: 23)

gctcggtccgaacatgtggaatccccagtcccagtgcacagcagccgggtcctagctattggtattgttaga aggactatggttgagaatgtgtggggtggggaaaaccaaaaatgcaggccctggctcagtcaccaggaa gggggtgctccgaggcctttgagggacctgagctcacagaactacagacagcagatcatgaggctcaca ctttctggccaccaagtgccactctgctgggcatgtggagtgtgcgtgtggtgtggtggtaaggatggaacca aaagaggaagctgtgtatgtgtaccccccatgtgaggaggaagaaacagaatagagggtggggttggag gagagatgtataaagaccctcaaagggaaaaataattccttttttgtattcactgactgagctgatgcatttctt atttggggagcattttgggtaatatttaaaaaaaaaaaaaactgtcaagtgatcactgggcaccgaattcgttt ataatcttgttctaaacccagcaatttctcttcttgtgttccagaattaccacaacatgctcgcctggcagcgga gggaaaggggcggtgggcgtcccagtgctcagatctctcgagtcaggatgagaaaccagtgataatgtct gggttcagggacagcagcaggatgggagacagatgcataaacatcagggtgttctctctggtgaatgagg gcttcatgttattaatgtggtgagtcagtgagccccactgggtagtggtaaacatgtacaggctgtagagggc tgtgaccagcatgttcagtcctgtcaggagcagggtgatgttgctccaggagaatgttgtcaccagcactga cagctctcccagcaggttaattgtagggggcagagccaggttggccagactagccaggagccaccagaa agccatcagtgggagcagggtctggagcccctgactcaggatcataattcttgagtgagttctttcatagttgc tatttgccaggcagaacaggaggctgctggtcagcccatgagcaatcatgaggatcactgccccagtaaa ggaccagggtgtctgaatcagaatggcagtcaccaccagtgccatgtggctgatggagctgtaagcaatc aggctcttgaggtcagtctgcctgagacagatggagctggtcatgatcataccccagaggctcagaaccag gaaagggtaagccatgtgctttgtcagagggttcaggatcagggtgagcctcatcataccataaccaccca -continued gcttcaggaggacagcagccaggaccatggagccagctattggagcttccacatgagccttggggagcc agaggtgcaggccatagaggggcatcttcaccataaaggccattgtataagccagccacatcaggttgttt gcccaggagttactcagctcctgggcagtcagagtcagcaggaggatgttcaggctacccagtgtgttgtg ggtatagatcagtgcaatcagcaggggcagtgagcccaccagtgtataaaagagaaagtaggtgcctgc attcagcctctcaggctgatttccccacctagtgatgatggccagggttgggatgagagtggtctcaaagaa gatatagaacatgatcagctcagtggctgtgaaggtcataatcaggctgatttgcaggctaatgagcatgga caggtacagctttttccttgacagaggctctgagctgaggtgcctctgactggccatgatagtcagaggcagc agccatgtggtcagcatgagcagggggggttgtcaggggatcagaggaaaaggtaggggagcatgaaaa gaggttattattaatctggttgaaaaacagcagtgggatgatgctgataatcaggctgtgggttgtggtgttaat ccaaatcatgtgctttttgctcagccatgtgagaggcagcagcatgatggttggcacaatcagcttcagcata gtcctcctttccaggtaccacacactcccccccacacagccagtcaggagcctggatgacagtgtatgggg gctggcagccatgtcgactctagaggatccccggggaattcaatcgatgttcgaatcccaattctttgccaaa gtgatgggccagcacacagaccagcacgttgcccaggagctgtgggaggaagataagaggtatgaaca tgattagcaaaagggcctagcttggactcagaataatccagccttatcccaaccataaaataaaagcaga atggtagctggattgtagctgctattagcaatatgaaacctcttacatcagttacaatttatatgcagaaatattt atatgcagaaatattgctattgccttaacccagaaattatcactgttattctttagaatggtgcaaagaggcatg atacattgtatcattattgccctgaaagaaagagattagggaaagtattagaaataagataaacaaaaaag tatattaaaagaagaaagcatttttttgtgggcctatagactctataggcggtacttacgtcactcttggcacggg gaatccgcgttccaatgcaccgttcccggccgggattcgaatccgcggaggctggatcggtcccggtgtctt ctatggaggtcaaaacagcgtggatggcgtctccaggcgatctgacggttcactaaacgagctctgcttata tagacctcccaccgtacacgcctaccgcccatttgcgtcaatggggcggagttgttacgacattttggaaagt cccgttgattttggtgccaaaacaaactcccattgacgtcaatggggtggagacttggaaatccccgtgagtc aaaccgctatccacgcccattgatgtactgccaaaaccgcatcaccatggtaatagcgatgactaatacgt agatgtactgccaagtaggaaagtcccataaggtcatgtactgggcataatgccaggcgggccatttaccg tcattgacgtcaatagggggcgtacttggcatatgatacacttgatgtactgccaagtgggcagtttaccgtaa atactccacccattgacgtcaatggaaagtccctattggcgttactatgggaacatacgtcattattgacgtca atgggcgggggtcgttgggcggtcagccaggcgggccatttaccgtaagttatgtaacgcggaactccata tatgggctatgaactaatgaccccgtaattgattactattaataactagacgcgtgcggccgtagataagtag catggcgggttaatcattaactacaaggaacccctagtgatggagttggccactccctctctgcgcgctcgct cgctcactgaggccgggcgaccaaaggtcgcccgacgcccgggctttgcccgggcggcctcagtgagc gagcgagcgcgcagctggcgtaatagcgaagaggcccgcaccgatcgcccttcccaacagttgcgcag cctgaatggcgaatggcgattccgttgcaatggctggcggtaatattgttctggatattaccagcaaggccga tagtttgagttcttctactcaggcaagtgatgttattactaatcaaagaagtattgcgacaacggttaatttgcgt gatggacagactcttttactcggtggcctcactgattataaaaacacttctcaggattctggcgtaccgttcctgt ctaaaatccctttaatcggcctcctgtttagctcccgctctgattctaacgaggaaagcacgttatacgtgctcg tcaaagcaaccatagtacgcgccctgtagcggcgcattaagcgcggcgggtgtggtggttacgcgcagcg tgaccgctacacttgccagcgccctagcgcccgctcctttcgctttcttcccttcctttctcgccacgttcgccgg ctttccccgtcaagctctaaatcgggggctccctttagggttccgatttagtgctttacggcacctcgaccccaa -continued

```
aaaacttgattagggtgatggttcacgtagtgggccatcgccctgatagacggtttttcgccctttgacgttgga

gtccacgttctttaatagtggactcttgttccaaactggaacaacactcaaccctatctcggtctattcttttgattt

ataagggattttgccgatttcggcctattggttaaaaaatgagctgatttaacaaaaatttaacgcgaattttaa

caaaatattaacgcttacaatttaggtggcacttttcggggaaatgtgcgcggaacccctatttgtttatttttcta

aatacattcaaatatgtatccgctcatgagacaataaccctgataaatgcttcaataatagcacctagatcaa

gagacaggatgaggatcgtttcgcatgattgaacaagatggattgcacgcaggttctccggccgcttgggtg

gagaggctattcggctatgactgggcacaacagacaatcggctgctctgatgccgccgtgttccggctgtca

gcgcaggggcgcccggttctttttgtcaagaccgacctgtccggtgccctgaatgaactgcaagacgaggc

agcgcggctatcgtggctggccacgacgggcgttccttgcgcagctgtgctcgacgttgtcactgaagcgg

gaagggactggctgctattgggcgaagtgccggggcaggatctcctgtcatctcaccttgctcctgccgaga

aagtatccatcatggctgatgcaatgcggcggctgcatacgcttgatccggctacctgcccattcgaccacc

aagcgaaacatcgcatcgagcgagcacgtactcggatggaagccggtcttgtcgatcaggatgatctgga

cgaagagcatcaggggctcgcgccagccgaactgttcgccaggctcaaggcgagcatgcccgacggcg

aggatctcgtcgtgacccatggcgatgcctgcttgccgaatatcatggtggaaaatggccgcttttctggattc

atcgactgtggccggctgggtgtggcggaccgctatcaggacatagcgttggctacccgtgatattgctgaa

gagcttggcggcgaatgggctgaccgcttcctcgtgctttacggtatcgccgctcccgattcgcagcgcatcg

ccttctatcgccttcttgacgagttcttctgaattattaacgcttacaatttcctgatgcggtattttctccttacgcat

ctgtgcggtatttcacaccgcatcaggtggcacttttcggggaaatgtgcgcggaacccctatttgtttatttttct

aaatacattcaaatatgtatccgctcatgaccaaaatcccttaacgtgagttttcgttccactgagcgtcagac

cccgtagaaaagatcaaaggatcttcttgagatcctttttttctgcgcgtaatctgctgcttgcaaacaaaaaa

accaccgctaccagcggtggtttgtttgccggatcaagagctaccaactctttttccgaaggtaactggcttca

gcagagcgcagataccaaatactgttcttctagtgtagccgtagttaggccaccacttcaagaactctgtagc

accgcctacatacctcgctctgctaatcctgttaccagtggctgctgccagtggcgataagtcgtgtcttaccg

ggttggactcaagacgatagttaccggataaggcgcagcggtcgggctgaacggggggttcgtgcacac

agcccagcttggagcgaacgacctacaccgaactgagatacctacagcgtgagctatgagaaagcgcc

acgcttcccgaagggagaaaggcggacaggtatccggtaagcggcagggtcggaacaggagagcgc

acgagggagcttccagggggaaacgcctggtatctttatagtcctgtcgggtttcgccacctctgacttgagc

gtcgatttttgtgatgctcgtcaggggggcggagcctatggaaaaacgccagcaacgcggcctttttacggtt

cctggccttttgctggccttttgctcacatgttctttcctgcgttatcccctgattctgtggataaccgtattaccgcct

ttgagtgagctgataccgctcgccgcagccgaacgaccgagcgcagcgagtcagtgagcgaggaagcg

gaagagcgcccaatacgcaaaccgcctctccccgcgcgttggccgattcattaatgcagctgcgcgctcg

ctcgctcactgaggccgcccgggcaaagcccgggcgtcgggcgacctttggtcgcccggcctcagtgag

cgagcgagcgcgcagagagggagtggccaactccatcactaggggttccttgtagttaatgattaacccgc

catgctacttatctac
```

In some embodiments, a pAAV-ND4 transfer plasmid of the disclosure comprises a Kanamycin resistance gene to allow for antibiotic selection. In some embodiments, a pAAV-ND4 transfer plasmid of the disclosure comprises an f1 origin of replication sequence to allow for replication of the plasmid. In some embodiments, a pAAV-ND4 transfer plasmid of the disclosure comprises a ColE1 origin of replication sequence to allow for replication of plasmid.

Thus, in some embodiments, a pAAV-ND4 transfer plasmid of the disclosure further comprises:

(SEQ ID No: 8)

```
acgcgccctgtagcggcgcattaagcgcggcgggtgtggtggttacgcgc

agcgtgaccgctacacttgccagcgccctagcgcccgctcctttcgcttt

cttcccttcctttctcgccacgttcgccggctttccccgtcaagctctaa

atcgggggctccctttagggttccgatttagtgctttacggcacctcgac
```

-continued

```
cccaaaaaacttgattagggtgatggttcacgtagtgggccatcgccctg

atagacggtttttcgccctttgacgttggagtccacgttctttaatagtg

gactcttgttccaaactggaacaacactcaaccctatctcggtctattct

tttgatttataagggattttgccgatttcggcctattggttaaaaaatga

gctgatttaacaaaaatttaacgcgaattttaacaaaatattaacgctta

caattt,
```

(ii) a Kanamycin resistance gene sequence comprising:

```
                                          (SEQ ID No: 9)
attgaacaagatggattgcacgcaggttctccggccgcttgggtggagag

gctattcggctatgactgggcacaacagacaatcggctgctctgatgccg

ccgtgttccggctgtcagcgcaggggcgcccggttctttttgtcaagacc

gacctgtccggtgccctgaatgaactgcaagacgaggcagcgcggctatc

gtggctggccacgacgggcgttccttgcgcagctgtgctcgacgttgtca

ctgaagcgggaagggactggctgctattgggcgaagtgccggggcaggat

ctcctgtcatctcaccttgctcctgccgagaaagtatccatcatggctga

tgcaatgcggcggctgcatacgcttgatccggctacctgcccattcgacc

accaagcgaaacatcgcatcgagcgagcacgtactcggatggaagccggt

cttgtcgatcaggatgatctggacgaagagcatcaggggctcgcgccagc

cgaactgttcgccaggctcaaggcgagcatgcccgacggcgaggatctcg

tcgtgacccatggcgatgcctgcttgccgaatatcatggtggaaaatggc

cgcttttctggattcatcgactgtggccggctgggtgtggcggaccgcta

tcaggacatagcgttggctacccgtgatattgctgaagagcttggcggcg

aatgggctgaccgcttcctcgtgctttacggtatcgccgctcccgattcg

cagcgcatcgccttctatcgccttcttgacgagttcttctga,
```

and (iii) a ColE1 origin of replication sequence comprising:

```
                                         (SEQ ID No: 10)
aaaggatcttcttgagatcctttttttctgcgcgtaatctgctgcttgca

aacaaaaaaaccaccgctaccagcggtggtttgtttgccggatcaagagc

taccaactctttttccgaaggtaactggcttcagcagagcgcagatacca

aatactgtccttctagtgtagccgtagttaggccaccacttcaagaactc

tgtagcaccgcctacatacctcgctctgctaatcctgttaccagtggctg

ctgccagtggcgataagtcgtgtcttaccgggttggactcaagacgatag

ttaccggataaggcgcagcggtcgggctgaacggggggttcgtgcacaca

gcccagcttggagcgaacgacctacaccgaactgagatacctacagcgtg

agctatgagaaagcgccacgcttcccgaagggagaaaggcggacaggtat

ccggtaagcggcagggtcggaacaggagagcgcacgagggagcttccagg

gggaaacgcctggtatctttatagtcctgtcgggtttcgccacctctgac

ttgagcgtcgatttttgtgatgctcgtcaggggggcggagcctatggaaa

aacgccagcaacgcg.
```

Generation of a pAAV-ND4 transfer plasmid of the disclosure can be accomplished using a suitable genetic engineering technique known in the art (see, e.g., Green, et al., Molecular Cloning: A Laboratory Manual, 4th edition, Cold Spring Harbor Press, (2012)).

Figure 2:
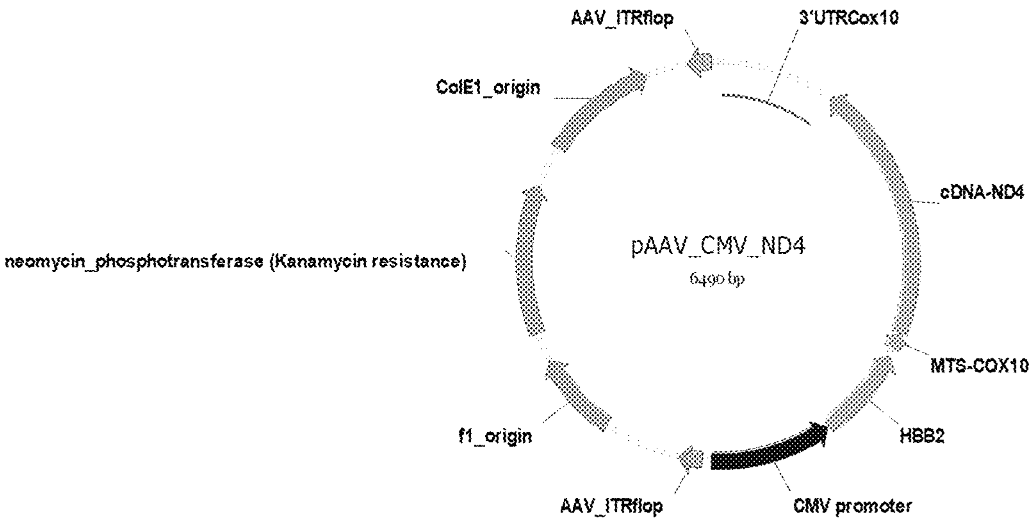
FIG. 2 depicts the structure of an embodiment of a pAAV-ND4 plasmid of the disclosure.

In some embodiments, a recombinant AAV vector of the disclosure is produced by tri-transfection in a transitory packaging cell line with (i) a pAAV-ND4 transfer plasmid of the disclosure (e.g., that shown in FIG. 2), (ii) a replcap plasmid providing to host cells the genetic material encoding for the synthesis of essential proteins (e.g., as non-limiting examples, enzymes and structural proteins) involved in the production of the AAV2/2 particle, and (iii) an adenovirus helper plasmid providing the helper function to induce the expression of rep/cap gene.

In some embodiments, the packaging cell line comprises the human embryonic kidney 293 (HEK 293) cell line.

Figure 3:
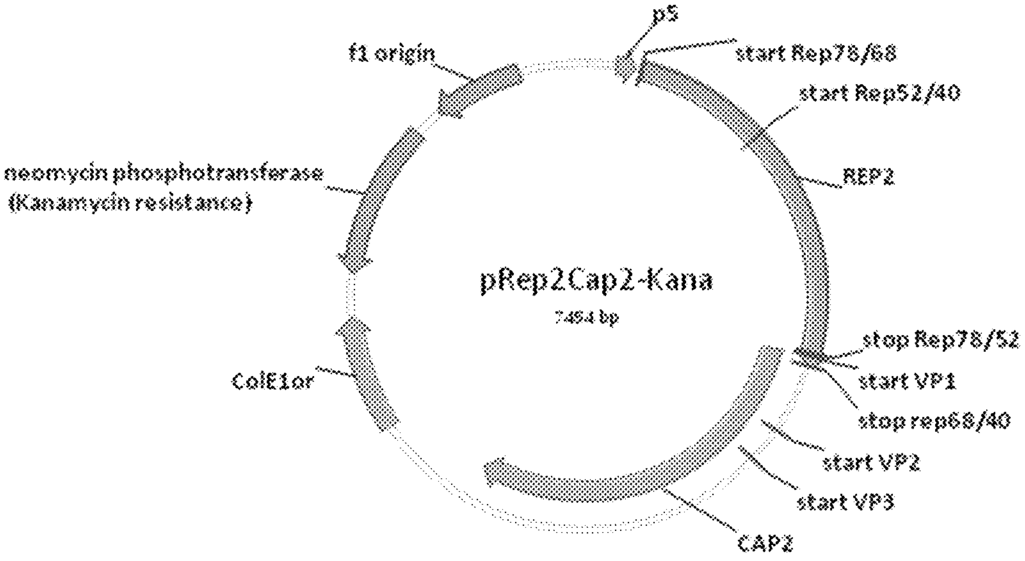
FIG. 3 depicts an embodiment of a pRep2Cap2 plasmid of the disclosure.

In some embodiments, the rep/cap plasmid is pRep2Cap2 plasmid. In some embodiments, the rep/cap plasmid is pRep2Cap2 plasmid comprising the following elements (FIG. 3):

i. a rep sequence from AAV2/2 serotype (nt 281-2212, 1932 bp), ii. a cap sequence from AAV2/2 serotype (nt 2163-4370; 2208 bp), iii. a Kanamycin resistance gene (nt 5712-6506, complementary; 795 bp), and iv. a prokaryotic origin of replication (nt 4896-5496; 601 bp) and phage f1 origin of replication (nt 6658-7113; 456 bp).

Figure 4:
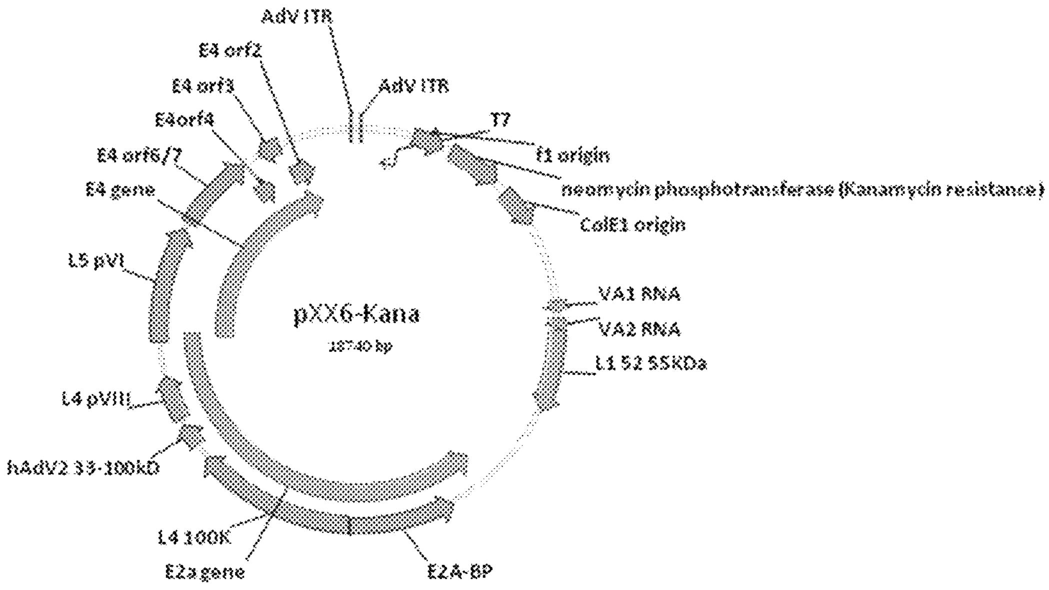
FIG. 4 depicts an embodiment of an adenovirus helper pXX6 plasmid of the disclosure.

In some embodiments, the adenovirus helper plasmid is pXX6 plasmid. In some embodiments, the adenovirus helper plasmid is pXX6 plasmid comprising the following elements (FIG. 4):

i. adenoviral ITRs: (nt 1-85 and 18638-18732), ii. a Kanamycin resistance gene (nt 1402-2196, 795 bp), iii. a prokaryotic origin of replication (nt 2411-3025; 615 bp) and phage f1 origin of replication (nt 795-1250; 456 bp), and iv. 13 specific adenoviral sequences (from VA1 RNA sequence to E4orf2 sequence, nt 4259-17916).

Patients suffering from LHON and treated with the recombinant vectors disclosed herein may receive therapeutic benefit, e.g., by an improvement in visual acuity. The term "treatment" as used herein, is defined as the application or administration of a therapeutic agent to a subject, who has a disease, a symptom of disease or a predisposition toward a disease, with the purpose to cure, heal, alleviate, relieve, alter, remedy, ameliorate, improve, or affect the disease, one or more symptoms of the disease, or the predisposition toward the disease. As long as the compositions of the disclosure either alone or in combination with another therapeutic agent cure, heal, alleviate, relive, alter, remedy, ameliorate, improve or affect at least one symptom of LHON being treated, as compared to that symptom in the absence of treatment, the result is considered a treatment of the underlying disorder regardless of whether all the symptoms of the disorder are cured, healed, alleviated, relieved, altered, remedied, ameliorated, improved or affected or not. Treatment may be achieved using an "effective amount" of a therapeutic agent, which shall be understood to embrace partial and complete treatment, e.g., partial or complete curing, healing, alleviating, relieving, altering, remedying, ameliorating, improving, or affecting the disease, one or more symptoms of the disease, or the predisposition toward the disease. An "effective amount" of may be determined empirically. Likewise, a "therapeutically effective amount" is a concentration or which is effective for achieving a stated therapeutic effect.

In one embodiment, the term "treating" comprises the step of administering an effective dose, or effective multiple doses, of a composition comprising a nucleic acid, a vector, a recombinant virus, or a pharmaceutical composition as disclosed herein, to an animal (including a human being) in need thereof. If the dose is administered prior to development of a disorder/disease, the administration is prophylactic. If the dose is administered after the development of a disorder/disease, the administration is therapeutic. In embodiments, an effective dose is a dose that detectably alleviates (either eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. The term encompasses but does not require complete treatment (i.e., curing) and/or prevention.

In some embodiments, the titer of recombinant vector administered is measured in viral genomes (vg). In some embodiments, the titer of recombinant vector administered is measured by quantitative polymerase chain reaction (qPCR). In some embodiments, the titer of recombinant vector administered is measured by digital droplet PCR (ddPCR). In some embodiments, recombinant AAV vector is administered intravitreally at an amount of about $1.0\times10^{9}$ to $1.0\times10^{12}$ vg per eye. In some embodiments, recombinant AAV vector is administered intravitreally at an amount of about $5.0\times10^{9}$ to $5\times10^{11}$ vg per eye. In some embodiments, recombinant AAV vector is administered intravitreally at an amount of about $1.0\times10^{10}$ to $1\times10^{11}$ vg per eye. In some embodiments, recombinant AAV vector is administered intravitreally at an amount of about $9\times10^{110}$ vg per eye. The titer of recombinant vector may be measured by PCR from primers that hybridize within the recombinant vector. Examples of primers include but are not limited to: CTCCATCACTAGGGGTTCCTTG AAV22mers.F (SEQ ID NO: 19) GTAGATAAGTAGCATGGC AAV18mers.R (SEQ ID NO: 20) TAGTTAATGATTAACCC AAV_MGB.P (SEQ ID NO: 21)

In some embodiments, the recombinant vector of the disclosure, e.g. an AAV, serotype 2, (rAAV) encoding the gene of the human NADH dehydrogenase 4 (ND4), comprises:

a 3'UTR Cox10 sequence comprising SEQ ID NO:1,
a nucleic acid sequence encoding an ND4 polypeptide comprising SEQ ID NO: 13, and
a nucleic acid sequence encoding an MTS Cox10 polypeptide comprising SEQ ID NO: 11,
is administered at an effective dose into a patient in need thereof. In some embodiments, the patient suffers from LHON.

In some embodiments, the recombinant vector of the disclosure, e.g. an AAV, serotype 2, (rAAV) encoding the gene of the human NADH dehydrogenase 4 (ND4), comprises:

a 3'UTR Cox10 sequence comprising SEQ ID NO:1,
a nucleic acid sequence encoding an ND4 polypeptide comprising SEQ ID NO: 13, and
a nucleic acid sequence encoding an MTS Cox10 polypeptide comprising SEQ ID NO: 12,
is administered at an effective dose into a patient in need thereof. In some embodiments, the patient suffers from LHON.

In some embodiments, the recombinant vector of the disclosure, e.g. an AAV, serotype 2, (rAAV) encoding the gene of the human NADH dehydrogenase 4 (ND4), comprises:

a 3'UTR Cox10 sequence comprising SEQ ID NO: 14,
a nucleic acid sequence encoding an ND4 polypeptide comprising SEQ ID NO: 13, and
a nucleic acid sequence encoding an MTS Cox10 polypeptide comprising SEQ ID NO: 11,
is administered at an effective dose into a patient in need thereof. In some embodiments, the patient suffers from LHON.

In some embodiments, the recombinant vector of the disclosure, e.g. an AAV, serotype 2, (rAAV) encoding the gene of the human NADH dehydrogenase 4 (ND4), comprises:

a 3'UTR Cox10 sequence comprising SEQ ID NO: 14,
a nucleic acid sequence encoding an ND4 polypeptide comprising SEQ ID NO: 13, and
a nucleic acid sequence encoding an MTS Cox10 polypeptide comprising SEQ ID NO: 12,
is administered at an effective dose into a patient in need thereof. In some embodiments, the patient suffers from LHON.

Onset of LHON may be determined by the presence of symptoms. In some embodiments, the recombinant vectors are administered to patients with disease onset of less than 9 months, e.g., 6 to 9 months, 3 to 6 months, or 1 to 3 months. In some embodiments, the recombinant vectors are administered to patients with disease onset of more than 9 months, e.g., for 12 months, for 2 years, or for 3 years. In some embodiments, the patient shows one or more symptoms of LHON, e.g., loss in visual acuity.

A scale to measure visual acuity in a patient may be expressed as the (decadic) logarithm of the minimum angle of resolution (MAR) (Bailey I L, Lovie J E. I, Am. J. Optom. Physiol. Opt., 53 (11): 740-745 (1976)). The LogMAR scale converts the geometric sequence of a traditional chart to a linear scale. It measures visual acuity loss: positive values indicate vision loss, while negative values denote normal or better visual acuity. In some embodiments, visual acuity of a patient suffering from LHON is measured by the LogMar Scale. In some embodiments, visual acuity of a patient suffering from LHON is measured by the Snellen Scale.

Another commonly used measure of visual acuity is the Early Treatment Diabetic Retinopathy Study (ETDRS) visual acuity charts, which is capable of quantifying visual acuity to very low vision levels (Ferris et al., Am. J. Opthalmol., 94:91-96 (1982)). In some embodiments, visual acuity of a patient suffering from LHON is measured by the ETDRS charts.

Contrast is determined by the difference in the color and brightness of an object and other objects within the same field of view. Patients suffering from LHON may have reduced sensitivity for contrast. Another scale that measures visual acuity may be the Pelli-Robson contrast sensitivity chart (Pelli et al., Clin. Vision Sci., 2 (3): 187-199 (1988). In some embodiments, visual acuity of a patient suffering from LHON is measured by a Pelli Robson chart.

In some embodiments, treatment is administered in patients with visual acuity at before treatment e.g., at baseline, of <2.0 LogMAR, e.g., <1.8, <1.6, <1.4, <1.2, <1.0, or <0.8 LogMAR. In some embodiments, treatment is administered in patients with visual acuity at before treatment e.g., at baseline, of at least 3 letters, e.g., at least 4, 5, 6, 7, 8, 9, 10, 11, or 12 letters.

Efficacy or response to treatment may be measured by reversal or amelioration of disease symptoms. In some embodiments, a baseline visual acuity is measured before administration of treatment. In some embodiments, efficacy or response to treatment is measured by an increase in visual acuity. In some embodiments, efficacy or response to treatment is measured by an increase in visual acuity after treatment compared to the baseline before treatment. In some embodiments, efficacy or response to the treatment is measured by the difference between ETDRS scores before and after treatment. In some embodiments, efficacy or response to the treatment is measured by a difference of at least +5.0 ETDRS score, e.g., at least +6.0, +7.0, +8.0, +9.0, +10.0, +11.0, +12.0, +13.0, +14.0, +15.0, or +16.0 after treatment compared to baseline. In some embodiments, efficacy or response to the treatment is measured by a difference of at least 0.05 LogMAR, e.g., at least 0.1, 0.2, 0.3, 0.4, 0.5, 0.6, 0.7, 0.8, 0.9, or 1.0 after treatment compared to baseline.

As disclosed herein, and without being bound by theory, patients who respond to treatment with a recombinant vector of the disclosure (e.g. patients for which an increase in visual acuity was observed) may include those patients with a disease duration (e.g., vision loss) at baseline of less than 9 months, for example, of 6 to 9 months, and/or with visual acuity at baseline of <1.6 LogMAR. In some embodiments, a criterion (e.g., a disease duration as measured by vision loss at baseline of less than 9 months, or of 6 to 9 months, and/or visual acuity at baseline of <1.6 LogMAR) may be used to identify a patient sub-population that is expected to respond better to treatment with recombinant vector of the disclosure (e.g., a patient population for which an increase in visual acuity may be expected).

The present disclosure further describes the use of recombinant vector encoding a human NADH dehydrogenase 4 (ND4) polypeptide and comprising (i) a nucleic acid sequence encoding a MTS Cox10 sequence comprising SEQ ID NO: 11, (ii) a nucleic acid sequence encoding a NADH dehydrogenase 4 (ND4) polypeptide comprising SEQ ID No: 13, and (iii) a 3'UTR Cox10 sequence comprising SEQ ID NO: 14 (or its reverse complement SEQ ID NO: 1), in the treatment of Leber Hereditary Optic Neuroretinopathy (LHON) for a group of patients with (i) disease duration at baseline of less than 9 months (e.g. 6 to 9 months) and/or (ii) visual acuity at baseline of less than 1.6 LogMAR.

The present disclosure also describes a method of treating patients suffering from LHON, with (i) disease duration at baseline of less than 9 months (e.g. 6 to 9 months) and/or (ii) visual acuity at baseline of less than 1.6 LogMAR, comprising administering an effective amount of a recombinant vector encoding a human NADH dehydrogenase 4 (ND4) polypeptide and comprising (i) a nucleic acid sequence encoding a MTS Cox10 sequence comprising SEQ ID NO: 11, (ii) a nucleic acid sequence encoding NADH dehydrogenase 4 (ND4) polypeptide comprising SEQ ID No: 13, and (iii) a 3'UTR Cox10 sequence comprising SEQ ID NO: 14 (or its reverse complement SEQ ID NO: 1).

The present disclosure is further illustrated by the following examples that should not be construed as limiting. The contents of all references, patents, and published patent applications cited throughout this application, as well as the Figures, are incorporated herein by reference in their entirety for all purposes.

Example 1

The safety and efficacy of a vector, as disclosed herein, comprising a recombinant adeno-associated virus (AAV) vector, serotype 2, containing the human mitochondrial ND4 gene (rAAV2/2-ND4) ("Vector A") in patients having Leber Hereditary Optic Neuroretinopathy was investigated.

Patients participating in the study suffered vision loss for a duration of greater than six months up to one year. Enrolled subjects had a confirmed G11778A mutation in the ND4 gene. Enrolled subjects also had baseline vision greater than or equal to Count Fingers.

Each patient had one eye randomly selected to receive a single injection of Vector A, while the other eye received a sham injection. In a first patient group, the right eye (OD) was treated with Vector A, while the left eye (OS) was sham-treated. In a second patient group, the right eye (OD) was sham-treated, while the left eye (OS) was treated with Vector A.

Treatment with Vector A was by means of intravitreal injection containing $9\times10^{10}$ viral genomes in 90 μL balanced salt solution plus 0.001% Pluronic F68®. Sham-treatment comprised intravitreal injection that was performed by applying pressure to the eye at the location of a typical intravitreal injection procedure, using the blunt end of a syringe without a needle.

Comparisons were made between vector A-treated eyes versus sham-treated eyes in changes from baseline (pre-study) point and week 48 of LogMAR acuity derived from the number of letters patients read on the ETDRS chart at week 48 post-treatment. In a separate mode of comparison, the better-seeing eye of each patient was determined at visit 1, prior to randomization, based on vision testing results. Better-seeing eyes that received Vector A were compared to better-seeing eyes that received the sham injection. A similar analysis was performed for the worse-seeing eyes. As would be understood by a person having ordinary skill in the art, ETDRS (Early Treatment Diabetic Retinopathy Study) is a measurement of visual acuity that is capable of quantifying visual acuity to very low vision levels.

As would be understood by a person having ordinary skill in the art, MAR refers to minimum angle of resolution (in minutes of arc) of the stroke width of the smallest letter recognized. The logarithm of MAR (LogMAR) and, by way of a non-limiting example, LogMAR charts, are used to determine visual acuity. (Johnston, A., *Association of Contact Lens Manufacturers Year Book* 2011-2016, pp. 38-39 (2016)).

Patient demographics at baseline are presented in Table 6.

TABLE 6

| Statistic | Study |
|---|---|
| N subjects | 37 |
| Demographics | |
| N males (%) | 29 (78.4) |
| Mean age - years (SD) | 34.2 (15.2) |
| Median age - years (range) | 30 (15, 67) |
| Vision loss duration (VLD) | |
| Eyes with available data | 74 |
| Mean VLD - days (SD) | 270.9 (59.4) |
| Median VLD - days (range) | 262 (181, 364) |
| Simultaneous bilateral onset | |
| N subjects (%) | 7 (19%) |

SD: standard deviation,
VLD: vision loss duration

Data pertaining to patient visual acuity at baseline are presented in Table 7.

TABLE 7

| Statistic | Study | Treated eyes | Sham eyes |
|---|---|---|---|
| N subjects | 37 | | |
| N eyes with available data | 74 | | |
| All eyes | | | |
| Mean LogMAR (SD) | 1.6 (0.4) | 1.66 (0.5) | 1.55 (0.42) |
| Median LogMAR (range) | 1.6 (0.7, 3.2) | 1.6 (0.8, 3.17) | 1.5 (0.7, 2.81) |
| Best-seeing eyes | | | |
| Mean LogMAR (SD) | 1.5 (0.4) | 1.44 (0.33) | 1.50 (0.38) |
| Median LogMAR (range) | 1.5 (0.7, 2.2) | 1.45 (0.8, 2.09) | 1.50 (0.7, 2.22) |
| Worst-seeing eyes | | | |
| Mean LogMAR (SD) | 1.7 (0.5) | 1.84 (0.55) | 1.61 (0.48) |
| Median LogMAR (range) | 1.6 (0.8, 3.2) | 1.6 (0.8, 3.17) | 1.55 (0.9, 2.81) |

At 48 weeks, a favorable safety profile of Vector A was reported. 75% of adverse events (AEs) were ocular. 50% of ocular AEs were related to Vector A, and 48% of ocular AEs were related to the procedure. The most common ocular AEs comprised anterior chamber inflammation (15%), vitritis (9%), punctate keratitis (9%), and IOP elevation (8%).

At 48 weeks, tRNFL (temporal retinal nerve fiber layer)/PM (papillomacular) bundle thickness was significantly preserved in treated eyes and decreased in untreated eyes. Data pertaining to the change of RNFL temporal quadrant from baseline to week 48 are provided in Table 8.

TABLE 8

Secondary Efficacy Analysis
Change of RNFL Temporal Quadrant from Baseline to Week 48

| RNFL Quadrant Temporal (μm) | n | LS Mean (SE) [a] | 95% CI [a] | p-value |
|---|---|---|---|---|
| Change from Baseline to Week 48 All-Treated Eyes | 37 | −0.6 (1.0) | −2.6, 1.4 | |
| Change from Baseline to Week 48 All-Sham Eyes | 35 | −3.4 (1.0) | −5.4, −1.3 | |
| Difference between All-Treated Eyes and All-Sham Eyes Treatment Effect (95% CI) | 35 | 2.8 (0.2, 5.4) | | 0.0359 [a] |
| Wilcoxon Signed-Rank Test | | | | 0.0416 |

[a] A mixed model of analysis of covariance (ANCOVA) was used with change from baseline at week 48 as the response, and subject, eyes of the subject as random factor, treatment and the baseline GCL Thickness/Volume value as covariates in the model. LS mean refers to least-squares mean.

At 48 weeks, GCL (Ganglion cell layer) volume was significantly preserved in treated eyes and decreased in untreated eyes. At least these results suggested that the biological targets of Vector A were successfully engaged. Data pertaining to the change of GCL volume and topographical map from baseline to week 48 are presented in Table 9.

TABLE 9

Secondary Efficacy Analysis
Change of GCL Volume and Topographical
Map from Baseline to Week 48

| GCL Macular Volume ($mm^3$) | n | LS Mean (SE) [a] | 95% CI [a] | p-value |
|---|---|---|---|---|
| Change from Baseline to Week 48 All-Treated Eyes | 36 | −0.003 (0.012) | −0.028, 0.022 | |
| Change from Baseline to Week 48 All-Sham Eyes | 36 | −0.038 (0.012) | −0.062, −0.013 | |
| Difference between All-Treated Eyes and All-Sham Eyes Treatment Effect (95% CI) | 36 | 0.035 (0.006, 0.063) | | 0.0189 [a] |
| Wilcoxon Signed-Rank Test | | | | 0.0448 |

[a] A mixed model of analysis of covariance (ANCOVA) was used with change from baseline at week 48 as the response, and subject, eyes of the subject as random factor, treatment and the baseline GCL Thickness/Volume value as covariates in the model.

At 48 weeks, visual acuity improvement was observed in both eyes (−0.21 LogMAR on average). Data pertaining to the change of LogMAR from baseline to week 48 are presented in Table 10. No statistically significant difference between treated and untreated eyes was observed.

TABLE 10

Primary Efficacy Analysis
Change of LogMAR from Baseline to Week 48

| Visual acuity (LogMAR) | n | LS Mean (SE) [a] | 95% CI [a] | p-value |
|---|---|---|---|---|
| Change from Baseline to Week 48 All-Treated Eyes | 37 | −0.218 (0.055) | −0.328, −0.108 | |
| Change from Baseline to Week 48 All-Sham Eyes | 37 | −0.211 (0.055) | −0.320, −0.101 | |
| Difference between All-Treated Eyes and All-Sham Eyes Treatment Effect (95% CI) | 37 | −0.007 (−0.118, 0.103) | | 0.8942 [a] |
| Wilcoxon Signed-Rank Test | | | | 0.3875 |

[a] A mixed model of analysis of covariance (ANCOVA) was used with change from baseline at week 48 as the response, and subject, eyes of the subject as random factor, treatment and the baseline LogMAR value as covariates in the model.

At 48 weeks, visual field testing was performed using Humphrey® Visual Field analysis (mean deviation and foveal threshold). Data pertaining to the visual field testing are presented in Table 11 and Table 12. No difference between treated and untreated eyes was observed.

TABLE 11

| | | Mean (SD) | | |
|---|---|---|---|---|
| VF Foveal Threshold (dB) | n | Treated eyes | n | Sham eyes |
| Baseline | 13 | 19.6 (16.9) | 14 | 21.9 (15.0) |
| Week 48 | 25 | 14.9 (11.4) | 25 | 13.6 (11.6) |
| Change from baseline | 9 | 0.7 (8.9) | 11 | −0.5 (11.9) |

TABLE 12

| | | Mean (SD) | | |
|---|---|---|---|---|
| VF Mean Deviation (dB) | n | Treated eyes | n | Sham eyes |
| Baseline | 37 | −25.99 (8.37) | 37 | −24.94 (9.70) |
| Week 48 | 37 | −22.83 (9.43) | 37 | −22.94 (9.80) |
| Change from baseline | 37 | 3.15 (6.96) | 37 | 2.00 (5.04) |

Figure 5:
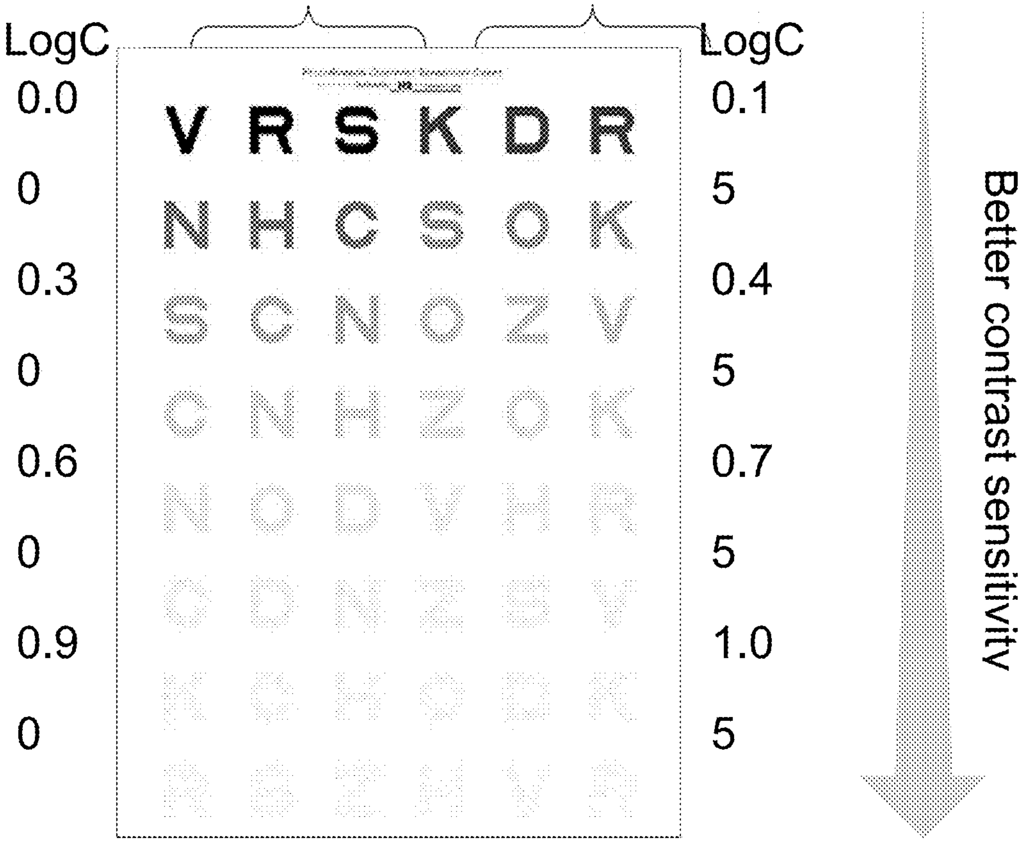
FIG. 5 depicts an example of a Pelli-Robson chart.

At 48 weeks, contrast sensitivity was assessed using the Pelli-Robson chart (see also FIG. 5). At baseline, contrast sensitivity was worse in treated eyes (as determined by LogMAR visual acuity). At week 48, the measure of contrast sensitivity in eyes treated with Vector A almost doubled, while the measure of contrast sensitivity in sham-treated eyes remained stable. Data pertaining to contrast sensitivity assessed using the Pelli-Robson chart are provided in Table 13.

TABLE 13

| Log of Contrast | | Mean (SD) | | |
|---|---|---|---|---|
| Sensitivity (LogCS) | n | Treated eyes | n | Sham eyes |
| Baseline | 37 | 0.25 (0.40) | 37 | 0.35 (0.46) |
| Week 48 | 37 | 0.45 (0.50) | 37 | 0.43 (0.49) |
| Change from baseline | 37 | 0.20 (0.36) | 37 | 0.08 (0.28) |

Color vision was tested using the Farnsworth-Munsell 100-hue color test. At baseline, extremely poor scores for color discrimination were observed. At week 48, no difference between treated and untreated eyes was observed. Data pertaining to color vision tested are presented in Table 14.

TABLE 14

| | | Mean (SD) | | |
|---|---|---|---|---|
| Total Error Score | n | Treated eyes | n | Sham eyes |
| Baseline | 28 | 649.3 (420.5) | 28 | 661.9 (433.7) |
| Week 48 | 28 | 623.6 (400.4) | 28 | 622.3 (430.3) |
| Change from baseline | 28 | −25.7 (235.6) | 28 | −39.6 (172.3) |

Quality of life was assessed at week 48 using the Visual Functional Questionnaire-25 (VFQ-25). Data from selected sub-scales are presented in Table 15. Although the difference in scores between scores is small, treatment of the patient's worse-seeing eye appeared to lead to improved quality of life metrics. Such a trend was observed across all sections of the questionnaire.

TABLE 15

| | | Mean scores at Week 48 (SD) | | |
|---|---|---|---|---|
| Selected sub-scales | n | Best-seeing Treated eyes | n | Best-seeing Sham eyes |
| General Vision | 16 | 38.8 (13.6) | 21 | 42.9 (20.3) |
| Near Activities | 16 | 32.3 (19.7) | 21 | 35.3 (19.7) |
| Distant Activities | 16 | 42.4 (22.3) | 21 | 47.0 (24.8) |

Study data were further analyzed to identify patient populations that were especially responsive to treatment with Vector A (e.g., patients for which an increase in visual acuity was observed).

Data pertaining to the change in visual acuity from baseline for on-chart best-seeing eyes treated with Vector A and for on-chart best-seeing eyes that were sham-treated are presented in Table 16. "On-chart" refers to subjects who can read at least three letters on an ETDRS chart and/or having visual acuity below 1.6 LogMAR.

TABLE 16

| Change from baseline in visual acuity (LogMAR) | n | LS Mean (SE) | 95% Confidence Interval | ETDRS letters equivalent |
|---|---|---|---|---|
| Best-seeing treated eyes | 12 | −0.236 (0.082) | −0.405, −0.067 | +12 |
| Best-seeing Sham eyes | 17 | −0.075 (0.069) | −0.216, 0.067 | +4* |
| p-value [a] | | 0.1466 | | |

[a] Significance of the difference between All-treated and All-Sham with respect to change of LogMAR from baseline.
*Does not statistically differ from 0.

The difference in the change in ETDRS score relative to baseline was measured. As shown in Table 17, this difference was greater for the set of on-chart best-seeing eyes relative to the set of all on-chart eyes (+6.1 versus +4.5).

TABLE 17

| Change from baseline in ETDRS score | Treated eyes | Sham eyes | Difference Treated - Untreated |
|---|---|---|---|
| | (n = 24) | (n = 28) | |
| All eyes | +8.8 | +4.3 | +4.5 |
| | (n = 13) | (n = 17) | |
| Best-seeing eyes | +9.8 | +3.7 | +6.1 |

Among the set of on-chart eyes treated with Vector A and for which an increase in visual acuity was measured at week 48, 75% (12/16) had a disease duration at baseline of 6 to 9 months, while 25% (4/16) had a disease duration at baseline of 9 to 12 months (Cf. Table 18). Among the set of on-chart sham-treated eyes for which an increase in visual acuity was measured at week 48, 50% (8/16) had a disease duration at baseline of 6 to 9 months, while 50% (8/16) had a disease duration at baseline of 9 to 12 months.

TABLE 18

| | Disease duration at baseline | | |
|---|---|---|---|
| | 6 to 9 months | 9 to 12 months | Total |
| Treated eyes | 12 (75%) | 4 (25%) | 16 |
| Sham eyes | 8 (50%) | 8 (50%) | 16 |
| Total | 20 | 12 | 32 |

In a further analysis, "responder" referred to improvement in visual acuity in on-chart patients of at least 0.25 LogMAR (+12.5 ETDRS equivalent). As shown in Table 19, 24.0% of all on-chart eyes treated with Vector A and 14.3% of all on-chart sham-treated eyes were characterized as "Responder Eyes."

TABLE 19

| | All On-chart Treated eyes | All On-chart Sham eyes |
|---|---|---|
| Responder eye | 6 (24.0%) | 4 (14.3%) |
| Non-Responder eye | 19 | 24 |
| McNemar p-value | 0.5637 | |

In a further analysis, "responder" referred to improvement in visual acuity in best-seeing eyes of on-chart patients of at least 0.25 LogMAR (+12.5 ETDRS equivalent). As shown in Table 20, 25.0% of on-chart best-seeing eyes treated with Vector A and 5.6% of best-seeing on-chart sham-treated eyes were characterized as "Responder Eyes."

TABLE 20

| | On-chart eyes | |
|---|---|---|
| | Best-seeing Treated eyes | Best-seeing Sham eyes |
| Responder eye | 3 (25.0%) | 1 (5.6%) |
| Non-Responder eye | 9 | 16 |
| McNemar p-value | 0.2785 | |

Study data were further analyzed using a generalized estimating equation (GEE) model to assess the effect of treatment with Vector A on achievement of a 20/200 visual acuity endpoint. Results showed that eyes treated with Vector A were significantly more likely to achieve the 20/200 visual acuity endpoint than were sham-treated eyes (p=0.0005). The odds ratio was 18.45 (lower 95% boundary=3.60).

Data pertaining to the number of eyes legally blind at baseline and, of those eyes blind at baseline, the number of eyes rescued from legal blindness are presented in Table 21. In this context, a legally-blind eye is defined as having visual acuity worse than 20/200.

TABLE 21

| | Treated eyes | Sham eyes |
|---|---|---|
| Number of eyes legally blind at baseline | 24 | 25 |
| Of those eyes blind at baseline, number of eyes rescued from legal blindness | 2 (8.3%) | 1 (4.0%) |

Analysis of the study data indicated that the set of patients who responded better to treatment with Vector A (e.g. patients for which an increase in visual acuity was observed) included those patients having a disease duration (e.g., vision loss) at baseline of less than 9 months, for example, of 6 to 9 months, and/or with visual acuity at baseline of <1.6 LogMAR. Thus, in some embodiments, these criteria (a disease duration (e.g., vision loss) at baseline of less than 9 months, for example, of 6 to 9 months and/or visual acuity at baseline of <1.6 LogMAR) may be used to identify a patient sub-population expected to better respond to treatment with Vector A (e.g., a patient population for which an increase in visual acuity may be expected).

Example 2

The trial evaluated the safety and efficacy of a single intravitreal injection of Vector A (rAAV2/2-ND4) in 37 subjects whose visual loss due to 11778-ND4 Leber Hereditary Optic Neuropathy (LHON) commenced between 6 and 12 months prior to study treatment. Week 96 is the last of the scheduled readouts for the trial and marks the time when the data are unmasked, providing access to individual patient profiles.

Figure 6:
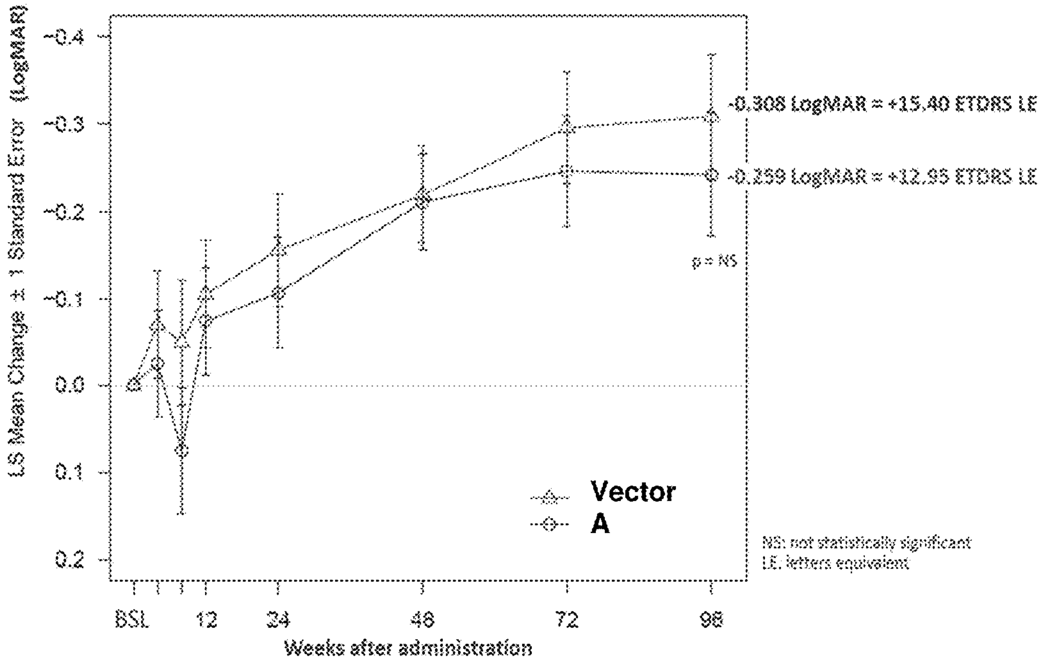
FIG. 6 depicts sustained bilateral improvement in BCVA with treatment.

ETDRS vision chart (FIG. 6). This clinically meaningful level of improvement in visual acuity maintains the gain observed at Week 72 (+14.7 ETDRS letters equivalent). As in readouts at Week 48 and Week 72, best-corrected visual acuity (BCVA) in sham-treated eyes evolved on a relatively parallel trajectory, achieving a mean improvement of −0.259 LogMAR over baseline, or a gain of +12.9 ETDRS letters equivalent, at Week 96. Although lower in magnitude, the mean BCVA improvement of sham-treated eyes was not statistically significant from that of Vector A-treated eyes.

Consistent with natural history, subjects experienced an initial point of low visual acuity, or nadir. The nadir is defined as the lowest post-treatment BCVA as measured by LogMAR up to the week of measurement. Eyes of trial subjects recovered significantly. By week 96, Vector A-treated eyes had gained +28 more letters relative to their nadir.

TABLE 22

| Recovery of BCVA from nadir as measured by difference from nadir in ETDRS letters equivalent, mean and standard deviation | | | | |
|---|---|---|---|---|
| | n | Week 48 | Week 72 | Week 96 |
| Vector A-treated eyes | 37 | +24.1 (21.1) | +27.4 (21.8) | +28.1 (22.0) |
| Sham-treated eyes | 37 | +20.3 (23.4) | +22.6 (25.5) | +23.2 (24.5) |

Figure 7:
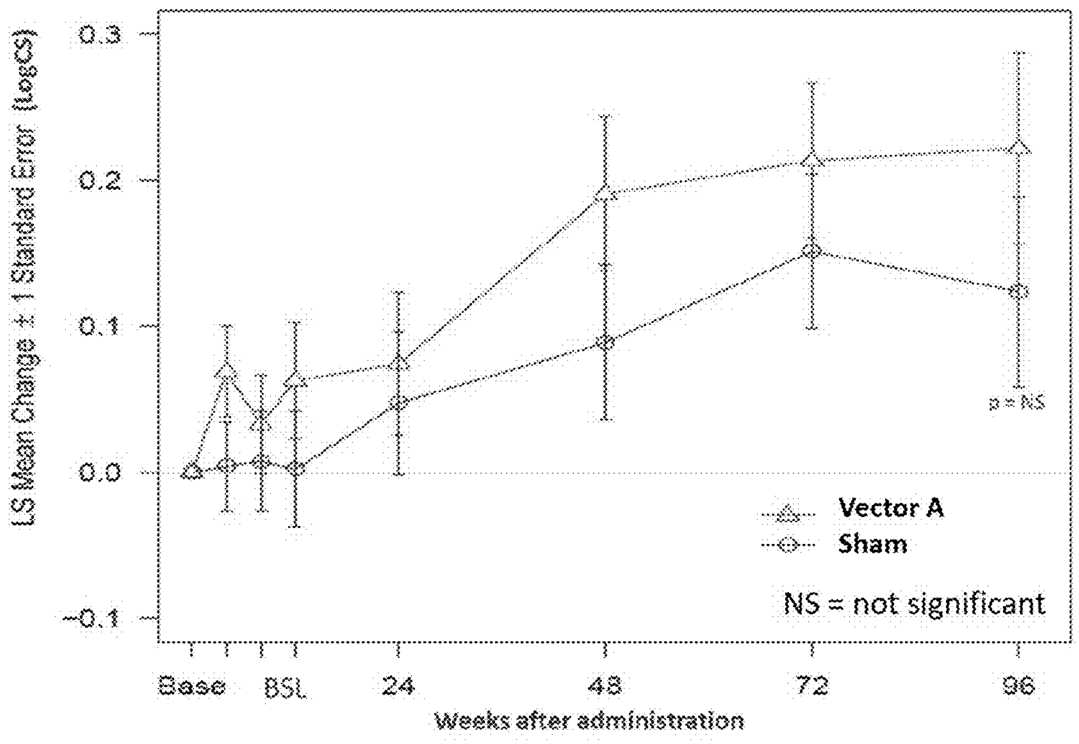
FIG. 7 depicts the evolution in contrast sensitivity during the course of study.

At Week 96, low-contrast visual acuity, as measured on the Pelli-Robson chart showed a similar trend of improvement for both Vector A-treated eyes and sham-treated eyes. The trajectories of sham- and Vector A-treated eyes did not track each other as closely as BCVA. Mean contrast sensitivity showed a more robust improvement versus baseline over the course of the trial (FIG. 7).

The proportion of Vector A-treated eyes that achieved at least a −0.2 LogMAR or +10 ETDRS letters equivalent improvement versus baseline at Week 96 is statistically significantly higher than the corresponding proportion of sham-treated eyes (65% vs. 46%, p-value=0.0348). Vector A-treated eyes were also significantly more likely than sham-treated eyes to achieve another measure of treatment success—improving by at least 15 ETDRS letters at Week 96 from on-chart acuity at baseline, or avoiding the US legal blindness threshold of 20/200 at Week 96 (32% vs. 16%, p=0.0196).

Based on a generalized estimating equations (GEE) model, Vector A-treated eyes were 2.8 times more likely to be at or above 20/200 than sham-treated eyes (p=0.0094). When only eyes that were strictly above the threshold were considered, the odds ratio rose to 3.6 (p=0.0032).

Additionally, 68% of trial subjects achieved a spontaneous "clinically relevant recovery (CRR)" in at least one eye at Week 96, defined by an improvement of (a) at least 10 ETDRS letters from on-chart visual acuity, or (b) an improvement from off-chart visual acuity to being able to read at least 5 ETDRS letters. Vector A-treated eyes were significantly more likely to achieve this than sham-treated eyes (62% vs. 43%, p=0.0348). In comparison, in a previous natural history study, only 15% of patients with the same 11778A mutation achieved CRR.

In terms of quality of life, improvement in visual function were reflected in scores on the National Eye Institute Visual Function Questionnaire-25 (NEI VFQ-25) survey, a validated, vision-specific quality-of-life instrument completed by trial subjects. As shown in Table 23, mean composite score and means of relevant sub-scale scores continued to improve over baseline, particularly for the ability to carry out near and distance activities. The increase over baseline of the mean sub-scale scores exceeded those that have been associated with a 15-letter improvement in BCVA in other ocular diseases.

TABLE 23

Meaningful Improvements in Quality of Life Scores Reported by Patients (NEI VFQ-25) - Mean change from baseline (absolute score and percentage)

| | Composite Score** | Near Activities | Distance Activities | Dependency | Role Difficulties | General Vision | Mental Health |
|---|---|---|---|---|---|---|---|
| Week 48 | +7.2 | +10.4 | +9.6 | +12.4 | +14.5 | +10.3 | +11.2 |
| | +23.2% | +65.1% | +49.8% | +100.6% | +65.0% | +50.9% | +81.9% |
| Week 72 | +8.1 | +9.5 | +8.2 | +18.9 | +15.2 | +11.9 | +15.2 |
| | +25.2% | +58.1% | +42.5% | +130.2% | +70.9% | +54.1% | +105.6% |
| Week 96 | +9.5 | +13.3 | +10.7 | +18.5 | +15.9 | +6.5 | +16.1 |
| | +28.8% | +78.1% | +47.4% | +130.2% | +78.9% | +32.4% | +108.2% |
| Clinically Relevant Difference | +3.90 to +4.34 | +4.67 to +6.06 | +5.15 to +5.38 | +4.72 to +4.98 | +3.31 to +4.70 | +4.38 to +4.82 | +4.70 to +4.88 |

**The composite score is an average of the vision-targeted sub-scale scores, excluding the general health rating question.

Structural metrics indicate that GS010-treated eyes maintained the stability achieved in previous readouts in ganglion cell volume. The differential effect of therapy was, however, more prominent in previous readouts.

The invention claimed is:

1. A method of treating Leber Hereditary Optic Neuroretinopathy (LHON) in a patient with ND4-related LHON and LHON disease duration of six to twelve months from an onset of vision loss, comprising administering intravitreally to the patient in need thereof an effective amount of a recombinant AAV2 vector comprising:

a 3'UTR Cox10 sequence comprising SEQ ID No: 14, a nucleic acid sequence encoding an NADH dehydrogenase 4 (ND4) polypeptide comprising SEQ ID No: 13, and a nucleic acid sequence encoding an MTS Cox10 polypeptide comprising SEQ ID No: 11 or SEQ ID No: 12.

2. The method according to claim 1, wherein the patient has experienced a disease duration of nine to twelve months from the onset of vision loss.

3. The method according to claim 2, wherein the patient has a baseline visual acuity of less than about 1.6 LogMAR.

4. The method according to claim 1, wherein the patient has experienced a disease duration of six to nine months from the onset of vision loss.

5. The method according to claim 4, wherein the patient has a baseline visual acuity of less than about 1.6 LogMAR.

6. The method according to claim 1, wherein the patient has a baseline visual acuity of less than about 1.6 LogMAR.

7. The method according to claim 1, wherein the patient has a G11778A mitochondrial DNA point mutation in the ND4 gene.

8. The method according to claim 1, wherein the recombinant AAV2 vector is administered intravitreally in an amount of about $10^9$ to $10^{11}$ viral genomes per eye.

9. The method according to claim 1, wherein the recombinant AAV2 vector is administered intravitreally in an amount of about $10^{10}$ to $10^{11}$ viral genomes per eye.

10. The method according to claim 1, wherein the recombinant AAV2 vector is administered intravitreally in an amount of about $5.0\times10^{10}$ to $1.0\times10^{11}$ viral genomes per eye.

11. The method according to claim 1, wherein the recombinant AAV2 vector is administered intravitreally in an amount of about $9.0\times10^{10}$ viral genomes per eye.

12. A method for treating a patient suffering from Leber Hereditary Optic Neuroretinopathy (LHON) with a recombinant AAV2 vector comprising:

i) confirming that the patient exhibits a G11778A mutation in the ND4 gene, ii) determining vision loss and LHON disease duration at baseline prior to treatment, iii) selecting the patient for administration of the recombinant AAV2 vector if the patient has vision loss and has experienced an LHON disease duration of six to twelve months from an onset of the vision loss; and iv) administering intravitreally, to the patient, an effective amount of the recombinant AAV2 vector, the recombinant AAV2 vector comprising:

a 3'UTR Cox10 sequence comprising SEQ ID No: 14, a nucleic acid sequence encoding an NADH dehydrogenase 4 (ND4) polypeptide comprising SEQ ID No: 13, and a nucleic acid sequence encoding an MTS Cox10 polypeptide comprising SEQ ID No: 11 or SEQ ID No: 12.

* * * * *